US006875854B1

(12) United States Patent
Castrillon

(10) Patent No.: US 6,875,854 B1

(45) Date of Patent: Apr. 5, 2005

(54) COMPOSITIONS AND METHODS FOR THE IMPROVED DIAGNOSIS AND TREATMENT OF GERM CELL TUMORS

(75) Inventor: Diego H. Castrillon, West Roxbury, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 399 days.

(21) Appl. No.: 09/714,865

(22) Filed: Nov. 16, 2000

Related U.S. Application Data

(60) Provisional application No. 60/166,394, filed on Nov. 18, 1999.

(51) Int. Cl.[7] .............................................. C07H 21/04

(52) U.S. Cl. .................................................... 536/23.5

(58) Field of Search ........................................ 536/23.5

(56) References Cited

U.S. PATENT DOCUMENTS 5,688,649 A 11/1997 Croce et al.
5,723,302 A 3/1998 Diamandis
5,935,775 A 8/1999 Savjani
6,639,063 B1 * 10/2003 Edwards et al. ........... 536/23.5

OTHER PUBLICATIONS

The New England Biolabs Catalog (1994, p. 91).*

Hloch et al (Nucleic Acids Research, 1990, vol. 18, p. 3045).*

Lemaire et al (Life Sciences, 1993, vol. 52, pp. 917–9260).*

Castrillon et al (PNAS, 2000, vol. 97, pp. 9585–9590).*

Accession No. A1217144, National Cancer Institute, Cancer Genome Anatomy Project (CGAP) tumor gene index, Soares_testis NHT Homo Sapiens cDNA clone IMAGE:1753173 3' similar to SW:DDX4_rat Q64060 cDNA clone IMAGE:1753173 3' similar to SW:DDX4_rat Q64060 Dead Box Protein 4 mRNA sequence, Nov. 10, 1998 ABSTRACT.

Accession No. AA383535, Adams, et al., "Initial assessment of human diversity and expression patterns based upon 83 million nucleotides of cDNA sequence", Apr. 21, 1997 ABSTRACT.

Accession No. AA399611, Hillier, et al., "WashU–Merck EST Project 1997", unpublished (1997) ABSTRACT.

Accession No. O00571 Lee, et al., *Korean J. Biochem.,* 27, 193–197 (1995) ABSTRACT.

Accession No. S75275, Komiya, et al., "Cloning of a gene of the dead box protein family which is specifically expressed in germ cells in rats", *Biochem. Biophys. Res. Commun.,* 207(1):405–410 (1995) ABSTRACT.

Collins, et al., "Plasma FSH, LH and testosterone levels in the male rate during degeneration of the germinal epithelium caused by severe heat treatment or ligation of the vasa efferentia", *J. Reprod. Fertil.,* 54(2):285–91 (1978) ABSTRACT.

Cortes, et al., "Laparoscopy in 100 consecutive patients with 128 impalpable testes", *Br. J. Urol.,* 75(3):281–7 (1995) ABSTRACT.

de Valoir, et al., "A second maternally expressed Drosophila gene encodes a putative RNA helicase of the "DEAD box" family", *Proc. Natl. Acad. Sci.,* USA 88(6):2113–7 (1991) ABSTRACT.

Fujiwara, et al., "Isolation of a DEAD–family protein gene that encodes a murine homolog of Drosophila vasa and its specific expression in germ cell linage", *Proc. Natl. Acad. Sci.* USA, 91(25):12258–62 (1994) ABSTRACT.

Michael, et al., "Primitive neuroectodermal tumors arising in testicular germ cell neoplasms", *Am. J. Surg. Pathol.,* 21 (8):896–904 (1997) ABSTRACT.

Iida, et al., "Essential role of mitochondrially encoded large rRNA for germ–line formation in Drosophila embryos", *Proc. Natl. Acad. Sci,* USA, 95(19):11274–8 (1998) ABSTRACT.

Ikeda, et al., "The inv(11)(p15q22) chromosome translocation of therapy–related myelodysplasia with NU98–DDX10 and DDX10–NUP98 fusion transcripts", *Int. J. Hamatol.,* 69(3):160–4 (1999) ABSTRACT.

Ikenishi, et al., "Involvement of the protein of Xenopus vasa homolog (Xenopus vasa–like gene 1, XVLG1) in the differentiation of primordial germ cells", *Dev. Growth Differ.,* 39(5):625–33 (1997) ABSTRACT.

Komiya, et al., "Cloning of a gene of the DEAD box protein family which is specifically expressed in germ cells in rats", *Biochem. Biophys. Res. Commun.,* 207(1):405–10 (1995) ABSTRACT.

Komiya, et al., "Isolation and characterization of a novel gene of the DEAD box protein family which is specifically expressed in germ cells of *Xenopus laevis*", *Dev. Biol.,* 162(2):354–63 (1994) ABSTRACT.

Lasko, et al., "The product of the Drosophila gene vasa is very similar to eukaryotic initiation factor–4A", *Nature,* 335(6191):611–7 (1988) ABSTRACT.

Lemaire, et al., "High–level expression in male germ cells of murine P68 RNA helicase mRNA", *Life Sci.,* 52(11):917–26 (1993) ABSTRACT.

Liang, et al., "Localization of vasa protein to the Drosophila pole plasm is independent of its RNA–binding and helicase activities", *Development,* 120(5):1201–11 (1994) ABSTRACT.

(Continued)

*Primary Examiner*—Karen A. Canella

(74) *Attorney, Agent, or Firm*—Wolf, Greenfield & Sacks, P.C.

(57) ABSTRACT

The invention pertains to nucleic acids encoding a human vasa protein, including fragments and biologically functional variants thereof. The invention also pertains to therapeutics and diagnostics involving the foregoing proteins and genes and agents that bind the foregoing proteins and genes.

4 Claims, 1 Drawing Sheet

OTHER PUBLICATIONS

Obata, et al., "Cellular localization of alpha–fetaprotein (AFP), human chorionic gonadotropin (HCG), and carcinoembyronic antigen (CEA) in malignant germ cell tumors of the ovary using immunoperoxidase technique", *Nippon Sanka Fujinka Gallai Zasshi,* 32(6):757–66 (1980) ABSTRACT.

Olsen, et al., "A vasa–like gene in zebrafish identifies putative primordial germ cells", *Mech. Dev.,* 66(1–2):95–105 (1997) ABSTRACT.

Rafti, et al., "A Drosophila melanogaster homologue of the human DEAD–box gene DDX1", *Gene,* 171(2):225–9 (1996) ABSTRACT.

Shibata, et al., "Expression of vasa(vas)–related genes in germline cells and totipotent somatic stem cells of planarians", *Dev. Biol.,* 206(1):73–87 (1999) ABSTRACT.

Taylor, et al., "Clinical predictors of response in metastatic germ cell tumors", *Cancer,* 62(1):217–21 (1988) ABSTRACT.

* cited by examiner

COMPOSITIONS AND METHODS FOR THE IMPROVED DIAGNOSIS AND TREATMENT OF GERM CELL TUMORS

RELATED APPLICATIONS

This application claims priority under 35 USC §119(e) from U.S. Provisional Patent Application Ser. No. 60/166,394, filed on Nov. 18, 1999, entitled COMPOSITIONS AND METHODS FOR THE IMPROVED DIAGNOSIS AND TREATMENT OF GERM CELL TUMORS. The contents of the provisional application are hereby expressly incorporated by reference.

FIELD OF THE INVENTION

This invention relates to nucleic acids and encoded polypeptides of human vasa, and diagnostics and therapeutics related to medical conditions associated with such genes and polypeptides, including cancers.

BACKGROUND OF THE INVENTION

Germ cells are cells that are specialized to produce haploid gametes in multicellular organisms. Germ cell tumors represent a diverse family of neoplasms affecting a wide range of patients. The great majority of testicular tumors (the most common malignancy in young men) are malignant germ cell tumors. The most common ovarian tumor, the benign or "mature" teratoma, is also of germ cell origin. Additionally, malignant ovarian germ cell tumors and germ cell tumors of various subtypes are of relatively common occurrence in children. Interestingly, benign and malignant germ cell tumors also arise in extragonadal locations (the mediastinum and central nervous system). Although the histogenesis of these extragonadal tumors is poorly understood, they exhibit similar biological behavior to their gonadal counterparts.

Malignant germ cell tumors are subdivided based on histologic appearance into pure seminomas (most common), and nonseminomas that include embryonal carcinoma, teratoma, choriocarcinoma, and yolk sac tumor. Patterns of mixed histologic appearance are also of common occurrence. Seminoma closely resembles primitive germ cells without evidence of further differentiation. Embryonal carcinoma is more anaplastic than seminoma, often with gland-like areas, and is believed to represent early differentiation to other lineages. The remaining histologic subtypes recapitulate the various lineages of the primitive embryo, reflecting the totipotent character of germ cells. Teratoma, choriocarcinoma, and yolk sac tumors exhibit evidence of fetal, placental, and yolk sac differentiation, respectively.

Accurate tissue-based diagnosis and subtyping of germ cell tumors (i.e., seminomas vs. nonseminoma) is of paramount importance for the patient, due to differences in staging evaluation and subsequent management (See, e.g., Ch. 98 on "Testicular Cancer" in *Harrison's Principles of Internal Medicine,* 14th Edition, 1997, McGraw-Hill, Inc., N.Y.—hereinafter "Harrison's"). Yet, some germ cell tumors are difficult or even impossible to reliably diagnose or subtype due to the diverse histologic appearances of germ cell tumors and the existence of numerous other malignancies that can mimic germ cell tumors histologically. For example, clear cell carcinoma of the ovary can histologically resemble dysgerminoma (the ovarian counterparts of seminoma); mediastinal thymomas can be difficult to distinguish from germ cell tumors, and testicular lymphoma can mimic seminoma (Scully et al, 1999, *Armed Forces Institute of Pathology*, Washington, D.C.; Suster et al., Seminars in Diagnostic Pathology, 1995, 12(1): 98–104). In addition, metastases in patients with unsuspected primary germ cell tumors can be initially misdiagnosed, resulting in treatment delays.

Tumor-specific markers have been clinically useful for a variety of reasons, including accurate tissue-based diagnosis by immunohistochemistry, population-based screening, confirmation of a clinical diagnosis prior to surgery, and monitoring of patients in remission. In general, the clinical utility of a marker is directly proportional to its specificity. For example, β-hCG, a highly sensitive and specific marker for trophoblast, is indispensable in the diagnosis and clinical monitoring of patients with choriocarcinoma (it is also the basis of pregnancy tests), and α-fetoprotein (AFP) serves as a fairly sensitive marker of yolk sac differentiation. Serum assays for both AFP and β-hCG are routinely employed in the diagnosis of patients with suspected germ cell tumors to determine if non-seminomatous components are present (which would alter patient management) (Harrison's). Commercially-available AFP and β-hCG antibodies are also routinely employed in immunohistochemical assays performed by hospital laboratories on paraffin-embedded formalin-fixed tissue.

Currently available immunohistochemical markers for seminoma are relatively non-specific and no useful serum seminoma tumor markers exist, even though seminoma is the most common germ cell tumor subtype. Although placental-type alkaline phosphatase (PLAP) is a fairly sensitive (~80%) marker of seminoma, it is far from specific, being expressed in a variety of carcinomas including the majority of ovarian carcinomas, a significant number of gastrointestinal carcinomas, and several normal tissues (Sunderland et al, *Cancer Research,* 1984, 44(10): 4496–4502). Largely because of this lack of specificity, alkaline phosphatase serum assays are not being utilized routinely. Furthermore, PLAP is not reliably expressed in normal germ cells (Perry et al., *Human Pathology,* 1994, 25(3): 235–239). The development of a more specific and sensitive marker of seminoma would represent a major advance.

The vasa gene was originally described in *Drosophila*, where various studies including whole-mount in situ staining have, reportedly, shown that vasa is expressed only in germ cells (of both sexes) at all stages of development, from the preblastoderm stage to primitive germ cells to gametogenesis in adults. A number of investigations have, reportedly, shown that vasa is not only germ-cell specific in its expression, it is absolutely required for germ cell development, and in *Drosophila*, vasa mutants fail to develop germ cells (Lasko et al., *Nature,* 1988, 335:611–617, and SEQ ID NO:7). Subsequently, vasa homologues were identified in mouse, zebrafish, and *Xenopus*. In all of the foregoing species, expression was reportedly germ-cell specific and occurred throughout life. Reports on vasa expression in these organisms have greatly increased our knowledge of the germ-cell lineage, allowing germ-cell lineage cells to be traced back to the 4-cell morula stage (Fujiwara, et al., *Proc. Nat. Acad Scie. USA,* 1994, 6;91(25): 12258–12262; Yoon, et al., *Development,* 1997, 124:3157–3166; Ikenishi, et al., *Dev. Grow., and Diff,* 1997, 39:625–633).

There exists a need to identify agents that are useful in the diagnosis of tumors of germ cell origin.

These and other objects will be described in greater detail below.

SUMMARY OF THE INVENTION

We describe herein the molecular cloning and characterization of human vasa, a novel molecule that has germ cell specific expression and is believed to play a determinative role in gonad development. Aberrant expression of human vasa has been found in patients with tumors of germ cell origin, making human vasa a specific marker of tumors of such origin.

The invention provides isolated nucleic acid molecules, unique fragments of those molecules, expression vectors containing the foregoing, and host cells transfected with those molecules. The invention also provides isolated binding polypeptides and binding agents which bind such polypeptides, including antibodies. The foregoing can be used, inter alia, in the diagnosis or treatment of conditions characterized by the aberrant expression and/or the presence of mutant forms of a human vasa nucleic acid or polypeptide. The invention also provides methods for identifying pharmacological agents useful in the diagnosis or treatment of such conditions.

According to one aspect of the invention, isolated nucleic acid molecules that code for a human vasa polypeptide are provided and include: (a) nucleic acid molecules which hybridize under stringent conditions to a molecule consisting of a nucleotide sequence set forth as SEQ ID NO:1 and which code for a human vasa polypeptide, (b) nucleic acid molecules that differ from the nucleic acid molecules of (a) or (b) in codon sequence due to the degeneracy of the genetic code, and (c) complements of (a) or (b). In certain embodiments, the isolated nucleic acid molecule comprises nucleotides 1–2224 of SEQ ID NO:1. In some embodiments the isolated nucleic acid molecules are those comprising the human vasa cDNA corresponding to SEQ ID NO:15. The isolated nucleic acid molecule also can comprise a molecule which encodes the polypeptide of SEQ ID NO:2 and has human vasa specific expression. In certain embodiments, nucleic acids of the invention exclude nucleic acids completely composed of the nucleotide sequences of any of GenBank accession numbers listed in Table I (S75275, D14859, AB005147, Y12007, AF046043, Z81449.1, X81823, P09052, Q64060, Q61496, Q62167, 000571, P24346, P16381, 015523, AL042306, AA399611, AA398976, AA383535, AI217144, A1953070, A1025074, A1654417, A1337133, AA758412, A1969018, AA400066, AA862553, AA401568, AA316798, T85890, and T82153), or other previously published sequences as of the filing date of this application.

The invention in another aspect provides an isolated nucleic acid molecule selected from the group consisting of (a) unique fragments of a nucleotide sequence set forth as SEQ ID NO:1 (of sufficient length to represent a sequence unique within the human genome), (b) complements of (a), provided that a unique fragment of (a) includes a sequence of contiguous nucleotides which is not identical to a sequence selected from the sequence group consisting of: (1) sequences having the database accession numbers of Table I, or sequences encoding a polypeptide having an amino acid sequence selected from the group consisting of SEQ ID NO:3, SEQ ID NO:4, SEQ ID NO:5, SEQ ID NO:6, and SEQ ID NO:7, (2) complements of (1), and (3) fragments of (1) and (2).

In one embodiment, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In another embodiment, the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

According to another aspect, the invention provides expression vectors, and host cells transformed or transfected with such expression vectors, comprising the nucleic acid molecules described above.

According to another aspect of the invention, an isolated polypeptide is provided. The isolated polypeptide is encoded by the foregoing isolated nucleic acid molecules of the invention. In some embodiments, the isolated polypeptide is encoded by the nucleic acid of SEQ ID NO:1, giving rise to a polypeptide having the sequence of SEQ ID NO:2 that has germ cell specific expression. In other embodiments, the isolated polypeptide may be a fragment or variant of the foregoing of sufficient length to represent a sequence unique within the human genome, and identifying with a polypeptide that has germ cell specific expression, provided that the fragment excludes: (i) a sequence of contiguous amino acids selected from the group consisting of SEQ ID NO:3, SEQ ID NO:4, SEQ ID NO:5, SEQ ID NO:6, and SEQ ID NO:7, and (ii) a sequence of contiguous amino acids encoded by an isolated nucleic acid having a nucleotide sequence with a GenBank database accession number selected from the group consisting of S75275, D14859, AB005147, Y12007, AF046043, Z81449.1, X81823, P09052, Q64060, Q61496, Q62167, 000571, P24346, P16381, 015523, AL042306, AA399611, AA398976, AA383535, A1217144, A1953070, A1025074, A1654417, A1337133, AA758412, A1969018, AA400066, AA862553, AA401568, AA316798, T85890, and T82153. (i.e., as described in Table I). In another embodiment, immunogenic fragments of the polypeptide molecules described above are provided.

According to another aspect of the invention, isolated binding polypeptides which selectively bind a polypeptide encoded by the foregoing isolated nucleic acid molecules of the invention are provided. Preferably the isolated binding polypeptides selectively bind a polypeptide which comprises the sequence of SEQ ID NO:2, SEQ ID NO:9, SEQ ID NO:10, or fragments thereof. In preferred embodiments, the isolated binding polypeptides include antibodies and fragments of antibodies (e.g., Fab, $F(ab')_2$, Fd and antibody fragments which include a CDR3 region which binds selectively to the human vasa polypeptide). In certain embodiments, the antibodies are human.

The invention also contemplates kits comprising a package including assays for human vasa epitopes, human vasa nucleic acids, and instructions, and optionally related materials such as controls, for example, a number, color chart, or an epitope of the expression product of the foregoing isolated nucleic acid molecules of the invention, for comparing the level of human vasa polypeptides or human vasa nucleic acids in a test sample to the level in a control sample. This comparison can be used to assess in a subject the presence of a tumor of germ cell origin. The kits may also include assays for other known genes, and expression products thereof, associated with cancers (e.g., β-hCG, α-fetoprotein, placental-type alkaline phosphatase, prostate specific antigen, carcinoembryonic antigen, inhibin, epithelial membrane antigen, desmin, vimentin, GFAP-glial fibrillary acidic protein, synaptophysin, chromogranin, cytokeratin isoforms such as 7 and 20, anti-keratin markers such as AE1/AE3 and CAM5.2, etc.).

Another aspect of the invention is a method for determining the level of vasa expression in a subject. Expression is defined either as vasa mRNA expression or vasa polypeptide expression. Various methods can be used to measure expression. Preferred embodiments of the invention include PCR and northern blotting for measuring mRNA expression, and monoclonal vasa antibodies or polyclonal vasa antisera as reagents to measure (or characterize) vasa polypeptide expression. In certain embodiments, test samples such as tissue (e.g., biopsy) samples, and biological fluids such as blood, are used as test samples. In some embodiments, fine-needle aspirates can also be used as sources of a test sample. Vasa expression in a test sample of a subject is compared to vasa expression in control sample to, e.g., assess the presence or absence, or stage of a tumor of germ cell origin in a subject.

According to another aspect, a method of detecting a tumor of germ cell origin, is provided. The method involves detecting vasa expression in an extragonadal test sample obtained from a subject. Vasa expression in the extragonadal test sample is indicative of the presence of a tumor of germ cell origin in the subject. Vasa expression and methods of measuring vasa expression are as described in any of the foregoing embodiments. In some embodiments, the subject has not previously been diagnosed as having a tumor of germ cell origin or a predisposition thereto [e.g., to detect a metastasis in a subject of previously undiagnosed cancer]. In certain embodiments, the subject has a clinical diagnosis of a tumor of germ cell origin and the method is to confirm the clinical diagnosis, monitor remission of the tumor, or stage the tumor.

According to yet another aspect, a method of detecting a tumor of germ cell origin, is provided. The method involves detecting vasa overexpression in a test sample obtained from a subject. Vasa overexpression in the test sample as compared to a control is indicative of a tumor of germ cell origin in the subject. Vasa expression and methods of measuring vasa expression are as described in any of the foregoing embodiments. In certain embodiments, the tumor can be a testicular tumor (e.g., a seminoma), an ovarian tumor (e.g., a dysgerminoma or a teratoma), or a tumor of an extragonadal tissue (e.g., a mediastinal tumor or an intracranial tumor). In some embodiments, the method can further comprise detecting expression of a tumor-specific agent other than a vasa molecule (nucleic acid or polypeptide) in the test sample. Tumor-specific agents other than a vasa molecule include, but are not limited to, β-hCG, α-fetoprotein, placental-type alkaline phosphatase, prostate specific antigen, carcinoembryonic antigen, inhibin, epithelial membrane antigen, desmin, vimentin, GFAP-glial fibrillary acidic protein, synaptophysin, chromogranin, cytokeratin isoforms such as 7 and 20, and anti-keratin markers such as AE1/AE3 and CAM5.2. Preferred subjects are as described in any of the foregoing embodiments.

According to another aspect, a method of subtyping tumors of germ cell origin is provided. The method involves detecting vasa expression in a test sample of a known or suspected germ cell origin tumor obtained from a subject. Vasa overexpression in the test sample as compared to a control is indicative of a seminoma in the subject, whereas absence of vasa expression in the test sample as compared to a control is indicative of a nonseminoma in the subject. Vasa expression, methods of measuring vasa expression, tumor types, and subjects, are as described in any of the foregoing embodiments. Nonseminomas include embryonal carcinoma, teratoma, choriocarcinoma, yolk sac tumor, or combinations of the foregoing. In certain embodiments, the subject has a clinical diagnosis of a tumor of mixed histologic appearance. In some embodiments, and preferably (but not exclusively) in the absence of vasa expression in the test sample, the method can further comprise detecting expression of a tumor-specific agent other than a vasa molecule in the test sample. Tumor-specific agents other than a vasa molecule are as described in any of the foregoing embodiments.

According to another aspect, a method of distinguishing a tumor of germ cell origin from a non-germ cell tumor, is provided. The method involves detecting expression of a vasa molecule in a test sample, wherein expression of the vasa molecule is indicative of a tumor of a germ cell origin and absence of expression of the vasa molecule is indicative of a non-germ cell tumor. In certain embodiments, the non-germ cell tumor resembles histologically a tumor of germ cell origin. Non-germ cell tumors include, but are not limited to, clear cell carcinoma of the ovary (can resemble dysgerminoma), a mediastinal thymoma, and a testicular lymphoma.

According to a further aspect, a method for treating a tumor of germ cell origin in a subject, is provided. The method involves administering to a subject in need of such treatment an agent that inhibits vasa expression in a germ cell of the subject in an effective amount to inhibit vasa expression and inhibit the growth and/or proliferation of the tumor of germ cell origin in the subject. In a preferred embodiment, the agent is a vasa antisense nucleic acid. In certain embodiments, the method further comprises co-administering an anti-cancer agent.

According to another aspect of the invention, methods for preparing medicaments useful in the treatment of a tumor of germ cell origin, are also provided.

The present invention thus involves, in several aspects, human vasa polypeptides, isolated nucleic acids encoding those polypeptides, functional modifications and variants of the foregoing, useful fragments of the foregoing, as well as therapeutics and diagnostics relating thereto.

These and other objects of the invention will be described in further detail in connection with the detailed description of the invention.

BRIEF DESCRIPTION OF THE SEQUENCES

Figure 1:
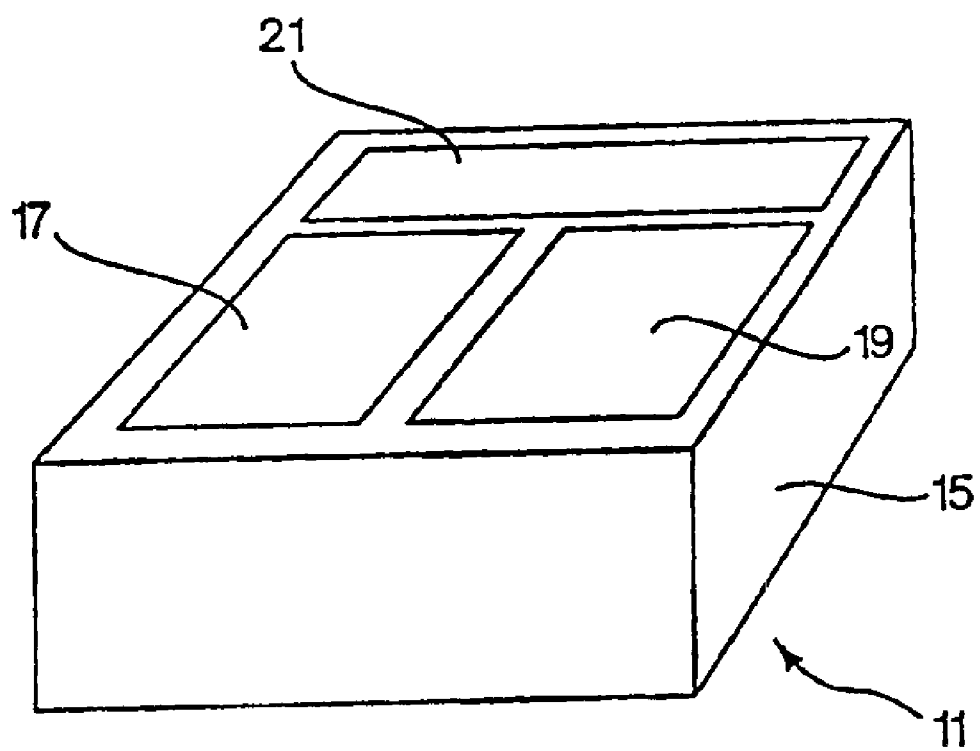
FIG. 1 depicts a kit comprising an agent of the invention (e.g., anti-human vasa Abs, human vasa epitopes, etc.), a control agent, and instructions for utilizing such agents in diagnostic or therapeutic applications.

SEQ ID NO: 1 is the nucleotide sequence of the human vasa cDNA.

SEQ ID NO:2 is the predicted amino acid sequence of the translation product of human vasa cDNA (SEQ ID NO:1).

SEQ ID NO:3 is the amino acid sequence of the *Mus Musculus* vasa cDNA.

SEQ ID NO:4 is the amino acid sequence of the *Rattus Norvegicus* vasa cDNA.

SEQ ID NO:5 is the amino acid sequence of the *Xenopus Laevis* vasa cDNA.

SEQ ID NO:6 is the amino acid sequence of the *Danio Reio* vasa cDNA.

SEQ ID NO:7 is the amino acid sequence of the *Drosophila Melanogaster* vasa cDNA.

SEQ ID NO:8 is the nucleotide sequence of a synthetic oligonucleotide primer used in the cloning of the human vasa cDNA.

SEQ ID NO:9 is the amino acid sequence of a human-specific vasa epitope used in the generation of anti-human vasa antibodies.

SEQ ID NO:10 is the amino acid sequence of a human-specific vasa epitope used in the generation of anti-human vasa antibodies.

SEQ ID NO:11 is the nucleotide sequence of a synthetic human vasa oligonucleotide.

SEQ ID NO:12 is the nucleotide sequence of a synthetic human vasa oligonucleotide.

SEQ ID NO:13 is the nucleotide sequence of a synthetic oligonucleotide primer used in the detection of human vasa expression using PCR in combination with the synthetic oligonucleotide primer of SEQ ID NO:14.

SEQ ID NO:14 is the nucleotide sequence of a synthetic oligonucleotide primer used in the detection of human vasa expression using PCR in combination with the synthetic oligonucleotide primer of SEQ ID NO: 13.

SEQ ID NO:15 is the nucleotide sequence of the largest open reading frame of the human vasa cDNA of SEQ ID NO: 1, encoding for the polypeptide of SEQ ID NO:2.

DETAILED DESCRIPTION OF THE INVENTION

One aspect of the invention involves the cloning of a cDNA encoding human vasa. Human vasa according to the invention is an isolated nucleic acid molecule that comprises a nucleic acid molecule of SEQ ID NO: 1, and codes for a protein that is specifically expressed in the gonads and is believed to play an essential role in gonad development. According to the invention, aberrant expression of human vasa has been found in patients with tumors of germ cell origin, making human vasa a specific marker for tumors of such origin. The sequence of the human vasa cDNA is presented as SEQ ID NO:1, and the predicted amino acid sequence of this cDNA's encoded protein product is presented as SEQ ID NO:2.

As used herein, a subject is a human, non-human primate, cow, horse, pig, sheep, goat, dog, cat or rodent. In all embodiments human vasa and human subjects are preferred.

The invention thus involves in one aspect an isolated human vasa polypeptide, the cDNA encoding this polypeptide, functional modifications and variants of the foregoing, useful fragments of the foregoing, as well as diagnostics and therapeutics relating thereto.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

According to the invention, isolated nucleic acid molecules that code for a human vasa polypeptide include: (a) nucleic acid molecules which hybridize under stringent conditions to a molecule consisting of a nucleic acid of SEQ ID NO:1 and which code for a human vasa polypeptide, (b) deletions, additions, and substitutions of (a) which code for a respective human vasa polypeptide, (c) nucleic acid molecules that differ from the nucleic acid molecules of (a) or (b) in codon sequence due to the degeneracy of the genetic code, and (d) complements of (a), (b) or (c). In certain embodiments, nucleic acids of the invention exclude nucleic acids completely composed of the nucleotide sequences of any of GenBank accession numbers listed in Table I (S75275, D14859, AB005147, Y12007, AF046043, Z81449.1, X81823, P09052, Q64060, Q61496, Q62167, 000571, P24346, P16381, 015523, AL042306, AA399611, AA398976, AA383535, A1217144, AI953070, A1025074, A1654417, A1337133, AA758412, A1969018, AA400066, AA862553, AA401568, AA316798, T85890, and T82153), or other previously published sequences as of the filing date of this application.

Homologs and alleles of the human vasa nucleic acids of the invention can be identified by conventional techniques. Thus, an aspect of the invention is those nucleic acid sequences which code for human vasa polypeptides and which hybridize to a nucleic acid molecule consisting of the coding region of SEQ ID NO:1, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015 M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of human vasa nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 75% nucleotide identity and/or at least 90% amino acid identity to SEQ ID NO:1 and SEQ ID NO:2, respectively. In some instances homologs and alleles will share at least 90% nucleotide identity and/or at least 95% amino acid identity and in still other instances will share at least 0.95% nucleotide identity and/or at least 99% amino acid identity. Complements of the foregoing nucleic acids also are software tools developed by NCBI (Bethesda, Md.). Exemplary tools include the heuristic algorithm of Altschul SF, et al., (*J Mol Biol,* 1990, 215:403–410), also known as BLAST. Pairwise and ClustalW alignments (BLOSUM30 matrix setting) as well as Kyte-Doolittle hydropathic analysis can be obtained using public (EMBL, Heidelberg, Germany) and commercial (e.g., the MacVector sequence analysis software from Oxford Molecular Group/Genetics Computer Group, Madison, Wis.). Watson-Crick complements of the foregoing nucleic acids also are embraced by the invention.

In screening for human vasa related genes, such as homologs and alleles of human vasa, a Southern blot may be performed using the foregoing conditions, together with a radioactive probe. After washing the membrane to which the DNA is finally transferred, the membrane can be placed against X-ray film or a phosphoimager plate to detect the radioactive signal.

Given that the expression of the human vasa gene is abundant in certain human tissues, and given the teachings herein of a human vasa cDNA clone encoding for the complete vasa polypeptide, allelic human vasa sequences can be isolated from cDNA libraries prepared from one or more of the tissues in which human vasa expression is abundant (i.e., in the gonads), using standard colony hybridization techniques.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating human vasa polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO: 1 or SEQ ID NO:15, or complements thereof. A unique fragment is one that is a 'signature' for the larger nucleic acid. For example, the unique fragment is long enough to assure that its precise sequence is not found in molecules within the human genome outside of the human vasa nucleic acids defined above. Those of ordinary skill in the art may apply no more than routine procedures to determine if a fragment is unique within the human genome. Unique fragments, however, exclude fragments completely composed of the nucleotide sequences of any of GenBank accession numbers listed in Table I (S75275, D14859, AB005147, Y12007, AF046043, Z81449.1, X81823, P09052, Q64060, Q61496, Q62167, 000571, P24346, P16381, 015523, AL042306, AA399611, AA398976, AA383535, A1217144, A1953070, A1025074, A1654417, AI337133, AA758412, A1969018, AA400066, AA862553, AA401568, AA316798, T85890, and T82153), or other previously published sequences as of the filing date of this application.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the human vasa polypeptides, useful, for example, in the preparation of antibodies, immunoassays or therapeutic applications. Unique fragments further can be used as antisense molecules to inhibit the expression of human vasa nucleic acids and polypeptides respectively.

As will be recognized by those skilled in the art, the size of the unique fragment will depend upon its conservancy in the genetic code. Thus, some regions of SEQ ID NO: 1 or SEQ ID NO:15 and complements will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). Virtually any segment of the region of SEQ ID NO:1 beginning at nucleotide 1 and ending at nucleotide 2224, or SEQ ID NO:15 beginning at nucleotide 1 and ending at nucleotide 2172, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As mentioned above, the invention embraces antisense oligonucleotides that selectively bind to a nucleic acid molecule encoding a human vasa polypeptide, to decrease human vasa activity. When using antisense preparations of the invention, slow intravenous administration is preferred.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1 or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nat. Med.* 1(11): 1116–1118, 1995). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5): 439–457, 1994) and at which proteins are not expected to bind. Finally, although, SEQ ID No:1 discloses a cDNA sequence, one of ordinary skill in the art may easily derive the genomic DNA corresponding to this sequence. Thus, the present invention also provides for antisense oligonucleotides which are complementary to the genomic DNA corresponding to SEQ ID NO: 1. Similarly, antisense to allelic or homologous human vasa cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding human vasa polypeptides, together with pharmaceutically acceptable carriers. Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The invention also involves expression vectors coding for human vasa proteins and fragments and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as *E. coli* and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding human vasa polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV and pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell Biol.* 16:47104716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno-.PIA recombinant is disclosed by Warnier et al, in intradermal injection in mice for immunization against PIA (*Int. J. Cancer,* 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, human vasa cDNA sequence containing expression vectors, to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells. The invention also permits the construction of human vasa gene "knock-outs" in cells and in animals, providing materials for studying certain aspects of human vasa activity.

The invention also provides isolated polypeptides (including whole proteins and partial proteins), encoded by the foregoing human vasa nucleic acids, and include the polypeptide of SEQ ID NO:2 and unique fragments thereof. Such polypeptides are useful, for example to generate antibodies, as components of an immunoassay, etc. Polypeptides can be to isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of an human vasa polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2 will require longer segments to be unique while others will require only short segments, typically between 5 and 12 amino acids (e.g. 5, 6, 7, 8, 9, 10, 11 and 12 amino acids long or more, including each integer up to the full length, 474 amino acids long). Virtually any segment of SEQ ID NO:2, excluding the ones that share identity with it (the polypeptides having amino acid sequences as set forth in SEQ ID NOs:3, 4, 5, 6, and 7) that is 9 or more amino acids in length will be unique.

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, selective binding to receptors, tissue specific expression, etc. One important activity is the ability to act as a signature for identifying the polypeptide. Another is the ability to complex with HLA and to provoke in a human an immune response. Those skilled in the art are well versed in methods for selecting unique amino acid sequences, typically on the basis of the ability of the unique fragment to selectively distinguish the sequence of interest from non-family members or from family members of other species. A comparison of the sequence of the fragment to those on known databases typically is all that is necessary.

The invention embraces variants of the human vasa polypeptides described above. As used herein, a "variant" of a human vasa polypeptide is a polypeptide which contains one or more modification to the primary amino acid sequence of a human vasa polypeptide. Modifications which create a human vasa polypeptide variant are typically made to the nucleic acid which encodes the human vasa polypeptide, and can include deletions, point mutations, truncations, amino acid substitutions and addition of amino acids or non-amino acid moieties to: I) reduce or eliminate an activity of a human vasa polypeptide; 2) enhance a property of a human vasa polypeptide, such as protein stability in an expression system or the stability of protein—protein binding; 3) provide a novel activity or property to a human vasa polypeptide, such as addition of an antigenic epitope or addition of a detectable moiety; or 4) to provide equivalent or better binding to a human vasa polypeptide receptor or other molecule (e.g., heparin). Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the human vasa amino acid sequence. One of skill in the art will be familiar with methods for predicting the effect on protein conformation of a change in protein sequence, and can thus "design" a variant human vasa polypeptide according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

Variants can include human vasa polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a human vasa polypeptide by eliminating proteolysis by proteases in an expression system (e.g., dibasic amino acid residues in yeast expression systems in which KEX2 protease activity is present).

Mutations of a nucleic acid which encodes a human vasa polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant human vasa polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a human vasa gene or cDNA clone to enhance expression of the polypeptide.

The skilled artisan will realize that conservative amino acid substitutions may be made in human vasa polypeptides to provide functionally equivalent variants of the foregoing polypeptides, i.e, the variants retain the functional capabilities of the human vasa polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning. A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the human vasa polypeptides include conservative amino acid substitutions of SEQ ID NO:2. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of human vasa polypeptides, i.e., variants of human vasa polypeptides which retain the function of the natural human vasa polypeptides, are contemplated by the invention. Conservative amino-acid substitutions in the amino acid sequence of human vasa polypeptides to produce functionally equivalent variants of human vasa polypeptides typically are made by alteration of a nucleic acid encoding human vasa polypeptides (SEQ ID NOs:1, 15). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a human vasa polypeptide. The activity of functionally equivalent fragments of human vasa polypeptides can be tested by cloning the gene encoding the altered human vasa polypeptide into a bacterial or mammalian expression vector, introducing the vector into an appropriate host cell, expressing the altered human vasa polypeptide, and testing for a functional capability of the human vasa polypeptides as disclosed herein (e.g., germ cell specific expression, etc.).

The invention as described herein has a number of uses, some of which are described elsewhere herein. First, the invention permits isolation of human vasa polypeptides. A variety of methodologies well-known to the skilled practitioner can be utilized to obtain isolated human vasa molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of human vasa mRNA in cell-free extracts such as the reticulocyte lysate system also may be used to produce human vasa polypeptides. Those skilled in the art also can readily follow known methods for isolating human vasa polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from human vasa polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

The isolation of the human vasa cDNA also makes it possible for the artisan to diagnose a disorder characterized by an aberrant expression of human vasa. These methods involve determining expression of the human vasa gene, and/or human vasa polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the secreted human vasa protein.

The invention also embraces isolated peptide binding agents which, for example, can be antibodies or fragments of antibodies ("binding polypeptides"), having the ability to selectively bind to human vasa polypeptides. Antibodies include polyclonal and monoclonal antibodies, prepared according to conventional methodology. In certain embodiments, the invention excludes binding agents (e.g., antibodies) that bind to the polypeptides encoded by the nucleic acids of SEQ ID NOs:3, 4, 5, 6, and 7, and/or the nucleic acids having nucleotide sequences with GenBank accession numbers as those described in Table I, and/or polypeptides having amino acid sequences with GenBank accession numbers as those described in Table I.

Significantly, as is well-known in the art, only a small portion of an antibody molecule, the paratope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to human vasa polypeptides, and complexes of both human vasa polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the human vasa polypeptide or a complex of human vasa and a binding partner. This process can be repeated through several cycles of reselection of phage that bind to the human vasa polypeptide or complex. Repeated rounds lead to enrichment of phage bearing particular sequences. DNA sequence analysis can be conducted to identify the sequences of the expressed polypeptides. The minimal linear portion of the sequence that binds to the human vasa polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the human vasa polypeptides. Thus, the human vasa polypeptides of the invention, or a fragment thereof, or complexes of human vasa and a binding partner can be used to screen peptide libraries, including phage display libraries, to identify and select peptide binding partners of the human vasa polypeptides of the invention. Such molecules can be used, as described, for screening assays, for purification protocols, for interfering directly with the functioning of human vasa and for other purposes that will be apparent to those of ordinary skill in the art.

A human vasa polypeptide, or a fragment thereof, also can be used to isolate their native binding partners. Isolation of binding partners may be performed according to well-known methods. For example, isolated human vasa polypeptides (that include human vasa phosporylated polypeptides) can be attached to a substrate, and then a solution suspected of containing an human vasa binding partner may be applied to the substrate. If the binding partner for human vasa polypeptides is present in the solution, then it will bind to the substrate-bound human vasa polypeptide. The binding partner then may be isolated. Other proteins which are binding partners for human vasa, may be isolated by similar methods without undue experimentation.

The invention also provides novel kits which could be used to measure the levels of the nucleic acids of the invention, expression products of the invention or anti-human vasa antibodies. In the case of nucleic acid detection, pairs of primers for amplifying human vasa nucleic acids can be included. The preferred kits would include controls such as known amounts of nucleic acid probes, human vasa epitopes (such as human vasa expression products) or anti-human vasa antibodies, as well as instructions or other printed material. In certain embodiments the printed material can characterize the presence of a tumor based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with human vasa protein and a container containing labeled anti-human IgG antibodies. A well of the plate is contacted with, for example, serum, washed and then contacted with the anti-IgG antibody. The label is then detected. A kit embodying features of the present invention, generally designated by the numeral 11, is illustrated in FIG. 1. Kit 11 is comprised of the following major elements: packaging 15, an agent of the invention 17 (e.g., an anti-human vasa antibody), a control agent 19 (e.g., a human vasa epitope), and instructions 21. Packaging 15 is a box-like structure for holding a vial (or number of vials) containing an agent of the invention 17, a vial (or number of vials) containing a control agent 19, and instructions 21. Individuals skilled in the art can readily modify packaging 15 to suit individual needs.

The invention also provides methods to measure the level of human vasa expression in a subject. This can be performed by first obtaining a test sample from the subject. The test sample can be tissue, biological fluid, or both (as, for example, in a fine needle aspirate). Tissues include brain, heart, serum, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. In certain embodiments, test samples originate from brain, testis, breast and prostate tissues, and biological fluids include blood, saliva, semen, fellopian fluid, and urine. Both invasive and non-invasive techniques can be used to obtain such samples and are well documented in the art. "Vasa expression," as used herein, is used interchangeably with "vasa molecule expression," and refers to a vasa nucleic acid or a vasa peptide (including polypeptide and protein) expression. At the molecular level both PCR and Northern blotting can be used to determine the level of human vasa mRNA using products of this invention described earlier, and protocols well known in the art that are found in references which compile such methods. At the protein level, human vasa expression can be determined using either polyclonal anti-human vasa sera or monoclonal antibodies in combination with standard immunological assays. The preferred methods of the invention compare the measured level of human vasa expression of the test sample to a control having a known human vasa expression (e.g., to assess the presence or absence, or stage of a tumor of germ cell origin in a subject). A control human vasa expression can include a known amount of a nucleic acid probe, a human vasa epitope (such as a human vasa expression product), or a sample from the same tissue (fluid or aspirate) of a subject with a 'normal' (control) level of human vasa expression.

The invention also embraces methods of detecting tumors of germ cell origin. According to this aspect of the invention, the test sample can be of extragonadal (nongonadal) or gonadal tissue origin. When the test sample is of extragonadal tissue origin, the method involves detecting vasa expression in a test sample obtained from an extragonadal tissue of a subject. Vasa expression in the extragonadal test sample is indicative of the presence of a tumor of germ cell origin in the subject. The preferred methods of the invention compare the measured level of human vasa expression in the extragonadal test sample to the level of vasa expression in a control sample, preferably from the same extragonadal tissue of a 'normal' (control) subject. In general, extragonadal test samples from 'normal' subjects contain undetectable expression levels of a vasa molecules; test samples having detectable vasa expression levels are indicative of the presence of a tumor of germ cell origin in the subject.

When the test sample is obtained from a gonadal tissue of the subject (e.g., ovaries, testis, etc.), the method involves detecting vasa overexpression in the test sample, since vasa molecules are typically expressed at a baseline level corresponding to a 'normal' level in control gonadal tissues. Examination of gonadal tissue test samples typically involves examination of histologic samples (e.g., biopsy tissue slides). Histologic samples are commonly stained with agents that reveal tissue/cell morphology. Preferably, the skilled artisan selects histologic samples (e.g., from a gonadal tissue biopsy) that include tissue areas depicting both 'abnormal' and 'normal' morphologic appearance. The tissue areas with 'normal' appearance serve as an internal negative control (a preferred control). Alternatively, or additionally, gonadal tissues from 'normal' subjects can be used as a negative control. To detect the presence of a tumor of germ cell origin in gonadal tissue, the test samples are compared to the control samples (e.g., negative controls as discussed above or positive controls, i.e., samples of gonadal tissue having tumors of known germ cell origin) and vasa overexpression is determined. "Overexpression," as used in reference to a histologic test sample, refers to a statistically significant increase in vasa expression per unit surface area compared to a negative control sample. Therefore, vasa overexpression in the gonadal test sample as compared to a negative control sample, is indicative of the presence of a tumor of germ cell origin in the subject. In some embodiments, the subject has not previously been diagnosed as having a tumor of germ cell origin or a predisposition thereto (e.g., to detect a metastasis in a subject of previously undiagnosed cancer). In certain embodiments, the subject has a clinical diagnosis of a tumor of germ cell origin and the method is to confirm the clinical diagnosis, monitor remission of the tumor, or stage the tumor. In some embodiments, the tumor can be a testicular tumor (e.g., a seminoma), an ovarian tumor (e.g., a dysgerminoma or a teratoma), or a tumor of an extragonadal tissue (e.g., a mediastinal tumor or an intracranial tumor). In preferred embodiments, when the test sample examined is of gonadal origin, the method can further comprise detecting expression of a tumor-specific agent other than a vasa molecule (nucleic acid or polypeptide) in the test sample. Tumor-specific agents other than a vasa molecule include, but are not limited to, β-hCG, α-fetoprotein, placental-type alkaline phosphatase, prostate specific antigen, carcinoembryonic antigen, inhibin, epithelial membrane antigen, desmin, vimentin, GFAP-glial fibrillary acidic protein, synaptophysin, chromogranin, cytokeratin isoforms such as 7 and 20, and anti-keratin markers such as AE1/AE3 and CAM5.2.

According to another aspect, a method of subtyping tumors of germ cell origin is provided. The method involves detecting vasa expression in a test sample of a known or suspected germ cell origin tumor obtained from a subject. Vasa overexpression in the test sample as compared to a control is indicative of a seminoma in the subject, whereas absence of vasa expression in the test sample as compared to a control can be indicative of a nonseminoma in the subject. Nonseminomas include embryonal carcinoma, teratoma, choriocarcinoma, yolk sac tumor, or combinations of the foregoing. In certain embodiments, the subject has a tumor of mixed histologic appearance. In some embodiments, and preferably (but not exclusively) in the absence of vasa expression in the test sample, the method can further comprise detecting expression of a tumor-specific agent other than a vasa molecule in the test sample. Tumor-specific agents other than a vasa molecule are as described elsewhere herein.

According to another aspect, a method of distinguishing a tumor of germ cell origin from a non-germ cell tumor, is provided. The method involves detecting expression of a vasa molecule in a test sample, wherein expression of the vasa molecule is indicative of a tumor of a germ cell origin, and absence of expression of the vasa molecule is indicative of a non-germ cell tumor. In certain embodiments, the non-germ cell tumor resembles histologically a tumor of germ cell origin. Non-germ cell tumors include, but are not limited to, clear cell carcinoma of the ovary (can resemble dysgerminoma), a mediastinal thymoma, and a testicular lymphoma.

In preferred embodiments of the invention tumors aberrantly expressing human vasa can include: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; colorectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. Aberrant expression of a vasa molecule in all of the foregoing tumors is indicative that such tumors originated from cells of germ cell origin, which cells either through development or metastases became part of the tissue presently characterized as tumorous. In preferred embodiments, aberrant expression is overexpression of a human vasa molecule.

Human vasa polypeptides preferably are produced recombinantly, although such polypeptides may be isolated from biological extracts. Recombinantly produced human vasa polypeptides include chimeric proteins comprising a fusion of a human vasa protein with another polypeptide, e.g., a polypeptide capable of providing or enhancing protein—protein binding, sequence specific nucleic acid binding (such as GAL4), enhancing stability of the human vasa polypeptide under assay conditions, or providing a detectable moiety, such as green fluorescent protein. A polypeptide fused to a human vasa polypeptide or fragment may also provide means of readily detecting the fusion protein, e.g., by immunological recognition or by fluorescent labeling.

Detection may be effected in any convenient way for cell-based assays such as two- or three-hybrid screens. The transcript resulting from a reporter gene transcription assay of human vasa polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseseradish peroxidase, etc.). The label may be bound to a human vasa binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides human vasa-specific binding agents, methods of identifying and making such agents, and their use in diagnosis, therapy and pharmaceutical development. For example, human vasa-specific pharmacological agents are useful in a variety of diagnostic and therapeutic applications, especially where disease or disease prognosis is associated with altered human vasa binding characteristics. Novel human vasa-specific binding agents include human vasa-specific antibodies, cell surface receptors, and other natural intracellular and extracellular binding agents identified with assays such as two hybrid screens, and non-natural intracellular and extracellular binding agents identified in screens of chemical libraries and the like.

In general, the specificity of human vasa binding to a specific molecule is determined by binding equilibrium constants. Targets which are capable of selectively binding a human vasa polypeptide preferably have binding equilibrium constants of at least about $10^7$ $M^{-1}$, more preferably at least about $10^8M^{-1}$, and most preferably at least about $10^9M^{-1}$. The wide variety of cell based and cell free assays may be used to demonstrate human vasa-specific binding. Cell based assays include one, two and three hybrid screens, assays in which human vasa-mediated transcription is inhibited or increased, etc. Cell free assays include human vasa-protein binding assays, immunoassays, etc. Other assays useful for screening agents which bind human vasa polypeptides include fluorescence resonance energy transfer (FRET), and electrophoretic mobility shift analysis (EMSA).

According to a further aspect, a method for treating a tumor of germ cell origin in a subject, is provided. The method involves administering to a subject in need of such treatment an agent that inhibits vasa expression in a germ cell of the subject in an effective amount to inhibit vasa expression and inhibit the growth and/or proliferation of the tumor of germ cell origin in the subject. In a preferred embodiment, the agent is a vasa antisense nucleic acid. In certain embodiments, the method further comrises co-administering an anti-cancer agent.

Anti-cancer agents include, but are not limited to: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Podofilox; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride;

Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The vasa inhibitory agents of the invention (e.g., vasa antisense molecules, vasa binding molecules) are administered in effective amounts. An effective amount is a dosage of the vasa inhibitory agent sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, in connection with treating a tumor of germ cell origin in a subject, an effective amount is that amount which inhibits or reduces growth and/or proliferation of the tumor in the subject. Thus, it will be understood that the vasa inhibitory agents of the invention can be used to treat the above-noted conditions according to the preferred modes of administration described below. It is preferred generally that a maximum dose be used, that is, the highest safe dose according to sound medical judgment.

A subject, as used herein, refers to a human with a tumor of germ cell origin.

A vasa inhibitory agent of the invention may be administered alone or as part of a pharmaceutical composition. Such a pharmaceutical composition may include the vasa inhibitory agent in combination with any standard physiologically and/or pharmaceutically acceptable carriers which are known in the art. The compositions should be sterile and contain a therapeutically effective amount of the vasa inhibitory agent in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material, that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Parenteral vehicles include sodium chloride solution, Ringer's dextrose, dextrose and sodium chloride, lactated Ringer's or fixed oils.

Compositions suitable for parenteral administration conveniently comprise sterile aqueous and non-aqueous preparations of the vasa inhibitory agents of the invention. This aqueous preparation may be formulated according to known methods using suitable dispersing or wetting agents and suspending agents. Aqueous carriers include water, alcoholic/aqueous solutions, emulsions or suspensions, including saline and buffered media. Examples of non-aqueous solvents are propylene glycol, polyethylene glycol, vegetable oils such as olive oil, and injectable organic esters such as ethyl oleate, and including synthetic mono- or di-glycerides. The sterile injectable preparation also may be a sterile injectable solution or suspension in a non-toxic parenterally-acceptable diluent or solvent, for example, as a solution in 1,3-butane diol. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa. Preservatives and other additives may also be present such as, for example, antimicrobials, anti-oxidants, chelating agents, and inert gases and the like.

Parenteral administration routes are preferred according to the present invention. Any local parenteral administration that is medically acceptable, meaning any local administration that produces effective levels of the active compounds without causing clinically unacceptable adverse effects can be used to deliver agents of the invention. Delivery by injection into the affected gonadal tissue is preferred.

The pharmaceutical preparations, as described above, are administered in effective amounts. The effective amount will depend upon the mode of administration, the particular condition being treated and the desired outcome. It will also depend upon, as discussed above, the stage of the condition, the age and physical condition of the subject, the nature of concurrent therapy, if any, and like factors well known to the medical practitioner. For therapeutic applications, it is that amount sufficient to achieve a medically desirable result. In some cases this is a decrease in germ cell growth and/or proliferation.

Generally, doses of active compounds of the present invention would be from about 0.01 mg/kg per day to 1000 mg/kg per day. It is expected that doses ranging from 50–500 mg/kg will be suitable.

The pharmaceutical compositions may conveniently be presented in unit dosage form and may be prepared by any of the methods well-known in the art of pharmacy. All methods include the step of bringing the vasa inhibitory agents of the invention into association with a carrier which constitutes one or more accessory ingredients. In general, the compositions are prepared by uniformly and intimately bringing the vasa inhibitory agents into association with a liquid carrier, a finely divided solid carrier, or both, and then, if necessary, shaping the product.

Compositions suitable for parenteral administration (e.g., by direct/local injection) include suspensions in aqueous liquids or non-aqueous liquids such as a syrup, elixir or an emulsion.

Other delivery systems can include time-release, delayed release or sustained release delivery systems. Such systems can avoid repeated administrations of the vasa inhibitory agents of the invention, increasing convenience to the subject and the physician. Many types of release delivery systems are available and known to those of ordinary skill in the art. They include the above-described polymeric systems, as well as polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include nonpolymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the vasa inhibitory agent is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The vasa inhibitory agents of the invention may be administered alone or in combination (co-administered) with the above-described drug therapies by any conventional route, including injection, repeated injection, topical application, etc., over time. The administration may, for example, be oral, intraperitoneal, intramuscular, intra-cavity, subcutaneous, intravenous or transdermal for the co-administered anti-cancer agent. When using the vasa inhibitory agents of the invention, direct administration to the affected site (e.g., ovaries, testis, etc.) such as administration by injection, is preferred.

The term "co-administered," means administered substantially simultaneously with another anti-cancer agent. By substantially simultaneously, it is meant that a vasa inhibitory agent of the invention is administered to the subject close enough in time with the administration of the anti-cancer agent. The anti-cancer agent may be present in a different formulation than the vasa inhibitory agent of the invention, or it may be part of the same formulation (and therefore be administered locally together with the agent of the invention).

The co-administered agent can act cooperatively, additively or synergistically with a vasa inhibitory agent of the invention to produce a desired effect, for example, inhibition of the tumor of germ cell origin. Since germ cells are relatively 'dispensible' (i.e., necessary for reproduction but not necessary for survival), as long as the agent is delivered to the gonads, normal (nontumorous) germ cells can also be targeted with the therapeutic agents of the invention. The anticancer agent is administered in effective amounts. Such amounts maybe less than these sufficient to provide a therapeutic benefit when the agent is administered alone and not in combination with a vasa inhibitory agent of the invention. A person of ordinary skill in the art would be able to determine the effective amounts needed.

The invention will be more fully understood by reference to the following examples. These examples, however, are merely intended to illustrate the embodiments of the invention and are not to be construed to limit the scope of the invention.

EXAMPLES

Example 1

Cloning of Human Vasa Gene

Expressed sequence tags (EST's) corresponding to the human vasa gene were identified in a publically available database maintained by the National Center for Biotechnology Information (NCBI) using the BLAST program. The DNA sequence corresponding to the mouse vasa cDNA (Genbank accession #2500525) was the query sequence; default search parameters were employed. Several EST's (zt93a07.sl-Genbank# AA399611; zt93a07.rl-Genbank #AA398976; qf47dll.x-Genbank #AI217144) corresponding to the 3' end of the human vasa gene were identified. These appeared to be bona fide human vasa EST's based on the extent of sequence conservation and the fact that all were derived from a testis source, consistent with germ cell origin. A 28-mer oligonucleotide corresponding to the 3' untranslated region was designed nad synthesized (5'-CTC TGC ATC AAA ACC ACA GAC TTG AAG G-3', SEQ ID NO:8). This oligonucleotide was then used in a 5' RACE (rapid amplification of cDNA ends) reaction to obtain a human vasa cDNA. Marathon-Ready human testis cDNA was obtained from CLONTECH and 5' RACE was performed as per the manufacturer's instructions, except that LA Taq (TAKARA) was utilized to minimize errors during PCR. A single main reaction product consisting of a 2.2 kilobase DNA fragment was obtained, purified by agarose gel electrophoresis, and subcloned into a commercially available cloning vector (pCR2.1, INVITROGEN) to yield plasmid pVAS3. The nucleotide sequence of the human vasa cDNA was obtained by double-stranded DNA sequencing; both strands were sequenced. The sequence of the human vasa protein (SEQ ID NO:2) was determined by conceptual translation of the cDNA sequence (SEQ ID NO:1).

Example 2

Preparation and Testing of Antibodies Selective for a Vasa Protein

Regions likely to be antigenic were identified by an algorithm for antigencity (University of Wisconsin Genetics Computer Group Software). Two regions were selected for peptide synthesis: (1) CEDNPTRNRGFSKRGGYRDGNNSEASGPYR, SEQ ID NO:9 (amino acids 117–146 of SEQ ID NO:2); and (2) VDTRKGKSTLNTAGFSSSRAPNPVDDESW, SEQ ID NO:10 (amino acids 695–723 of SEQ ID NO:2). As an alternative approach to generating antigen, the N-terminus of the vasa polypeptide (amino acids 1–318 of SEQ ID NO:2), which is believed to be highly antigenic, was expressed in *E. coli*. PCR was performed on pVAS3 with the primers 5'-AAG TCA CCA TGG GGG ATG AA-3', SEQ ID NO:11 (designed around a naturally occuring Ncol site) and 5'-TTA AGA TCT TTT TTG CAC AGG AGT AAG C-3', SEQ ID NO:12 (which contains an engineering BglII site). The product was digested with the restriction enzymes NcoI and BglII and ligated in the expression vector PQE-60 (QIAGEN) linearized with NcoI and BglII (directional cloning). This results in an in-frame expression construct where the first amino acid of the expressed protein corresponds to the native methionine and the C-terminus is fused to six consecutive histidines encoded by the vector (for protein purification). Following expression in *E. coli* and affinity purification of the protein according to the manufacturer's instructions, the expressed protein was used to immunize animals according to methods known to one of ordinary skill in the art.

Anti-vasa antibodies were prepared and tested for selectivity for the vasa protein using conventional immunohisto- and immunocyto- chemistry methods adapted to include the vasa protein (or fragment thereof) as a positive control and a non-vasa protein (lacking sequence homology to vasa protein) as a negative control. Additional controls (e.g., negative controls containing nongonadal tissue, tumors of non-germ cell origin), can be included in the assay to establish the specificity of the antibodies for detecting tumors of germ cell origin in a complex sample.

The preferred assays for tissue samples are performed on formalin-fixed, paraffin-embedded tissue following antigen retrieval as routinely done on clinical material in a hospital pathology laboratory setting. Exemplary samples (including positive and negative controls) include: normal testes and ovaries, other normal tissues, a range of major tumor types (to evaluate specificity) and germ cell tumors of various histologic subtypes and anatomic locations (to establish clinical utility for detecting these tumors). Preliminary results confirmed the predicted cytoplasmic immunoreactivity in germ cells with an appropriate negative result obtained for the preimmune control.

In a further example, the specificity of anti-human vasa antibodies for testicular germ cell tumors was also confirmed using immunohistochemical stains. Granulosa cell tumor (non-germ cell tumor of the ovary-negative control) showed no positive stain. By contrast, classic seminoma (testis) showed strong positive reaction (appearing as brown stain) only in tumor cells and not in the surrounding stroma. Permatocytic seminoma (testis) also showed strong positive reaction in in all tumor cells. For this particular experiment, sections were incubated with a 1:1000 dilution of affinity-purified polyclonal anti-vasa antibody. Detection was performed as described elsewhere herein using diaminobenzidine as the chromogen. Slides were counterstained with hematoxylin.

Example 3

Detection of a Vasa Protein by Immunoassay

Vasa protein (peptide and/or polypeptide) detection is carried out by the indirect enzyme-linked immunosorbent assay (ELISA). Such assays are well known in the art. Briefly, ninety six-well microtiter plates (Dynatech Laboratories, Alexandria, Va.) are coated with, for example, serum, germ cell tumor culture supernatants, germ cell tumor lysates/extracts, etc., and left overnight at 4° C. The plates were then washed 3 times with PBS containing 0.05% Tween-20 and blocked with 5% dry milk for 2 hrs at 37° C. The plates are washed and incubated again overnight at 4° C. with polyclonal vasa antisera or vasa monoclonal antibodies as described earlier (diluted 1:100–1:107 in PBS with 1% dry milk). The plates are washed, and 100 $\mu$l of peroxidase-conjugated goat anti-mouse (or anti-animal used to generate antibodies/sera) IgG (Kirkegaard & Perry Laboratories, Inc., Gaithersburg, Md.) at 1:2,000 dilution in PBS with 0.05% Tween-20 and 1% dry milk, are added. The plates are incubated for 2 hrs at 37° C. The plates are then washed 3 times with PBS containing 0.05% Tween-20. Then, 100 $\mu$l of O-phenylenediamine (0.4 mg/ml in citrate phosphate buffer containing 0.015% hydrogen peroxide; Sigma Chemical Co. St Louis, Mo.), are added to each well, and the reaction is stopped by the addition of 2.5N HCl. After 15 minutes the optical density at 492 nm ($OD_{492}$) is measured using a EL308 ELISA reader (Bio-Tek Instruments, Winooski, Vt.). The titer expressed in $OD_{492}$ unit is calculated as a multiple of the dilution in the linear portion of a standard plot.

Example 4

Detection of Vasa Nucleic Acid by PCR Amplification

An exemplary procedure for PCR amplification to detect a tumor marker is provided in U.S. Pat. No. 5,688,648, entitled, “Methods of detecting micrometastasis of prostate cancer”, issued to C. Croce, et al. It is to be understood that the exemplary procedures described therein can be modified by one of ordinary skill in the art using no more that routine experimentation to detect the vasa molecule in any type of sample material using the novel reagents disclosed herein.

Vasa protein expression is detected by determining whether mRNA for the vasa protein is present in a sample. The preferred procedure for detecting mRNA for vasa protein is by PCR amplification.

Synthetic oligonucleotides: 5'-TGC ATC AAA ACC ACA GAC TTG-3', SEQ ID NO:13, and 5'-AAT GCC ATC AAA GGA ACA GC-3', SEQ ID NO:14, were designed using the Primer3 program (Whitehead Institute for Biomedical Research) for an RT-PCR assay of vasa mRNA expression. RT-PCR was performed using the Superscript One-Step PCR kit (GIBCO) per the manufacturer's instructions. When RT-PCR was performed on total human testis RNA, a single product of expected size (804 bp) was consistently detected. However, no products were detected with RNA from extragonadal sources (e.g., liver), confirming the specificity of the assay.

Example 5

Detection of Vasa Molecules in Tumor Test Samples

An exemplary procedure for detecting a tumor marker in a breast tumor tissue sample or extract is provided in U.S. Pat. No. 5,723,302, entitled, “Detection of prostrate-specific antigen in breast tumors”, issued to E. Diamandis. An exemplary procedure for detecting a tumor marker in a blood sample is provided in U.S. Pat. No. 5,935,775, entitled, “Whole blood analysis of prostate specific antigen spotted on a solid support”, issued to G. Savjani. It is to be understood that these exemplary procedures can be modified by one of ordinary skill in the art using no more that routine experimentation to detect the vasa molecule in any type of sample using the novel reagents disclosed herein.

Sample Preparation.

(1) Solid tissue/tumor samples: A tumor sample or intact tissue is prepared in accordance with standard histological procedures and analyzed by, e.g., in situ immunohistochemistry, enzyme immunoassay (to detect vasa protein), or by, e.g., nucleic acid enrichment (to detect a vasa nucleic acid). Immunoassays are performed as described above (Example 3) using the anti-vasa protein antibodies that selectively bind to the vasa protein or peptides. Nucleic acid assays are performed as described above (Example 4) for detection of a vasa nucleic acid, e.g., by PCR amplification. Total RNA or mRNA is isolated from the tumor samples and cDNA synthesized by reverse transcription. PCR amplification of cDNA is accomplished using vasa specific primers also as described above. A probe is used to detect cDNA for vasa. Other methods for detecting an RNA for vasa may also be used, such as, the northern blot technique.

(2) Blood samples: Blood samples can be used directly in liquid form, dried onto a solid support (see, e.g., U.S. Pat. No. 5,935,775), or can be further processed in accordance with standard procedures known to those of ordinary skill in the art for use in the assays of the invention. For example, the sera can be separated into fractions prior to analysis for the presence of a vasa molecule.

Analysis.

It is anticipated that the presence of a vasa molecule in a tumor sample of a subject is diagnostic of the presence of a tumor of germ cell origin in the subject. To validate the detection methods disclosed herein for predicting a tumor of germ cell origin, samples of known pathology are assayed to determine the presence or absence of a vasa molecule and the presence or absence of the vasa molecule is correlated to the presence or absence of a tumor of germ cell origin in known samples of positive controls (tumor present) and negative controls (tumor absent), respectively. Additional internal assay controls can be used to verify assay reproducibility (e.g., analysis of known sample components, such as other known, is protein or other known nucleic acid components in the tissue from which the sample is derived, e.g., β-hCG, c-fetoprotein, placental-type alkaline phosphatase, prostate specific antigen, carcinoembryonic antigen, inhibin, epithelial membrane antigen, desmin, vimentin, GFAP-glial fibrillary acidic protein, synaptophysin, chromogranin, cytokeratin isoforms such as 7 and 20, anti-keratin markers such as AE1/AE3 and CAM5.2, etc.). A statistically significant, positive correlation is established between the presence of a vasa molecule and the presence of a tumor of germ cell origin. A statistically significnt positive correlation also is established between the relative amount of the vasa molecule present in the sample (e.g., of gonadal origin) of a subject, and the stage and/or size of the subject's tumor, as well as the degree of metastasis in the subject. This correlation is used to evaluate patient response to treatment modalities, monitor tumor regression and/or remission, and/or to predict patient survival.

TABLE I

| Sequences with partial homologies to human vasa Sequences with GenBank accession numbers: | |
|---|---|
| S75275 | (SEQ ID NO: 16), |
| D14859 | (SEQ ID NO: 17), |
| AB005147 | (SEQ ID NO: 18), |
| Y12007 | (SEQ ID NO: 19), |
| AF046043 | (SEQ ID NO: 20), |
| Z81449.1 | (SEQ ID NO: 21), |
| X81823 | (SEQ ID NO: 22), |
| P09052 | (SEQ ID NO: 23), |
| Q64060 | (SEQ ID NO: 24), |
| Q61496 | (SEQ ID NO: 25), |
| Q62167 | (SEQ ID NO: 26), |
| O00571 | (SEQ ID NO: 27), |
| P24346 | (SEQ ID NO: 28), |
| P16381 | (SEQ ID NO: 29), |
| O15523 | (SEQ ID NO: 30), |
| AL042306 | (SEQ ID NO: 31), |
| AA399611 | (SEQ ID NO: 32), |
| AA398976 | (SEQ ID NO: 33), |
| AA383535 | (SEQ ID NO: 34), |
| AI217144 | (SEQ ID NO: 35), |
| AI953070 | (SEQ ID NO: 36), |
| AI025074 | (SEQ ID NO: 37), |
| AI654417 | (SEQ ID NO: 38), |
| AI337133 | (SEQ ID NO: 39), |
| AA758412 | (SEQ ID NO: 40), |
| AI969018 | (SEQ ID NO: 41), |
| AA400066 | (SEQ ID NO: 42), |
| AA862553 | (SEQ ID NO: 43), |
| AA401568 | (SEQ ID NO: 44), |
| AA316798 | (SEQ ID NO: 45), |
| T85890 | (SEQ ID NO: 46), |
| T82153 | (SEQ ID NO: 47). |

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is presented below and is followed by a sequence listing.

We claim:

1. An isolated nucleic acid molecule selected from the group consisting of:

(a) nucleic acid molecules which hybridize under stringent conditions to a molecule consisting of a nucleotide sequence set forth as SEQ ID NO:1 and which code for a human vasa polypeptide, wherein the stringent conditions are: (1) hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA), wherein SSC is 0.15 M sodium chloride/0.015 M sodium citrate, pH7; SDS is sodium dodecyl sulphate; and EDTA is ethylenediaminetetracetic acid, and (2) washing in 2×SSC at room temperature and washing in 0.1×SSC/0.1 SDS at 68° C., (b) nucleic acid molecules that differ from the nucleic acid molecules of (a) in codon sequence due to the degeneracy of the genetic code, or (c) full-length complements of (a) or (b).

2. The isolated nucleic acid molecule of claim 1, wherein the isolated nucleic acid molecule comprises the nucleotide sequence set forth as SEQ NO: 1.

3. The isolated nucleic acid molecule of claim 1, wherein the isolated nucleic acid molecule consists of the nucleotide sequence set forth as SEQ ID NO:15.

4. A kit comprising a package containing an isolated nucleic acid molecule of claim 1.

* * * * *

UNITED STATES PATENT AND TRADEMARK OFFICE

CERTIFICATE OF CORRECTION

PATENT NO. : 6,875,854 B1
DATED : April 5, 2005
INVENTOR(S) : Diego H. Castrillon It is certified that error appears in the above-identified patent and that said Letters Patent is hereby corrected as shown below:

Column 140,
Line 45, should read as shown below:
-- sequence set forth as SEQ ID NO: 1. --

Signed and Sealed this

Thirty-first Day of May, 2005

JON W. DUDAS
*Director of the United States Patent and Trademark Office*

SEQUENCE LISTING

```
<160> NUMBER OF SEQ ID NOS: 47

<210> SEQ ID NO 1
<211> LENGTH: 2224
<212> TYPE: DNA
<213> ORGANISM: Homo sapiens

<400> SEQUENCE: 1

acttgaagtc accatggggg atgaagattg ggaagcagaa atcaaccctc atatgtcttc      60

ctatgttccc atatttgaga aggataggta ttctggagaa aatggagaca attttaacag     120

gactccagct tcatcatcag aaatggatga tggaccttct cgaagagatc atttcatgaa     180

aagtggattt gcctctgggc ggaattttgg aaacagagat gctggtgagt gtaataagcg     240

agataataca tccacaatgg gtggttttgg agttggaaag agttttggaa acagaggttt     300

ttcaaacagc aggtttgaag atggtgatag ctctggtttc tggagagagt ctagtaatga     360

ctgcgaagat aatccaacac ggaacagagg gttttccaag agaggcggct atcgagatgg     420

aaataattca gaagcttcag ggccatacag aagaggtgga agaggtagtt tccgaggttg     480

ccgtggagga tttggtctag gaagtccaaa taatgactta gacccagacg aatgtatgca     540
```

```
gcgcactggt ggccttttg gttctagaag accagtatta agtggcacag gtaatggtga    600
tacttctcaa agcagaagtg gcagtggaag tgaacgaggt ggttacaaag gtttaaatga    660
agaagtaata acaggctctg gaaagaattc ttggaagtca gaagcagaag gaggagaaag    720
tagtgatact caaggaccaa aagtgaccta catacccct cctccacctg aggatgagga    780
ctccatcttt gcacattatc agacaggcat aaacttcgac aaatacgaca ctattcttgt    840
ggaagtgtct ggacatgatg caccaccagc aattctgact tttgaagaag ctaatctctg    900
tcagacactg aataacaaca ttgctaaagc tggttatact aagcttactc ctgtgcaaaa    960
atacagtatt cctatcatac ttgcaggacg agatttgatg gcttgtgctc aaacagggtc   1020
tgggaagact gcggcttttc tcctaccaat tttggctcat atgatgcatg atggaataac   1080
tgccagtcgt tttaaagagt tgcaggaacc agagtgtatt attgtagcac caactcgaga   1140
attggtcaac cagatttatt tggaagccag aaaatttct tttgggactt gtgtaagagc   1200
tgttgttata tatgggggaa cccagctggg acattcaatt cgacaaatag tacaaggctg   1260
taatatatta tgtgctactc ctggaagact gatggatatc ataggcaaag aaaagattgg   1320
tctcaaacag atcaaatact tagttttgga tgaagctgat cgcatgttgg atatgggttt   1380
tggtccagaa atgaagaagt taatttcttg cccaggaatg ccatcaaagg aacagcgcca   1440
aacccttatg ttcagtgcaa cttttccaga ggaaattcaa aggttggctg cagagttttt   1500
aaagtcaaat tatctgtttg ttgctgttgg acaagtgggt ggagcatgta gagatgttca   1560
gcagaccgtt ctccaagttg gccagttctc aaaaagagaa aagctcgttg aaattctgcg   1620
aaacataggg gatgaaagaa ctatggtctt tgttgaaact aagaaaaaag cagattttac   1680
tgcaactttt ctttgtcaag aaaaaatatc aactacaagt atccatggtg atcgggaaca   1740
gagagagcgg gagcaagctc ttggagattt tcgctttgga aagtgcccag ttcttgttgc   1800
tacttcagta gctgccagag ggctggatat tgaaaatgtg caacatgtta tcaattttga   1860
tcttccttct accattgatg aatatgttca tcgaattggg cgtactggtc gttgtgggaa   1920
tactggcaga gcaatttcct tttttgatct tgaatcggat aaccatttag cacagcctct   1980
agtaaaagta ttgacagatg ctcaacagga tgttcctgca tggttggaag aaattgcctt   2040
tagtacatac attcctggct tcagtggtag tacaagagga aacgtgtttg catcagttga   2100
taccagaaag ggcaagagca ctttgaacac agctgggttt tcttcttcac gagctcccaa   2160
tccagtagat gatgagtcat gggattaaag ccaaaacatc cttcaagtct gtggttttga   2220
tgca                                                                2224
```

<210> SEQ ID NO 2
<211> LENGTH: 724
<212> TYPE: PRT
<213> ORGANISM: Homo sapiens

<400> SEQUENCE: 2

```
Met Gly Asp Glu Asp Trp Glu Ala Glu Ile Asn Pro His Met Ser Ser
1               5                   10                  15

Tyr Val Pro Ile Phe Glu Lys Asp Arg Tyr Ser Gly Glu Asn Gly Asp
            20                  25                  30

Asn Phe Asn Arg Thr Pro Ala Ser Ser Ser Glu Met Asp Asp Gly Pro
        35                  40                  45

Ser Arg Arg Asp His Phe Met Lys Ser Gly Phe Ala Ser Gly Arg Asn
    50                  55                  60
```

-continued

```
Phe Gly Asn Arg Asp Ala Gly Glu Cys Asn Lys Arg Asp Asn Thr Ser
65                  70                  75                  80

Thr Met Gly Gly Phe Gly Val Gly Lys Ser Phe Gly Asn Arg Gly Phe
                85                  90                  95

Ser Asn Ser Arg Phe Glu Asp Gly Asp Ser Ser Gly Phe Trp Arg Glu
            100                 105                 110

Ser Ser Asn Asp Cys Glu Asp Asn Pro Thr Arg Asn Arg Gly Phe Ser
        115                 120                 125

Lys Arg Gly Gly Tyr Arg Asp Gly Asn Asn Ser Glu Ala Ser Gly Pro
    130                 135                 140

Tyr Arg Arg Gly Gly Arg Gly Ser Phe Arg Gly Cys Arg Gly Gly Phe
145                 150                 155                 160

Gly Leu Gly Ser Pro Asn Asn Asp Leu Asp Pro Asp Glu Cys Met Gln
                165                 170                 175

Arg Thr Gly Gly Leu Phe Gly Ser Arg Arg Pro Val Leu Ser Gly Thr
            180                 185                 190

Gly Asn Gly Asp Thr Ser Gln Ser Arg Ser Gly Ser Gly Ser Glu Arg
        195                 200                 205

Gly Gly Tyr Lys Gly Leu Asn Glu Glu Val Ile Thr Gly Ser Gly Lys
    210                 215                 220

Asn Ser Trp Lys Ser Glu Ala Glu Gly Gly Glu Ser Ser Asp Thr Gln
225                 230                 235                 240

Gly Pro Lys Val Thr Tyr Ile Pro Pro Pro Pro Pro Glu Asp Glu Asp
                245                 250                 255

Ser Ile Phe Ala His Tyr Gln Thr Gly Ile Asn Phe Asp Lys Tyr Asp
            260                 265                 270

Thr Ile Leu Val Glu Val Ser Gly His Asp Ala Pro Pro Ala Ile Leu
        275                 280                 285

Thr Phe Glu Glu Ala Asn Leu Cys Gln Thr Leu Asn Asn Asn Ile Ala
    290                 295                 300

Lys Ala Gly Tyr Thr Lys Leu Thr Pro Val Gln Lys Tyr Ser Ile Pro
305                 310                 315                 320

Ile Ile Leu Ala Gly Arg Asp Leu Met Ala Cys Ala Gln Thr Gly Ser
                325                 330                 335

Gly Lys Thr Ala Ala Phe Leu Leu Pro Ile Leu Ala His Met Met His
            340                 345                 350

Asp Gly Ile Thr Ala Ser Arg Phe Lys Glu Leu Gln Glu Pro Glu Cys
        355                 360                 365

Ile Ile Val Ala Pro Thr Arg Glu Leu Val Asn Gln Ile Tyr Leu Glu
    370                 375                 380

Ala Arg Lys Phe Ser Phe Gly Thr Cys Val Arg Ala Val Val Ile Tyr
385                 390                 395                 400

Gly Gly Thr Gln Leu Gly His Ser Ile Arg Gln Ile Val Gln Gly Cys
                405                 410                 415

Asn Ile Leu Cys Ala Thr Pro Gly Arg Leu Met Asp Ile Ile Gly Lys
            420                 425                 430

Glu Lys Ile Gly Leu Lys Gln Ile Lys Tyr Leu Val Leu Asp Glu Ala
        435                 440                 445

Asp Arg Met Leu Asp Met Gly Phe Gly Pro Glu Met Lys Lys Leu Ile
    450                 455                 460

Ser Cys Pro Gly Met Pro Ser Lys Glu Gln Arg Gln Thr Leu Met Phe
465                 470                 475                 480

Ser Ala Thr Phe Pro Glu Glu Ile Gln Arg Leu Ala Ala Glu Phe Leu
```

```
                485                 490                 495

Lys Ser Asn Tyr Leu Phe Val Ala Val Gly Gln Val Gly Gly Ala Cys
            500                 505                 510

Arg Asp Val Gln Gln Thr Val Leu Gln Val Gly Gln Phe Ser Lys Arg
        515                 520                 525

Glu Lys Leu Val Glu Ile Leu Arg Asn Ile Gly Asp Glu Arg Thr Met
    530                 535                 540

Val Phe Val Glu Thr Lys Lys Lys Ala Asp Phe Thr Ala Thr Phe Leu
545                 550                 555                 560

Cys Gln Glu Lys Ile Ser Thr Thr Ser Ile His Gly Asp Arg Glu Gln
                565                 570                 575

Arg Glu Arg Glu Gln Ala Leu Gly Asp Phe Arg Phe Gly Lys Cys Pro
            580                 585                 590

Val Leu Val Ala Thr Ser Val Ala Ala Arg Gly Leu Asp Ile Glu Asn
        595                 600                 605

Val Gln His Val Ile Asn Phe Asp Leu Pro Ser Thr Ile Asp Glu Tyr
    610                 615                 620

Val His Arg Ile Gly Arg Thr Gly Arg Cys Gly Asn Thr Gly Arg Ala
625                 630                 635                 640

Ile Ser Phe Phe Asp Leu Glu Ser Asp Asn His Leu Ala Gln Pro Leu
                645                 650                 655

Val Lys Val Leu Thr Asp Ala Gln Gln Asp Val Pro Ala Trp Leu Glu
            660                 665                 670

Glu Ile Ala Phe Ser Thr Tyr Ile Pro Gly Phe Ser Gly Ser Thr Arg
        675                 680                 685

Gly Asn Val Phe Ala Ser Val Asp Thr Arg Lys Gly Lys Ser Thr Leu
    690                 695                 700

Asn Thr Ala Gly Phe Ser Ser Ser Arg Ala Pro Asn Pro Val Asp Asp
705                 710                 715                 720

Glu Ser Trp Asp


<210> SEQ ID NO 3
<211> LENGTH: 722
<212> TYPE: PRT
<213> ORGANISM: Mus musculus

<400> SEQUENCE: 3

Met Gly Asp Glu Asp Trp Glu Ala Glu Ile Leu Lys Pro His Val Ser
1               5                   10                  15

Ser Tyr Val Pro Val Phe Glu Lys Asp Lys Tyr Ser Ser Gly Ala Asn
            20                  25                  30

Gly Asp Thr Phe Asn Arg Thr Ser Ala Ser Ser Glu Met Glu Asp Gly
        35                  40                  45

Pro Ser Gly Arg Asp Asp Phe Met Arg Ser Gly Phe Pro Ser Gly Arg
    50                  55                  60

Ser Leu Gly Ser Arg Asp Ile Gly Glu Ser Ser Lys Lys Glu Asn Thr
65                  70                  75                  80

Ser Thr Thr Gly Gly Phe Gly Arg Gly Lys Gly Phe Gly Asn Arg Gly
                85                  90                  95

Phe Leu Asn Asn Lys Phe Glu Glu Gly Asp Ser Ser Gly Phe Trp Lys
            100                 105                 110

Glu Ser Asn Asn Asp Cys Glu Asp Asn Gln Thr Arg Ser Arg Gly Phe
        115                 120                 125

Ser Lys Arg Gly Gly Cys Gln Asp Gly Asn Asp Ser Glu Ala Ser Gly
```

-continued

```
    130                 135                 140

Pro Phe Arg Arg Gly Gly Arg Gly Ser Phe Arg Gly Cys Arg Gly Gly
145                 150                 155                 160

Phe Gly Leu Gly Arg Pro Asn Ser Glu Ser Asp Gln Asp Gln Gly Thr
                165                 170                 175

Gln Cys Gly Gly Gly Phe Leu Val Leu Gly Lys Pro Ala Ala Ser Asp
            180                 185                 190

Ser Gly Asn Gly Asp Thr Tyr Gln Ser Arg Ser Gly Ser Gly Arg Gly
        195                 200                 205

Gly Tyr Lys Gly Leu Asn Glu Glu Val Val Thr Gly Ser Gly Lys Asn
    210                 215                 220

Ser Trp Lys Ser Glu Thr Glu Gly Gly Glu Ser Ser Asp Ser Gln Gly
225                 230                 235                 240

Pro Lys Val Thr Tyr Ile Pro Pro Pro Pro Pro Glu Asp Glu Asp Ser
                245                 250                 255

Ile Phe Ala His Tyr Gln Thr Gly Ile Asn Phe Asp Lys Tyr Asp Thr
            260                 265                 270

Ile Leu Val Glu Val Ser Gly His Asp Ala Pro Pro Ala Ile Leu Thr
        275                 280                 285

Phe Glu Glu Ala Asn Leu Cys Gln Thr Leu Asn Asn Asn Ile Arg Lys
    290                 295                 300

Ala Gly Tyr Thr Lys Leu Thr Pro Val Gln Lys Tyr Thr Ile Pro Ile
305                 310                 315                 320

Val Leu Ala Gly Arg Asp Leu Met Ala Cys Ala Gln Thr Gly Ser Gly
                325                 330                 335

Lys Thr Ala Ala Phe Leu Leu Pro Ile Leu Ala His Met Met Arg Asp
            340                 345                 350

Gly Ile Thr Ala Ser Arg Phe Lys Glu Leu Gln Glu Pro Glu Cys Ile
        355                 360                 365

Ile Val Ala Pro Thr Arg Glu Leu Ile Asn Gln Ile Tyr Leu Glu Ala
    370                 375                 380

Arg Lys Phe Ser Phe Gly Thr Cys Val Ile Ser Val Val Ile Tyr Gly
385                 390                 395                 400

Gly Thr Gln Phe Gly His Ser Val Arg Gln Ile Val Gln Gly Cys Asn
                405                 410                 415

Ile Leu Cys Ala Thr Pro Gly Arg Leu Met Asp Ile Ile Gly Lys Glu
            420                 425                 430

Lys Ile Gly Leu Lys Gln Val Lys Tyr Leu Val Leu Asp Glu Ala Asp
        435                 440                 445

Ser Met Leu Asp Met Gly Phe Ala Pro Glu Ile Lys Lys Leu Ile Ser
    450                 455                 460

Cys Pro Gly Met Pro Ser Lys Glu Gln His Gln Thr Leu Leu Phe Ser
465                 470                 475                 480

Ala Thr Phe Pro Glu Glu Ile Gln Arg Leu Ala Gly Asp Phe Leu Lys
                485                 490                 495

Ser Asn Tyr Leu Phe Val Ala Val Gly Gln Val Gly Gly Ala Cys Arg
            500                 505                 510

Asp Val Gln Gln Thr Ile Leu Gln Val Gly Gln Tyr Gln Lys Glu Lys
        515                 520                 525

Ser Leu Leu Arg Phe Tyr Glu Asn Ile Gly Asp Glu Arg Thr Met Val
    530                 535                 540

Phe Val Glu Thr Lys Lys Lys Ala Asp Phe Ile Ala Thr Phe Leu Cys
545                 550                 555                 560
```

```
Gln Glu Lys Ile Ser Ser Thr Ser Ile His Gly Asp Arg Glu Gln Arg
                565                 570                 575

Glu Arg Glu Gln Ala Leu Gly Asp Phe Arg Cys Gly Lys Cys Pro Val
            580                 585                 590

Leu Val Ala Thr Ser Val Ala Ala Arg Gly Leu Asp Ile Glu Asn Val
        595                 600                 605

Gln His Val Ile Asn Phe Asp Leu Pro Ser Thr Ile Asp Glu Tyr Val
    610                 615                 620

His Arg Ile Gly Arg Thr Gly Arg Cys Gly Asn Thr Gly Arg Ala Ile
625                 630                 635                 640

Ser Phe Phe Asp Thr Asp Ser Asp Asn His Leu Ala Gln Pro Leu Val
                645                 650                 655

Lys Val Leu Ser Asp Ala Gln Gln Asp Val Pro Ala Trp Leu Glu Glu
            660                 665                 670

Ile Ala Phe Ser Thr Tyr Val Pro Pro Ser Phe Ser Ser Ser Thr Arg
        675                 680                 685

Gly Gly Ala Val Phe Ala Ser Val Asp Thr Arg Lys Asn Tyr Gln Gly
    690                 695                 700

Lys Ala His Val Glu Tyr Ser Gly Asp Phe Phe Phe Thr Ser Ser Gln
705                 710                 715                 720

Ser Ser


<210> SEQ ID NO 4
<211> LENGTH: 713
<212> TYPE: PRT
<213> ORGANISM: Rattus norvegicus

<400> SEQUENCE: 4

Met Gly Asp Glu Asp Trp Glu Ala Glu Ile Leu Lys Pro His Val Ser
1               5                   10                  15

Ser Tyr Val Pro Val Phe Glu Lys Asp Lys Tyr Ser Ser Gly Ala Asn
            20                  25                  30

Gly Asp Thr Phe Asn Arg Thr Ser Ala Ser Ser Ser Glu Met Glu Asp
        35                  40                  45

Gly Pro Ser Gly Arg Asp His Phe Met Arg Ser Gly Phe Ser Ser Gly
    50                  55                  60

Arg Asn Leu Gly Asn Arg Asp Ile Gly Glu Ser Ser Lys Arg Glu Thr
65                  70                  75                  80

Thr Ser Thr Thr Gly Gly Phe Gly Arg Gly Lys Gly Phe Gly Asn Arg
                85                  90                  95

Gly Phe Leu Asn Asn Lys Phe Glu Glu Gly Asp Ser Ser Gly Phe Trp
            100                 105                 110

Lys Glu Ser Thr Asn Asp Cys Glu Asp Thr Gln Thr Arg Ser Arg Gly
        115                 120                 125

Phe Ser Lys Arg Gly Gly Tyr Pro Asp Gly Asn Asp Ser Glu Ala Ser
    130                 135                 140

Gly Pro Phe Arg Arg Gly Gly Arg Asp Ser Glu Tyr Asp Gln Asp Gln
145                 150                 155                 160

Gly Ser Gln Arg Gly Gly Gly Leu Phe Gly Ser Arg Lys Pro Ala Ala
                165                 170                 175

Ser Asp Ser Gly Ser Gly Asp Thr Phe Gln Ser Arg Ser Gly Asn Ala
            180                 185                 190

Arg Gly Ala Tyr Lys Gly Leu Asn Glu Glu Val Val Thr Gly Ser Gly
        195                 200                 205
```

-continued

```
Lys Asn Ser Trp Lys Ser Glu Ala Glu Gly Gly Glu Ser Ser Asp Ile
    210                 215                 220

Gln Gly Pro Lys Val Thr Tyr Ile Pro Pro Pro Pro Pro Glu Asp Glu
225                 230                 235                 240

Asp Ser Ile Phe Ala His Tyr Gln Thr Gly Ile Asn Phe Asp Lys Tyr
                245                 250                 255

Asp Thr Ile Leu Val Glu Val Ser Gly His Asp Ala Pro Pro Ala Ile
            260                 265                 270

Leu Thr Phe Glu Glu Ala Asn Leu Cys Gln Thr Leu Asn Asn Asn Ile
        275                 280                 285

Ala Lys Ala Gly Tyr Thr Lys Leu Thr Pro Val Gln Lys Tyr Ser Ile
    290                 295                 300

Pro Ile Val Leu Ala Gly Arg Asp Leu Met Ala Cys Ala Gln Thr Gly
305                 310                 315                 320

Ser Gly Lys Thr Ala Ala Phe Leu Leu Pro Ile Leu Ala His Met Met
                325                 330                 335

Arg Asp Gly Ile Thr Ala Ser Arg Phe Lys Glu Leu Gln Glu Pro Glu
            340                 345                 350

Cys Ile Ile Val Ala Pro Thr Arg Glu Leu Ile Asn Gln Ile Tyr Leu
        355                 360                 365

Glu Ala Arg Lys Phe Ser Phe Gly Thr Cys Val Arg Ala Val Val Ile
    370                 375                 380

Tyr Gly Gly Thr Gln Phe Gly His Ser Ile Arg Gln Ile Val Gln Gly
385                 390                 395                 400

Cys Asn Ile Leu Cys Ala Thr Pro Gly Arg Leu Met Asp Ile Ile Gly
                405                 410                 415

Lys Glu Lys Ile Gly Leu Lys Gln Val Lys Tyr Leu Val Leu Asp Glu
            420                 425                 430

Ala Asp Arg Met Leu Asp Met Gly Phe Gly Pro Glu Met Lys Lys Leu
        435                 440                 445

Ile Ser Cys Pro Gly Met Pro Ser Lys Glu Gln Arg Gln Thr Leu Leu
    450                 455                 460

Phe Ser Ala Thr Phe Pro Glu Glu Ile Gln Arg Leu Ala Gly Glu Phe
465                 470                 475                 480

Leu Lys Ser Asn Tyr Leu Phe Val Ala Val Gly Gln Val Gly Gly Ala
                485                 490                 495

Cys Arg Asp Val Gln Gln Ser Ile Leu Gln Val Gly Pro Val Phe Lys
            500                 505                 510

Lys Arg Lys Leu Val Glu Ile Leu Arg Asn Ile Gly Asp Glu Arg Pro
        515                 520                 525

Met Val Phe Val Glu Thr Lys Lys Lys Ala Asp Phe Ile Ala Thr Phe
    530                 535                 540

Leu Cys Gln Glu Lys Ile Ser Thr Thr Ser Ile His Gly Asp Arg Glu
545                 550                 555                 560

Gln Arg Glu Arg Glu Gln Ala Leu Gly Asp Phe Arg Cys Gly Lys Cys
                565                 570                 575

Pro Val Leu Val Ala Thr Ser Val Ala Ala Arg Gly Leu Asp Ile Glu
            580                 585                 590

Asn Val Gln His Val Ile Asn Phe Asn Leu Pro Ser Thr Ile Asp Glu
        595                 600                 605

Tyr Val His Arg Ile Gly Arg Thr Gly Arg Cys Gly Asn Thr Gly Arg
    610                 615                 620
```

-continued

```
Ala Ile Ser Phe Phe Asp Thr Glu Ser Asp Asn His Leu Ala Gln Pro
625                 630                 635                 640

Leu Val Lys Val Leu Ser Asp Ala Gln Gln Asp Val Pro Ala Trp Leu
                645                 650                 655

Glu Glu Ile Ala Phe Ser Ser Tyr Ala Pro Pro Ser Phe Ser Asn Ser
            660                 665                 670

Thr Arg Gly Ala Val Phe Ala Ser Phe Asp Thr Arg Lys Asn Phe Gln
        675                 680                 685

Gly Lys Asn Thr Leu Asn Thr Ala Gly Ile Ser Ser Ala Gln Ala Pro
    690                 695                 700

Asn Pro Val Asp Asp Glu Ser Trp Asp
705                 710


<210> SEQ ID NO 5
<211> LENGTH: 700
<212> TYPE: PRT
<213> ORGANISM: Xenopus laevis

<400> SEQUENCE: 5

Met Glu Glu Asn Trp Asp Thr Glu Ile Glu Thr Glu Lys Pro Thr Tyr
1               5                   10                  15

Val Pro Asn Phe Ser Thr Leu Glu Thr Glu Asn Thr Asp Asn Tyr Ser
            20                  25                  30

Ala Tyr Ser Asn Asn Asp Ile Asn Asn Gln Asn Tyr Asp Ser Glu Arg
        35                  40                  45

Ser Phe Gly Asn Arg Gly Gly Tyr Arg Ser Glu Arg Ser Arg Pro Ser
    50                  55                  60

Asn Phe Asn Arg Gly Ser Arg Thr Glu Arg Gly Arg Gly Arg Gly Phe
65                  70                  75                  80

Gly Thr Asn Arg Asn Asp Asn Tyr Ser Ser Glu Arg Asp Val Phe Gly
                85                  90                  95

Asp Asp Glu Arg Asp Gln Arg Arg Gly Phe Pro Gly Arg Gly Gly Tyr
            100                 105                 110

Asn Gly Asn Glu Asp Gly Gln Lys Pro Asn Ala Phe Arg Gly Arg Gly
        115                 120                 125

Gly Phe Arg Asn Glu Asn Glu Gln Arg Arg Gly Phe Gly Glu Arg Gly
    130                 135                 140

Gly Phe Arg Ser Glu Asn Gly Gln Arg Asn Phe Asp Asn Arg Gly Asp
145                 150                 155                 160

Phe Gly Asn Ser Gly Glu Glu Glu Asp Arg Pro Arg Ser Tyr Gly Arg
                165                 170                 175

Gly Gly Phe Asn Asn Ser Asp Thr Gly Gly Arg Gly Arg Arg Gly Gly
            180                 185                 190

Arg Gly Gly Gly Ser Gln Tyr Gly Gly Tyr Lys Gly Arg Asn Glu Glu
        195                 200                 205

Val Gly Val Glu Ser Gly Lys Ser Gln Glu Glu Gly Asn Glu Lys Asp
    210                 215                 220

Glu Lys Pro Lys Lys Val Thr Tyr Ile Pro Pro Pro Pro Pro Asp Gly
225                 230                 235                 240

Glu Asp Asn Ile Phe Arg Gln Tyr Gln Ser Gly Ile Asn Phe Asp Lys
                245                 250                 255

Tyr Asp Glu Ile Leu Val Asp Val Thr Gly Lys Asp Val Pro Pro Ala
            260                 265                 270

Ile Leu Thr Phe Glu Glu Ala Asn Leu Cys Glu Thr Leu Arg Arg Asn
        275                 280                 285
```

-continued

```
Val Ala Arg Ala Gly Tyr Val Lys Leu Thr Pro Val Gln Lys His Ser
    290                 295                 300

Ile Pro Ile Ile Met Ala Gly Arg Asp Leu Met Ala Cys Ala Gln Thr
305                 310                 315                 320

Gly Ser Gly Lys Thr Ala Ala Phe Leu Leu Pro Ile Leu Ser Tyr Met
                325                 330                 335

Met Asn Glu Gly Ile Thr Ala Ser Gln Tyr Leu Gln Leu Gln Glu Pro
            340                 345                 350

Glu Ala Ile Ile Ile Ala Pro Thr Arg Glu Leu Ile Asn Gln Ile Tyr
        355                 360                 365

Leu Asp Ala Arg Lys Phe Ser Tyr Gly Thr Cys Val Arg Pro Val Val
    370                 375                 380

Val Tyr Gly Gly Ile Gln Pro Val His Ala Met Arg Asp Val Glu Lys
385                 390                 395                 400

Gly Cys Asn Ile Leu Cys Ala Thr Pro Gly Arg Leu Leu Asp Ile Val
                405                 410                 415

Ser Lys Glu Lys Ile Gly Leu Ser Lys Leu Arg Tyr Leu Val Leu Asp
            420                 425                 430

Glu Ala Asp Arg Met Leu Asp Met Gly Phe Ala Pro Glu Ile Glu Lys
        435                 440                 445

Leu Met Thr Lys Pro Gly Met Pro Thr Lys Glu Lys Arg Gln Thr Leu
    450                 455                 460

Met Phe Ser Ala Thr Tyr Pro Glu Glu Ile Arg Arg Leu Ala Ser Asn
465                 470                 475                 480

Tyr Leu Lys Ser Glu His Leu Phe Val Val Val Gly Leu Val Gly Gly
                485                 490                 495

Ala Cys Ser Asp Val Ala Gln Thr Val Leu Glu Met Arg Glu Asn Gly
            500                 505                 510

Lys Met Glu Lys Leu Leu Glu Ile Leu Lys Ser Ser Glu Lys Glu Arg
        515                 520                 525

Thr Met Ile Phe Val Asn Thr Lys Lys Lys Ala Asp Phe Ile Ala Gly
    530                 535                 540

Tyr Leu Cys Gln Glu Lys Phe Ser Ser Thr Ser Ile His Gly Asp Arg
545                 550                 555                 560

Glu Gln Tyr Gln Arg Glu Ser Ala Leu Trp Asp Phe Arg Thr Gly Lys
                565                 570                 575

Cys Thr Val Ile Val Cys Thr Ala Val Ala Ala Arg Gly Leu Asp Ile
            580                 585                 590

Glu Asn Val Gln His Val Ile Asn Tyr Asp Val Pro Lys Glu Val Asp
        595                 600                 605

Glu Tyr Val His Arg Ile Gly Arg Thr Gly Arg Cys Gly Asn Thr Gly
    610                 615                 620

Lys Ala Thr Ser Phe Phe Asn Val Gln Asp Asp His Val Ile Ala Arg
625                 630                 635                 640

Pro Leu Val Lys Ile Leu Thr Asp Ala His Gln Glu Val Pro Ala Trp
                645                 650                 655

Leu Glu Glu Ile Ala Phe Gly Gly His Gly Ala Leu Asn Ser Phe Tyr
            660                 665                 670

Ala Ala Asp Ser Met Gly Glu Gln Ala Gly Gly Asn Ala Val Thr Thr
        675                 680                 685

Pro Ser Phe Ala Gln Glu Glu Glu Ala Ser Trp Asp
    690                 695                 700
```

```
<210> SEQ ID NO 6
<211> LENGTH: 700
<212> TYPE: PRT
<213> ORGANISM: Danio reio

<400> SEQUENCE: 6

Met Asp Asp Trp Glu Glu Asp Gln Ser Pro Val Val Ser Cys Ser Ser
1               5                   10                  15

Gly Phe Gly Gly Ala Gly Asn Asp Lys Ser Asn Ser Glu Gly Thr Glu
            20                  25                  30

Gly Ser Ser Trp Lys Met Thr Gly Asp Ser Phe Arg Gly Arg Gly Gly
        35                  40                  45

Arg Gly Gly Ser Arg Gly Gly Arg Gly Gly Phe Ser Gly Phe Lys Ser
    50                  55                  60

Glu Ile Asp Glu Asn Gly Ser Asp Gly Gly Trp Asn Gly Gly Glu Ser
65                  70                  75                  80

Arg Gly Arg Gly Arg Gly Gly Phe Arg Gly Gly Phe Arg Ser Gly Ser
                85                  90                  95

Arg Asp Glu Asn Asp Glu Asn Gly Asn Asp Asp Gly Trp Lys Gly Gly
            100                 105                 110

Glu Ser Arg Gly Arg Gly Arg Gly Gly Phe Gly Gly Gly Phe Arg Gly
        115                 120                 125

Gly Phe Arg Asp Gly Gly Asn Glu Asp Thr Gly Arg Arg Gly Phe Gly
    130                 135                 140

Arg Glu Asn Asn Glu Asn Gly Asn Asp Glu Gly Gly Glu Gly Arg Gly
145                 150                 155                 160

Arg Gly Arg Gly Gly Phe Arg Gly Gly Phe Arg Asp Gly Gly Gly Asp
                165                 170                 175

Glu Ser Gly Lys Arg Gly Phe Gly Arg Gly Gly Phe Arg Gly Arg Asn
            180                 185                 190

Glu Glu Val Phe Ser Lys Val Thr Thr Ala Asp Lys Leu Asp Gln Glu
        195                 200                 205

Gly Ser Glu Asn Ala Gly Pro Lys Val Val Tyr Val Pro Pro Pro Pro
    210                 215                 220

Pro Glu Glu Glu Ser Ser Ile Phe Ser His Tyr Ala Thr Gly Ile Asn
225                 230                 235                 240

Phe Asp Lys Tyr Asp Asp Ile Leu Val Asp Val Ser Gly Ser Asn Pro
                245                 250                 255

Pro Lys Ala Ile Met Thr Phe Glu Glu Ala Gly Leu Cys Asp Ser Leu
            260                 265                 270

Ser Lys Asn Val Ser Lys Ser Gly Tyr Val Lys Pro Thr Pro Val Gln
        275                 280                 285

Lys His Gly Ile Pro Ile Ile Ser Ala Gly Arg Asp Leu Met Ala Cys
    290                 295                 300

Ala Gln Thr Gly Ser Gly Lys Thr Ala Ala Phe Leu Leu Pro Ile Leu
305                 310                 315                 320

Gln Arg Phe Met Thr Asp Gly Val Ala Ala Ser Lys Phe Ser Glu Ile
                325                 330                 335

Gln Glu Pro Glu Ala Ile Ile Val Ala Pro Thr Arg Glu Leu Ile Asn
            340                 345                 350

Gln Ile Tyr Leu Glu Ala Arg Lys Phe Ala Tyr Gly Thr Cys Val Arg
        355                 360                 365

Pro Val Val Val Tyr Gly Gly Ile Asn Thr Gly Tyr Thr Ile Arg Glu
    370                 375                 380
```

```
Val Leu Lys Gly Cys Asn Val Leu Cys Ala Thr Pro Gly Arg Leu His
385                 390                 395                 400

Asp Leu Ile Gly Arg Gly Lys Ile Gly Leu Ser Lys Val Arg Tyr Leu
                405                 410                 415

Val Leu Asp Glu Ala Asp Arg Met Leu Asp Met Gly Phe Glu Pro Glu
            420                 425                 430

Met Arg Lys Leu Val Ala Ser Pro Gly Met Pro Ser Lys Glu Lys Arg
        435                 440                 445

Gln Thr Leu Met Phe Ser Ala Thr Tyr Pro Glu Asp Ile Gln Arg Met
    450                 455                 460

Ala Ala Asp Phe Leu Lys Val Asp Tyr Ile Phe Leu Ala Val Gly Val
465                 470                 475                 480

Val Gly Gly Ala Cys Ser Asp Val Glu Gln Thr Ile Val Gln Val Asp
                485                 490                 495

Gln Tyr Ser Lys Arg Asp Gln Leu Leu Glu Leu Leu Arg Ala Thr Gly
            500                 505                 510

Asn Glu Arg Thr Met Val Phe Val Glu Thr Lys Arg Ser Ala Asp Phe
        515                 520                 525

Ile Ala Thr Phe Leu Cys Gln Glu Lys Ile Ser Thr Thr Ser Ile His
    530                 535                 540

Gly Asp Arg Glu Gln Arg Glu Arg Glu Lys Ala Leu Ser Asp Phe Arg
545                 550                 555                 560

Leu Gly His Cys Pro Val Leu Val Ala Thr Ser Val Ala Ala Arg Gly
                565                 570                 575

Leu Asp Ile Glu Gln Val Gln His Val Val Asn Phe Asp Met Pro Ser
            580                 585                 590

Ser Ile Asp Glu Tyr Val His Arg Ile Gly Arg Thr Gly Arg Cys Gly
        595                 600                 605

Asn Thr Gly Arg Ala Val Ser Phe Phe Asn Pro Glu Ser Asp Thr Pro
    610                 615                 620

Leu Ala Arg Ser Leu Val Lys Val Leu Ser Gly Ala Gln Gln Val Val
625                 630                 635                 640

Pro Lys Trp Leu Glu Glu Val Ala Phe Ser Ala His Gly Thr Thr Gly
                645                 650                 655

Phe Asn Pro Arg Gly Lys Val Phe Ala Ser Thr Asp Ser Arg Lys Gly
            660                 665                 670

Gly Ser Phe Lys Ser Asp Glu Pro Pro Pro Ser Gln Thr Ser Ala Pro
        675                 680                 685

Ser Ala Ala Ala Ala Ala Asp Asp Glu Glu Trp Glu
    690                 695                 700


<210> SEQ ID NO 7
<211> LENGTH: 661
<212> TYPE: PRT
<213> ORGANISM: Drosophila melanogaster

<400> SEQUENCE: 7

Met Ser Asp Asp Trp Asp Asp Glu Pro Ile Val Asp Thr Arg Gly Ala
1               5                   10                  15

Arg Gly Gly Asp Trp Ser Asp Asp Glu Asp Thr Ala Lys Ser Phe Ser
            20                  25                  30

Gly Glu Ala Glu Gly Asp Gly Val Gly Gly Ser Gly Gly Glu Gly Gly
        35                  40                  45

Gly Tyr Gln Gly Gly Asn Arg Asp Val Phe Gly Arg Ile Gly Gly Gly
```

-continued

```
    50                  55                  60

Arg Gly Gly Gly Ala Gly Gly Tyr Arg Gly Gly Asn Arg Asp Gly Gly
65                  70                  75                  80

Gly Phe His Gly Gly Arg Arg Glu Gly Glu Arg Asp Phe Arg Gly Gly
                85                  90                  95

Glu Gly Gly Phe Arg Gly Gly Gln Gly Gly Ser Arg Gly Gly Gln Gly
            100                 105                 110

Gly Ser Arg Gly Gly Gln Gly Gly Phe Arg Gly Gly Glu Gly Gly Phe
        115                 120                 125

Arg Gly Arg Leu Tyr Glu Asn Glu Asp Gly Asp Glu Arg Arg Gly Arg
    130                 135                 140

Leu Asp Arg Glu Glu Arg Gly Gly Glu Arg Arg Gly Arg Leu Asp Arg
145                 150                 155                 160

Glu Glu Arg Gly Gly Glu Arg Gly Glu Arg Gly Asp Gly Gly Phe Ala
                165                 170                 175

Arg Arg Arg Arg Asn Glu Asp Asp Ile Asn Asn Asn Asn Asn Ile Ala
            180                 185                 190

Glu Asp Val Glu Arg Lys Arg Glu Phe Tyr Ile Pro Pro Glu Pro Ser
        195                 200                 205

Asn Asp Ala Ile Glu Ile Phe Ser Ser Gly Ile Ala Ser Gly Ile His
    210                 215                 220

Phe Ser Lys Tyr Asn Asn Ile Pro Val Lys Val Thr Gly Ser Asp Val
225                 230                 235                 240

Pro Gln Pro Ile Gln His Phe Thr Ser Ala Asp Leu Arg Asp Ile Ile
                245                 250                 255

Ile Asp Asn Val Asn Lys Ser Gly Phe Lys Ile Pro Thr Pro Ile Gln
            260                 265                 270

Lys Cys Ser Ile Pro Val Ile Ser Ser Gly Arg Asp Leu Met Ala Cys
        275                 280                 285

Ala Gln Thr Gly Ser Gly Lys Thr Ala Ala Phe Leu Leu Pro Ile Leu
    290                 295                 300

Ser Lys Leu Leu Glu Asp Pro His Glu Leu Glu Leu Gly Arg Pro Gln
305                 310                 315                 320

Val Val Ile Val Ser Pro Thr Arg Glu Leu Ala Ile Gln Ile Phe Asn
                325                 330                 335

Glu Ala Arg Lys Phe Ala Phe Glu Ser Tyr Leu Lys Ile Gly Ile Val
            340                 345                 350

Tyr Gly Gly Thr Ser Phe Arg His Gln Asn Glu Cys Ile Thr Arg Gly
        355                 360                 365

Cys His Val Val Ile Ala Thr Pro Gly Arg Leu Leu Asp Phe Val Asp
    370                 375                 380

Arg Thr Phe Ile Thr Phe Glu Asp Thr Arg Phe Val Val Leu Asp Glu
385                 390                 395                 400

Ala Asp Arg Met Leu Asp Met Gly Phe Ser Glu Asp Met Arg Arg Ile
                405                 410                 415

Met Thr His Val Thr Met Arg Pro Glu His Gln Thr Leu Met Phe Ser
            420                 425                 430

Ala Thr Phe Pro Glu Glu Ile Gln Arg Met Ala Gly Glu Phe Leu Lys
        435                 440                 445

Asn Tyr Val Ser Val Ala Ile Gly Ile Val Gly Gly Ala Cys Ser Asp
    450                 455                 460

Val Lys Gln Thr Ile Tyr Glu Val Asn Lys Tyr Ala Lys Arg Ser Lys
465                 470                 475                 480
```

-continued

```
Leu Ile Glu Ile Leu Ser Glu Gln Ala Asp Gly Thr Ile Val Phe Val
                485                 490                 495

Glu Thr Lys Arg Gly Ala Asp Phe Leu Ala Ser Phe Leu Ser Glu Lys
            500                 505                 510

Glu Phe Pro Thr Thr Ser Ile His Gly Asp Arg Leu Gln Ser Gln Arg
        515                 520                 525

Glu Gln Ala Leu Arg Asp Phe Lys Asn Gly Ser Met Lys Val Leu Ile
    530                 535                 540

Ala Thr Ser Val Ala Ser Arg Gly Leu Asp Ile Lys Asn Ile Lys His
545                 550                 555                 560

Val Ile Asn Tyr Asp Met Pro Ser Lys Ile Asp Asp Tyr Val His Arg
                565                 570                 575

Ile Gly Arg Thr Gly Cys Val Gly Asn Asn Gly Arg Ala Thr Ser Phe
            580                 585                 590

Phe Asp Pro Glu Lys Asp Arg Ala Ile Ala Ala Asp Leu Val Lys Ile
        595                 600                 605

Leu Glu Gly Ser Gly Gln Thr Val Pro Asp Phe Leu Arg Thr Cys Gly
    610                 615                 620

Ala Gly Gly Asp Gly Gly Tyr Ser Asn Gln Asn Phe Gly Gly Val Asp
625                 630                 635                 640

Val Arg Gly Arg Gly Asn Tyr Val Gly Asp Ala Thr Asn Val Glu Glu
                645                 650                 655

Glu Glu Gln Trp Asp
            660


<210> SEQ ID NO 8
<211> LENGTH: 28
<212> TYPE: DNA
<213> ORGANISM: Homo sapiens

<400> SEQUENCE: 8

ctctgcatca aaaccacaga cttgaagg                                        28


<210> SEQ ID NO 9
<211> LENGTH: 30
<212> TYPE: PRT
<213> ORGANISM: Homo sapiens

<400> SEQUENCE: 9

Cys Glu Asp Asn Pro Thr Arg Asn Arg Gly Phe Ser Lys Arg Gly Gly
1               5                   10                  15

Tyr Arg Asp Gly Asn Asn Ser Glu Ala Ser Gly Pro Tyr Arg
            20                  25                  30


<210> SEQ ID NO 10
<211> LENGTH: 29
<212> TYPE: PRT
<213> ORGANISM: Homo sapiens

<400> SEQUENCE: 10

Val Asp Thr Arg Lys Gly Lys Ser Thr Leu Asn Thr Ala Gly Phe Ser
1               5                   10                  15

Ser Ser Arg Ala Pro Asn Pro Val Asp Asp Glu Ser Trp
            20                  25


<210> SEQ ID NO 11
<211> LENGTH: 20
<212> TYPE: DNA
```

<213> ORGANISM: Homo sapiens

<400> SEQUENCE: 11
aagtcaccat gggggatgaa 20

<210> SEQ ID NO 12
<211> LENGTH: 28
<212> TYPE: DNA
<213> ORGANISM: Homo sapiens

<400> SEQUENCE: 12
ttaagatctt ttttgcacag gagtaagc 28

<210> SEQ ID NO 13
<211> LENGTH: 21
<212> TYPE: DNA
<213> ORGANISM: Homo sapiens

<400> SEQUENCE: 13
tgcatcaaaa ccacagactt g 21

<210> SEQ ID NO 14
<211> LENGTH: 20
<212> TYPE: DNA
<213> ORGANISM: Homo sapiens

<400> SEQUENCE: 14
aatgccatca aaggaacagc 20

<210> SEQ ID NO 15
<211> LENGTH: 2172
<212> TYPE: DNA
<213> ORGANISM: Homo sapiens

<400> SEQUENCE: 15
atgggggatg aagattggga agcagaaatc aaccctcata tgtcttccta tgttcccata 60
tttgagaagg ataggtattc tggagaaaat ggagacaatt ttaacaggac tccagcttca 120
tcatcagaaa tggatgatgg accttctcga agagatcatt tcatgaaaag tggatttgcc 180
tctgggcgga attttggaaa cagagatgct ggtgagtgta ataagcgaga taatacatcc 240
acaatgggtg gttttggagt tggaaagagt tttggaaaca gaggtttttc aaacagcagg 300
tttgaagatg gtgatagctc tggtttctgg agagagtcta gtaatgactg cgaagataat 360
ccaacacgga acagagggtt ttccaagaga ggcggctatc gagatggaaa taattcagaa 420
gcttcagggc catacagaag aggtggaaga ggtagtttcc gaggttgccg tggaggattt 480
ggtctaggaa gtccaaataa tgacttagac ccagacgaat gtatgcagcg cactggtggc 540
ctttttggtt ctagaagacc agtattaagt ggcacaggta atggtgatac ttctcaaagc 600
agaagtggca gtggaagtga acgaggtggt tacaaaggtt taaatgaaga agtaataaca 660
ggctctggaa agaattcttg gaagtcagaa gcagaaggag gagaaagtag tgatactcaa 720
ggaccaaaag tgacctacat accccctcct ccacctgagg atgaggactc catctttgca 780
cattatcaga caggcataaa cttcgacaaa tacgacacta ttcttgtgga agtgtctgga 840
catgatgcac caccagcaat tctgactttt gaagaagcta atctctgtca gacactgaat 900
aacaacattg ctaaagctgg ttatactaag cttactcctg tgcaaaaata cagtattcct 960
atcatacttg caggacgaga tttgatggct tgtgctcaaa cagggtctgg gaagactgcg 1020
gcttttctcc taccaatttt ggctcatatg atgcatgatg gaataactgc cagtcgtttt 1080

```
aaagagttgc aggaaccaga gtgtattatt gtagcaccaa ctcgagaatt ggtcaaccag   1140

atttatttgg aagccagaaa attttctttt gggacttgtg taagagctgt tgttatatat   1200

gggggaaccc agctgggaca ttcaattcga caaatagtac aaggctgtaa tatattatgt   1260

gctactcctg gaagactgat ggatatcata ggcaaagaaa agattggtct caaacagatc   1320

aaatacttag ttttggatga agctgatcgc atgttggata tgggttttgg tccagaaatg   1380

aagaagttaa tttcttgccc aggaatgcca tcaaaggaac agcgccaaac ccttatgttc   1440

agtgcaactt ttccagagga aattcaaagg ttggctgcag agtttttaaa gtcaaattat   1500

ctgtttgttg ctgttggaca agtgggtgga gcatgtagag atgttcagca gaccgttctc   1560

caagttggcc agttctcaaa aagagaaaag ctcgttgaaa ttctgcgaaa catagggat   1620

gaaagaacta tggtctttgt tgaaactaag aaaaaagcag attttactgc aacttttctt   1680

tgtcaagaaa aaatatcaac tacaagtatc catggtgatc gggaacagag agagcgggag   1740

caagctcttg gagattttcg ctttggaaag tgcccagttc ttgttgctac ttcagtagct   1800

gccagagggc tggatattga aaatgtgcaa catgttatca attttgatct tccttctacc   1860

attgatgaat atgttcatcg aattgggcgt actggtcgtt gtgggaatac tggcagagca   1920

atttcctttt ttgatcttga atcggataac catttagcac agcctctagt aaaagtattg   1980

acagatgctc aacaggatgt tcctgcatgg ttggaagaaa ttgcctttag tacatacatt   2040

cctggcttca gtggtagtac aagaggaaac gtgtttgcat cagttgatac cagaaagggc   2100

aagagcactt tgaacacagc tgggttttct tcttcacgag ctcccaatcc agtagatgat   2160

gagtcatggg at                                                        2172
```

<210> SEQ ID NO 16
<211> LENGTH: 3030
<212> TYPE: DNA
<213> ORGANISM: Rattus sp.

<400> SEQUENCE: 16

```
cttgcttcca accctggctc agggcgtcct aaccaggccc ggtagcctct ggggcagact     60

taggccagag gctgctcaca tggcctgcc tggggcttga ggtcggcctc tggggccttc    120

ccgctcagac tggagtcttc atgctgagta gagcggtgtg tgaacacttg aggcctgcag    180

gggagggagg cccagggaac cttctgctca gcgcctaggc ggccatttct cagaagaaac    240

ggtgtttgtg gaacctgaag ctatcatggg agatgaagat tgggaggcag aaatcctcaa    300

acctcatgtg tcttcctacg ttcctgtatt tgagaaggat aaatattctt ctggggcaaa    360

tggagacact tttaacagga cttcagcttc atcatcagaa atggaagatg gaccttctgg    420

aagagatcat ttcatgagaa gtggattttc ctctggaaga aatttaggaa acagagatat    480

tggcgagtct agtaaaagag agactacatc tacaaccggt ggctttggaa gaggaaaggg    540

ttttggaaac agaggttttt taaataacaa gtttgaagaa ggtgacagct ctggtttctg    600

gaaagagtct actaatgact gtgaagatac tcagactcgg agcagagggt tttccaagcg    660

aggcggctat ccagatggga atgattcgga agcttcaggc ccattcagaa gaggtgggag    720

agatagtgaa tatgaccaag atcagggatc acagcgtggt ggtggccttt ttggttctag    780

gaaaccagca gcaagtgatt caggcagtgg tgacactttc cagagcagaa gtgggaatgc    840

ccgaggtgcc tacaaaggct taaatgaaga agtagtaaca ggctctggaa agaattcttg    900

gaagtcagaa gctgaaggag gcgaaagcag tgatattcaa ggtccaaaag tgacatatat    960
```

-continued

```
acccctcct ccaccagagg atgaggactc catctttgca cattatcaga caggcataaa   1020

ctttgataaa tatgatacca tacttgttga agtatctgga catgatgcac caccggcaat   1080

tttgactttt gaagaagcga atctctgcca gaccctgaat aacaacattg ctaaggctgg   1140

ctataccaag ctcactcctg tgcagaagta cagcattccc attgtgttag caggaagaga   1200

tttgatggct tgtgctcaaa cagggtctgg gaagacggca gcttttctct tgcctatttt   1260

ggctcatatg atgagggatg gaataactgc cagtcgcttt aaagaactgc aggaaccaga   1320

gtgtattatt gtagcaccaa ctcgagaatt gatcaaccaa atttatttgg aagccagaaa   1380

attttctttt gggacttgtg taagagctgt tgtcatatat ggaggaaccc agtttgggca   1440

ctcaattcga cagatagtgc aagggtgtaa tatattatgt gctactccag ggaggctgat   1500

ggatatcata ggcaaagaaa agattggtct caaacaagtc aagtacttag ttttggatga   1560

agctgatcga atgttggata tgggttttgg acccgaaatg aagaagttaa tttcttgtcc   1620

aggaatgcca tcaaaggaac agcgccaaac tctcttattc agtgcaactt ttccagaaga   1680

aatccagagg ttggctggcg agtttttaaa gtcaaattat ttgtttgttg ctgttggaca   1740

agtgggagga gcttgcagag atgtgcagca gtccattctt caagttggcc cagtattcaa   1800

aaagagaaaa cttgttgaga ttctacgaaa cataggtgat gaaagaccta tggtctttgt   1860

tgaaaccaag aaaaaagcag atttcattgc gactttcctt tgtcaagaaa aaatatcaac   1920

tacaagtatt catggcgatc gggaacagag ggagcgagaa caagctcttg gagattttcg   1980

ctgtggaaag tgcccagttc ttgttgctac ttcagtggct gccagaggac ttgatattga   2040

aaatgttcaa catgttatca attttaacct tccttctacc attgatgaat atgttcatcg   2100

aattggacgt actggacgtt gtggaaatac tggcagggcg atttcttttt ttgataccga   2160

atctgataat catttagcac aacctctagt taaagtactg tcagatgctc aacaggatgt   2220

tcctgcgtgg ttagaagaga ttgcctttag ttcatatgcg cctcccagct tcagtaatag   2280

cacaagaggg gctgtgtttg catcttttga cactaggaag aatttccagg gcaagaacac   2340

actgaacaca gctgggattt cttctgcaca agctcccaat ccagttgatg acgagtcatg   2400

ggattaaagc aaacaagcat actgcaagtc tgatggtttt gatgcagaga agaaaaacag   2460

tttttatttt taaaatttta acagaagtgt gaaacctgat attcttatat ctcctgttct   2520

tctgttctta ctcccaaccc ttaaaaaata accagcttca ttgattagtt atgcgaaatg   2580

ctgaagttac aacattgcag ttactgatac aaatggtgtt cactggaaat attaaagcat   2640

tctatgtttt gcttatttct agtatattct tcagaaagtt aaagacatgt ttcatgtcca   2700

agtgctatgt cttagtatag tgtttctgat ctataaaaca agcaatagga tatggtgtac   2760

tcttgtttaa ttatcgggtc taatttctac ttgatccttt aaaagaatag tgtgtcagta   2820

caatgtatta acatgatttt catgaaacag tggagactga agcctttcaa agttatttga   2880

tttttagatc atcagacatg taatgaaaat ggttcagttt gcaatgtgag ctctgtactt   2940

ggtggtatga caaatgtttg cttttataat atacagattt tccttggaaa taaaagatga   3000

aacacatttc cccctaaaaa aaaaaaaaaa                                    3030
```

<210> SEQ ID NO 17
<211> LENGTH: 1930
<212> TYPE: DNA
<213> ORGANISM: Mus musculus

<400> SEQUENCE: 17

```
tttggaagag gaaagggctt tggaaacaga ggttttttaa ataacaagtt tgaagaaggt     60
```

-continued

```
gatagctctg gtttctggaa agagtctaat aatgactgtg aagataatca gactcgaagc    120
agagggtttt ccaagcgagg tggctgccaa gatggaaacg attcagaagc atcaggcccg    180
ttcagaagag ggggaagagg cagtttccga ggctgccgtg gaggatttgg tctaggaaga    240
ccaaatagtg aatctgacca agatcagggg acacagtgtg gtggtggctt tctggttcta    300
gggaaaccag cagcaagtga ttcaggcaat ggtgacactt accaaagcag aagtggaagt    360
ggtcgaggtg gttacaaagg tttaaatgaa gaagtagtaa caggttctgg aaagaattct    420
tggaagtcag aaactgaagg aggtgaaagc agtgatagtc aaggtccaaa agtgacatat    480
ataccccccc ctccaccaga ggatgaggac tccatctttg cacattatca gacaggcata    540
aactttgata aatatgacac catacttgtt gaagtatctg gacatgatgc accaccggca    600
attttgactt ttgaagaagc taatctctgt cagacactga ataacaacat tcgtaaagct    660
ggctatacta agcttactcc tgtgcagaag tacacgattc ccattgtatt agcaggacga    720
gatttgatgg cttgtgctca aacagggtct gggaagactg cagcttttct cttgcctatt    780
ttggctcata tgatgcggga tggaataact gccagtcgct ttaaagaact gcaggaacca    840
gagtgtatta ttgtagcacc aactcgagaa ctgatcaacc aaatttactt ggaagccaga    900
aaattttctt ttgggacttg tgtaatatct gtggtcatat atggagggac ccagtttggt    960
cattcagttc gacagatagt acaagggtgt aacatattgt gtgctactcc agggaggctg   1020
atggacatca taggcaaaga aaagattggc ctcaaacaag tcaagtactt agttttggat   1080
gaagctgata gcatgctaga catgggtttt gcaccagaga tcaagaaact aatttcttgt   1140
ccaggaatgc catcaaagga acaacaccaa acccttttat tcagtgctac ttttccagaa   1200
gaaatccaga ggttggctgg ggattttcta aagtccaatt atttgtttgt tgctgttggg   1260
caagtgggag gagcttgcag agatgttcag cagacgattc ttcaagttgg ccagtatcaa   1320
aaagagaaaa gcttgttgag attctacgaa aacataggtg atgaaagaac tatggtcttt   1380
gttgaaacca agaaaaaagc cgatttcatt gcaacttttc tttgtcaaga aaaaatatca   1440
agtacaagta ttcatggtga tcgggaacag agggagagag agcaagctct tggagatttt   1500
cgctgtggaa agtgcccagt tcttgttgct acttcagtgg ctgccagagg gcttgatatt   1560
gaaaatgttc aacatgttat caattttgac cttccttcta ccattgatga gtatgttcat   1620
cgaattggac gcactggccg ctgtggaaat actggcagag cgatttcttt ttttgatact   1680
gactctgata atcatttagc acagcctcta gttaaagtac tgtcagacgc tcaacaggat   1740
gtccccgcat ggctagaaga gattgccttc agtacctatg tgcctcccag cttcagtagc   1800
agcacaagag gggggccgt gtttgcatct gttgacacga ggaagaatta ccagggcaaa   1860
gcacacgttg aatacagcgg ggatttcttc ttcacaagct cccaatccag ttgatgacga   1920
atcatgggcc                                                           1930

<210> SEQ ID NO 18
<211> LENGTH: 2865
<212> TYPE: DNA
<213> ORGANISM: Danio rerio

<400> SEQUENCE: 18

tcaggctctt cacgcgtgtc cacctgctac cggctcttct gaaaaaaagt ctcacctaaa     60
attacccaat atggatgact gggaggaaga tcagagtccc gttgtgtctt gcagctcagg    120
atttggtcta ggctcaaatg gttctgatgg aggattcaag agcttttata caggaggtgc    180
```

-continued

```
tggaaatgac aagtcaaaca gtgaaggtac tgaaggtagc tcatggaaaa tgactggtga    240
ttcgttcagg gggagaggag gcaggggagg atcacgagga ggcagaggag gctttagcgg    300
ttttaaatca gaaattgatg agaatggcag cgatggaggt tggaacggag gtgaaagtcg    360
aggaagagga cgcggtggtt tccgtggtgg ttttcgcagt ggctcccgtg atgaaaatga    420
tgaaaataga aatgatgatg gttggaaagg aggtgaaagc cgaggtagag gtcgaggtgg    480
tttcgggggt agttttcgtg gaggtttccg tgatggtggt aatgaagaca ctgggagaag    540
aggctttgga agagaaaata atgaaaatgg aaacgatgag ggaggagaag gcagaggaag    600
aggtcgtggt ggtttccggg gtggttttcg tgatggtggt ggtgatgaga gtggaaaaag    660
aggcttcgga agaggaggtt ttagaggccg gaatgaggaa gtattttcca aggtcacaac    720
tgcagacaag ttggatcaag aaggaagtga aaatgcagga cccaaggttg tttatgtgcc    780
gccgcctcct ccagaggagg agagctcgat attctcccat tatgcaacag gcattaattt    840
tgacaaatat gatgatattc ttgtggacgt gagtggcagc aatcctccaa aagcaattat    900
gacttttgag gaagcaggac tttgtgactc actgagcaaa aatgtatcaa agtctggata    960
tgtgaagcct acacctgttc agaaacatgg cattcccatc atttcagctg gacgggatct   1020
aatggcttgt gctcagactg gatcaggaaa aacggcggcc ttcctgctgc ctatcctaca   1080
gcgctttatg actgatggtg tggcagccag caagttcagt gagatacagg agcctgaggc   1140
cataatcgtg gctcccacca gagaacttat caatcagatc tatctggagg ccaggaagtt   1200
tgcatacggg acctgtgtac gacctgttgt ggtttatgga ggtataaata ctggatatac   1260
tatccgagag gtgttaaagg gctgcaatgt tctgtgtgct actcctggaa gattgcatga   1320
cctcattggt cgtggaaaga ttggcctgag taaagtgcgc tatctagttc tggatgaagc   1380
agacagaatg ctggacatgg gctttgagcc agaaatgcgc aaactggtgg cgtctcctgg   1440
tatgccttca aaagaggaac gacaaaccct catgttcagt gccacctacc ctgaagatat   1500
tcaaagaatg gctgctgact ttcttaaagt ggactatatt ttccttgctg ttggtgtggt   1560
gggtggagca tgcagtgatg tggagcaaac cgttgttcag gtggaccagt actcaaagag   1620
ggaccagctg cttgaattgc tcagagcaac aggtaatgag cgcacaatgg tttttgtgga   1680
aaccaaaaga agtgctgatt tcatagcaac atttctctgt caagagaaga tctcaaccac   1740
aagcatccat ggtgatcggg aacagcgaga gcgagagaaa gctctcagtg attttcgcct   1800
tggccactgt ccggttctgg tcgccacatc tgtagctgct agaggcctgg atattgagca   1860
agtccagcat gttgtgaatt ttgacatgcc cagcagcatc gatgagtatg tccatcgcat   1920
aggaagaact ggacgctgtg ggaacaccgg tcgcgccgtg tccttttttta acccagagtc   1980
tgacactcca ctagctcgct ccctggtcaa agtcctttca ggggcccaac aagtagttcc   2040
aaaatggctg gaggaagttg ccttcagtgc tcatggcaca acaggcttca acccacgtgg   2100
aaaggtgttt gcatctacag actcgcggaa gggaggatcc tttaagagcg atgagccgcc   2160
accatcacaa acatctgccc cgagcgcagc agctgctgca gacgatgagg aatgggaata   2220
actggcctca cacctgttat atttatttta tttttatttt atttgtgcga gcttcttcaa   2280
taccatttca ggatatttgt taatgttgaa tgactaaagt agcattagga taaagctgtt   2340
gtatttagag tcacattgaa tgctgtaggt ttgacctcaa ggacgataat caagactaat   2400
acctttttggc agtttgattt gatcatcttt ttggtatcac tcgtttggac tggagcacaa   2460
ctgaattagt ggatttgttt tactagagca caagtgcaga agtgggtggg tttgtttaat   2520
cacattttaa cactttttgc taggagtgta ttgagttttg taagctttga cctaaaggtg   2580
```

```
tttcctacag ttaaatctat taatcagttc tattgttgat tgtgactgtt tgtaggttat   2640

ttttcttgac atttccgtct tgaagccaga gtatagaaca agaaacttgt tttgcagatg   2700

taccttgcca gataaaggta gctaaagtca ttgtttaaca gacatctctt taattttaaa   2760

gtcaaaatgt tgataaaatt cagtcaagag gcagtgactg actgtaacag agcggtgctt   2820

cctcactagc tgaagtggct caaaataaag acggatactg gtgac                    2865
```

<210> SEQ ID NO 19
<211> LENGTH: 2492
<212> TYPE: DNA
<213> ORGANISM: Danio rerio

<400> SEQUENCE: 19

```
cttctgaaaa aaagtctcac ctaaaattac ccaatatgga tgactgggag gaagatcaga     60

gtcccgttgt gtcttgcagc tcaggatttg gaggcgctgg aaatgacaag tcaaacagtg    120

aaggtactga aggtagctca tggaaaatga ctggtgattc gtttaggggg agaggaggca    180

ggggaggatc acgaggaggc agaggaggct ttagcggttt taaatcagaa attgatgaga    240

atggcagcga tggaggttgg aacggaggtg aaagtcgagg aagaggacgc ggtggtttcc    300

gtggtggttt tcgcagtggc tcccgtgatg aaaatgatga aaatggaaat gatgatggtt    360

ggaaaggagg tgaaagccga ggtagaggtc gaggtggttt cgggggtggt tttcgtggag    420

gtttccgtga tggtggtaat gaagacactg ggagaagagg ctttggaaga gaaaataatg    480

aaaatgggaa cgatgaggga ggagaaggca gaggaagagg tcgtggtggt ttccggggtg    540

gttttcgtga tggtggtggt gatgagagtg gaaaaagagg cttcggaaga ggaggtttta    600

gaggccggaa tgaggaagta ttttccaagg tcacaactgc agacaagttg gatcaagaag    660

gaagtgaaaa tgcaggaccc aaggttgttt atgtgccgcc gcctcctcca gaggaggaga    720

gctcgatatt ctcccattat gcaacaggca ttaattttga caaatatgat gatattcttg    780

tggacgtgag tggcagcaat cctccaaaag caattatgac ttttgaggaa gcaggacttt    840

gtgactcact gagcaaaaat gtatcaaagt ctggatatgt gaagcctaca cctgttcaga    900

aacatggcat tcccatcatt tcagctggac gggatctaat ggcttgtgct cagactggat    960

caggaaaaac ggcggccttc ctgctgccca tcctacagcg ctttatgact gatggtgtgg   1020

cagccagcaa gttcagtgag atacaggagc ctgaggccat aatcgtggct cccaccagag   1080

aacttatcaa tcagatctat ctggaggcca ggaagtttgc atacgggacc tgtgtacgac   1140

ctgttgtggt ttatggaggt ataaataccg gatatactat ccgagaggtg ttaaagggct   1200

gcaatgtatt gtgtgctact cctggaagat tgcatgacct cattggtcgt ggaaagattg   1260

gcctgagtaa agtgcgctat ctagttctgg atgaagcaga cagaatgctg gacatgggct   1320

ttgagccaga aatgcgcaaa ctggtggcgt ctcctggtat gccttcaaaa gagaaacgac   1380

aaaccctcat gttcagtgcc acctaccctg aagatattca aagaatggct gctgactttc   1440

ttaaagtgga ctatattttc cttgctgttg gtgtggtggg tggagcatgc agtgatgtgg   1500

aacaaaccat tgttcaggtg gaccagtact caaagaggga ccagctgctt gaattgctca   1560

gagcaacagg taatgagcgc acaatggttt ttgttgaaac caaaagaagt gctgatttca   1620

tagcaacatt tctctgtcaa gagaagatct caaccacaag catccatggt gatcgggaac   1680

agcgagagcg agagaaagct ctcagtgatt ttcgccttgg ccactgtccg gttttggtcg   1740

ccacatctgt agctgctaga ggcctggata ttgagcaagt ccagcatgtt gtgaattttg   1800
```

-continued

```
acatgcccag cagcatcgat gagtatgtcc atcgcatagg aagaactgga cgctgtggga   1860
acaccggtcg ggccgtgtcc ttttttaacc cagagtctga cactccacta gctcgctccc   1920
tggtcaaagt cctttcaggg gcccaacaag tagttccaaa atggctggag gaagttgcct   1980
tcagtgctca tgggacaaca ggcttcaacc cacgtgggaa ggtgtttgca tctacagact   2040
cgcggaaggg aggatccttc aagagcgatg agccgccacc atcacaaaca tctgccccga   2100
gtgcagcagc tgctgcagac gatgaggaat gggaataact ggcctcaaac ctgttatatt   2160
tattttattt ttattttatt tgtgcgagct tcttcaatac catttcagga tatttgttaa   2220
tgttgaatga ctaaagtagc attaggataa agctgttgta tttagagtca cattgaatgc   2280
tgtaggtttg acctcaagga caataatcaa gactaatacc ttttgtcagt ttgatttgat   2340
catctttttg gtatcactcg tttggactgg agcacaactg aattagtgga tttgttttac   2400
tagagcacaa gtgcagaagt gggtgggttt gtttaatcac attttaacac tttgctagga   2460
ctaaaaaaaa aaaaaaaaaa aaaaaaaaaa aa                                 2492
```

<210> SEQ ID NO 20
<211> LENGTH: 2502
<212> TYPE: DNA
<213> ORGANISM: Xenopus laevis

<400> SEQUENCE: 20

```
gattcaggag ctttcctgga gtctcgcttg atagtcacct gcaagttggg cagattaaac     60
cgagaatgga ggaaaactgg gatactgaaa ttgaaactga aaaaccaact tatgtaccga    120
atttcagtac cttggagacc gaaaatacag ataattacag tgcctactct aacaatgata    180
tcaacaatca aaattatgat tctgaaagaa gttttggaaa ccgaggaggt tatcggtctg    240
aaaggagtag gcctagtaat tttaacagag gtagtcgaac tgaaagggga agaggacgag    300
ggtttggtac taatcgaaat gataattatt cttctgagag agatgtgttt ggagatgatg    360
agagggatca acgcagaggg tttccaggca gaggtggata taatggcaat gaagatggac    420
agaaacctaa tgcctttcga ggaagaggtg ggttcagaaa tgagaatgaa cagcgtcgag    480
gctttggaga aagaggagga tttagaagcg agaatggaca gcgaaacttt gataacagag    540
gagattttgg taattctggt gaagaagagg atcgtccacg ttcttatggg agaggtggtt    600
ttaacaactc tgatactggt ggaagaggac gaagaggtgg ccgaggtggt ggaagccagt    660
atggtggata caaaggaaga aatgaagaag ttggtgtaga atctggaaaa agtcaagaag    720
aaggaaatga aaaagatgaa aaaccaaaaa aggtgaccta tattcctccg cctccacctg    780
atggtgaaga taatatattc cggcaatacc agtctggaat caattttgat aaatatgatg    840
agattcttgt tgatgtgaca ggaaaggatg ttcctcctgc catactgact tttgaagaag    900
ctaacctttg tgaaacacta agaagaaatg ttgctagagc tggatatgta aagctaacac    960
cagtgcagaa acacagcatc cctattataa tggctggtcg tgatttaatg gcttgcgcac   1020
agactggttc tggtaaaact gctgcttttc ttttgccaat tctcagttat atgatgaatg   1080
aaggaattac agctagtcag tatttacaac ttcaggaacc agaagccata attattgccc   1140
ctaccagaga acttattaac cagatatatc tcgatgctcg aaaattttca tatggaacct   1200
gcgtgcgtcc agtagttgta tatggtggta tacaacctgt acatgcaatg agggacgttg   1260
aaaaagggtg caatatactt tgtgcaaccc ctggaagatt gctggacata gtaagcaaag   1320
aaaaaattgg cttaagtaag ctaagatatc tagttctgga tgaagcggat cgcatgttgg   1380
atatgggatt tgccccggaa atagaaaaat taatgacaaa gccaggaatg ccaacaaaag   1440
```

```
aaaagcgaca aacactaatg ttcagtgcta cctatcctga ggaaattcgg aggttggctt   1500

cgaattattt gaaatctgaa catttgtttg ttgtggtcgg attagttgga ggagcttgta   1560

gtgatgtggc acaaacagtt cttgaaatgc gagaaaatgg aaagatggaa aagctacttg   1620

aaattctgaa aagctcagag aaagagcgaa ctatgatttt tgtgaataca aaaaagaagg   1680

cagattttat tgctggttac ctttgtcaag agaaattttc atcaacaagc attcacggtg   1740

atagagaaca ataccaaaga gagagtgctc tctgggattt cagaactgga aagtgtactg   1800

ttattgtctg cacagcagtt gctgccagag gcttggatat tgaaaatgtt caacacgtga   1860

taaattatga cgttcctaag gaagttgatg agtacgtcca tagaattggt cgtaccggtc   1920

gctgtggtaa caccggaaag gcaacatcat tttcaatgt tcaggatgac catgtgattg   1980

ctcgtcccct tgtgaaaatt cttaccgatg ctcatcaaga agtccctgct tggttagaag   2040

aaattgcctt tgggggccat ggagctttga atagctttta tgcagcggac tctatgggcg   2100

aacaggccgg aggaaatgcc gtcactactc cttcattcgc acaagaagaa gaggctagct   2160

gggattaaat agtagaatca aattgcagaa ttcaaatatt gttaaaatgt ttaaaaagaa   2220

atcttgtttt ataacatctt ttccaagagc tgaaatgacg aaaaaactcc ttatgtgaga   2280

attatcaatc gcaagcagag caagttattt gatttagttt gaacctttaa gagaatgtgt   2340

ttacattcaa cttggccatc atttatttca ttaaaacctt tattgtttaa ctgcaactga   2400

aagtttgact tgtataatta ttaaaccaag ttttgtttgc tttttcttcc aaaacaagca   2460

ccaataaacc cacatcattc tgaaccgaaa aaaaaaaaaa aa                       2502
```

<210> SEQ ID NO 21
<211> LENGTH: 34841
<212> TYPE: DNA
<213> ORGANISM: Caenorhabditis elegans

<400> SEQUENCE: 21

```
gatcggaatc cattgtacgt tgttttttga aattttttta taacaaatta ttgaaaaaaa     60

aactagaaat tcagaaaatt gaaattggaa ttaacatgat catttttaag actttttaaa    120

gaagattgaa aattataaaa atttattttg aaaaaaaaaa tttttaattt gctctaaaat    180

actcaaaaaa aaacggaatt tttaatacta ctactttaaa aatttgtaaa ttaaaaaata    240

acataattca actgaaaaaa cggctaaagc tagcttcttt acctaaattt tcagatattt    300

taagatattt tacattttat ccgaaaaata atttttttaa accaaaaaac acaacattct    360

gttctaattt ttggggcaaa aaacaaaaaa aaaacatttc ttccgaaaat tcgaaaaaaa    420

aaaaccaaaa aacacaagtt tccaaccaaa tttgtcgatt tttgaaacaa acgaaaaatc    480

gagaattttt cgttttacga tatttcaaaa aaaattcgat ttttcgaaaa ttagcttaaa    540

ttttggccat tgttcttctt tttagtataa tttttttttg ttttttctca tcaatataca    600

caaaattaga tttaagaaaa ataatatttt atagttaatt ttctgaaaaa tttttccgat    660

tgttcgattt tccctcaaaa aatcaaaaaa caccaaaaaa aaaaccattt caaaatatgg    720

aaaatgttat taatttctgg ctggagacaa cttttttctc aaaattttcc taaaagtaac    780

cccaaaactt ttttttcaga caaccagaca cctcttcggc ccaaagtctc ggcgttgacg    840

gtgacgattt accggtttat ggtccaatgc caaaagaacc cgacgagaag cttcatccat    900

ggaaatatga gagaaaagat tccggagttc gaaaattgtg agtttatcct tcttcccatt    960

tcaaattttt aaaccatgta aaaagtattc agtttccgct tcttcaaaga ctttggagcg   1020
```

-continued

```
acggcgtccc cccgccgagg atcttctgca aacgcgtctc ctcgactacc ggctcgtgcg   1080
atcccaccat ccctcaattg atgatcatgg ctccgatgct tttgccagtt catatttttct  1140
tttctgcaat ggttttcatg tttcagtgtc tgtgacaccc ctccattctc tctaatcatc   1200
acatttttttg atctcactac tagtcaaacc ccatttcagc ttcaaaagta ttttttttt   1260
tttaaatttg tacgacatgt ctctcactct ctgcctgctc cttgatgatt atgatcgact   1320
atcgatcgat tttaggctca atttcgcttc caaaaaaaat ctattcattt tccccgtgtt   1380
ttacccttcc ctgtctctta ttttttgctc ttcatgtggc atatatatgt aattatgtgt   1440
gttgtcatac tttttgtcat cttttttgaa atatcgaaat taacaaagaa tttctcacaa   1500
aaattcacag ttgttttcaa ttttccacac acaaaacatt tttcaaaact atcacggaaa   1560
gcttctgctg ctgcgtggtc agagattttc ggagcaaaag agcaatgtgt aacactggcg   1620
ctctggagtg cgggaaggaa gaaaaacgaa aattcagaca gctgttgagc tgaacaattc   1680
tttgcgttga aaatactgat ctggttcgca ttttttacgg atttttatta tgaattttgg   1740
agatttttgg acatttctgc actattttac cggaaaactt gctatttcaa atcttaaaag   1800
agcacagaaa tttaaattta tattaatatg cattttcact ggagtttgaa cgctttttta   1860
gttattttag tcattaaaaa actatggatt tgagctgaca ttttttgaaa ttcgaaatta   1920
atttgtggct tttctgtttt ttttttgaaa aatgttttac attaaaataa ttaaataaac   1980
taaatttcac atttctgcta atattttatg aaaactttat gacaaaaacc ctgtaaaaat   2040
gcgaaattta gacttttacg atataaaaat ttaaaaaaac tggtttgtcc gagaggagta   2100
cacgccggat gcgctttgcg acttttgcgc ggtaattcaa atttgaattt tccgcatagt   2160
tgaatttagc gtattcttag ggcaaattaa cagaaaaaat gtatgaaatt tcagaaaatg   2220
ggtgattcaa acacctggga ccttgttgga gagcagcagc aacggaagaa aagtagatca   2280
ccgtcaagag caagccgtgt ggattcggaa gtaattttaa gcgcattcaa tatgtactaa   2340
ttaaaggtgc atacactttc agctacttgt cggtgttgaa aacgcggctg aacttgaagc   2400
tcttggccta ggaaaagagc agctggaaga agaagccaga cggcacaaaa agcagcggag   2460
caagtcgccg gctctcgaga atattcgaaa aacttcgatt catcttttgc aaaaatttgg   2520
agcgattcca aaaaagaagg atgatagtgt tttacttttt agatttcatg atattcctga   2580
tattcccttg gaatctttat gcatcaggtg agaaagaagt tgcaaaattt attttgaaaa   2640
ttcgaaaaat aatttcagac cgaaagagtt tttcgaggag cccaaagtat tttcctttcg   2700
agacatgggc agggaacagc agaaggcaga ggttaatgag aagtggtaag gggtttttga   2760
atttgcgcgt caaattcggt gtttgcattt tccaagctcg agcgacaatg gccgaggatt   2820
tttctcggcc atatagaaaa accgatctct tgcgtttcta agttgctaca gccgcgaaaa   2880
aaaacatcgg tggccgagtt ttccaatttt cccggccacg aatcaaaatt cggaatttat   2940
tttcagctcc tacttattcc gtggcacctc attcgaccac gacgatcatt tcgaacttcc   3000
cactgaaaca ggccgtgttc cagaatatga tcatttttgc ccgattcatg gatccaggcg   3060
aagacttcca cgtaataaat tggtcacaat gcaaactctc atgcattcgg tagatgatga   3120
agataatgaa gatttggctt atatttatgg gttagttttc agagaaattt gaatgaaaat   3180
tttaatcggt tttcaggcac gactttctgg cgaaattggt taggaagaag aagcgagaaa   3240
tgatgagtgg aacggaaaaa gaaagagcta ataagattaa aaggaaaatt atggtaattt   3300
tcaaaacgtg gctgcgaaat gggaaaacta ggccaccaca gaaaactagg ccaccagaga   3360
aaactaggcc gctagaaaga taaactaggc cactagaacg ataaactaga ccgcttgaaa   3420
```

-continued

```
aactaggcca cgatcaaaaa agctactact attgaaaaaa aaaactagac cactggacaa   3480
aaagctaggc cgttcgaaaa aagacactag aaaataacta ggcagttttt aattaatttc   3540
attaattaat tgcaattaat caagtttcaa aaaatgcgaa aactcggcca ccgacttttt   3600
tcgcggccgc gtggttccaa actatgaaaa aaataacagc aaagtcggtg gcctagtttt   3660
attgtctctt ccaaatgaca catacgattg taaaaatggc tgggaaaatc agtggcctag   3720
ttttttcta gtggcctata atttctctag cggcctagtc ttgattgcta gtggcctagt   3780
tttttttttt ttctggtggc cgagttttcc tttcaaatta ggatacttag gatatatagt   3840
ggccgagttt cctgttttcg ccacttcaac tagaccaact aatcgaatca ttttcagtca   3900
aatctctgga ttctgtccgt ggcttttctc ttcctgttca ctgcatttaa cggactccaa   3960
aatcttcaaa cttccgtcaa tggagatctc ggatctgata gtttagtgta agaacgtttt   4020
gaatttcaat ttgaaaaata ataatttttc agagccctat atttatcact tgccatatca   4080
tcattatttg ttccatcatt tatgataaat cgcctcgggt gcaaattaac attccttatt   4140
gcaatcttcg tgtattttct atacattgtc attaatttga ggccgacgta agtttttgcg   4200
tttttgagc gcttgtaact cagaaactaa aatagttagc aaaaaactgt caactaacaa   4260
aatgttaatc gatttttgat ctacattttg ctagttgaca actttttgat atctttcacc   4320
tataagaagt tatgtgcatt tgaagagcta gagatataaa aaatttattg ccatttattt   4380
ccgtttagaa ctttttgctg tttagcattg ttagttctaa gctacgtggc tttttccaga   4440
tactcttcta tgatccctgc ttcaatattc tgtggaatcg cggcttcatg tatctgggga   4500
gccaaatgcg cgtacattac agaaatggga attcgatatg ctagcctgaa ctttgaaagt   4560
cagactactg ttattgttag gtaatgggct gattttctaa acctttttca agcttttcaa   4620
gcttttaatc aagccaaatt cagatttttc ggatattttt tcatgattgt acactgcgga   4680
caagtcgtcg gaaatatggt atcctcttat atttttacac tgtcctattc gcaagcccta   4740
cgcggtcctg aagattctat atacgatagg tttgccgaaa tttttttttg aagttttaaa   4800
atttcaattt tccagctgtg gctaccagtt tccaaagaat ttatcagatc ttaccgagtt   4860
ggcggagagc aatcttgctc ggccaccaca gaaagtttat gtagcaggtg agcctacata   4920
cctacatacc tacataccta catacctaca tatctacaaa cctacatacc tacataccta   4980
catacctaca tacctaccta cctataccca attttttttt aaatttcagt ttgtctggca   5040
tacctcgctt gtgtaataat cagtggaatg ataatgagca tgttcctgaa tgctttggcc   5100
aaagatgctc ggaacaggtt tgcctacttc cagtcttctc ttaaatttgg ctctgaggtt   5160
tcagaaaaat ggctcaaaag ttcaactcgg aaattttcta cctcatgctc aaacatttaa   5220
tcaatataaa gttcatgttg ttggtgccgt tgacgatttt caatggtttg gagcaagctt   5280
ttctagttgg agtttataca aaggttagtg ttacgtggcc gttaagaggg taaactcggc   5340
cacgtcacta aatcgcaaaa ctgaaaattt tcttccaggc attcgtcgga tgtggccttg   5400
gaatttggca aataggcttt gtgatggcct gcttcggaat ctccgacgca gtctgttccc   5460
tagtcttcgg gccactgatc aagcttttcg gtcggatgcc tctttttgtt ttcggagcag   5520
tagtgaatct attaatgatt gttacactta tggtatgatg caccatattt gacgcgcaat   5580
ttcatatctc ctctcaggtt tggccactaa atgcagccga cactcaaata ttctacgtag   5640
tcgctgcaat gtggggtatg gcagatggtg tctggaatac tcagattaat ggattttggg   5700
ttgcacttgt tggaagacag tctctacagt ttgcattcac taaatatcga ttttgggaat   5760
```

-continued

```
ctcttggaat tgcgattgga tttgcgttga ttcggtgaat tttttttttg gcttttgccg   5820
cattaaaaat ttatggggac gcatccattt tgtaatcgat gtggaaacgc gctccacggg   5880
caattgaaaa cgctccgccc cctacagtag ggtctcgtta ggtagttgtg gtgggacctt   5940
gtaaattcaa actttttcaa ttagtttcgc cgatttccat gcatttttcg tttttttttgt   6000
tatattttcc gttctttgta aggatttttt cgccgaaatt gatgaaataa agtggaattt   6060
aaaaattgaa ctatttttta aactaaaaac gtatttttaa acataattag tggaaaaaat   6120
gacgaaaaac atttttagaa acacaaaaaa catttaaaac gttaaaattc gcgttttggt   6180
ccccaatacc taacgagacc cagcttttgg gggcaggaca tttgcattta gccgtggagc   6240
acgcttgcac ctcaatctga ctattcgcat tttttgcgtc tccataataa tgttggccgt   6300
gaaaaaaaca ggtggccgag ttttctttta aatttcccgg ccacgctaga tttaacttga   6360
aaaataattg aattttcaga cacgtcacag ttgaaatata tttgctgata acattcttca   6420
tgctactttt aggaatgtgc ggatttttag caattgaaaa tttcgatcac attattgtaa   6480
ggctgattcg aagaaattaa ttttttctaa ttttaaattt tccagaaatt ttggcatcac   6540
ttaattcaca cgtcatgtcc agagaaggaa ccgttggatg atagaaattc agattttgaa   6600
tgaaaataat taaaaatcaa aaaaatcagt taataaattc gtactttatg ttttattaaa   6660
aattcgaaaa gtcgagaagt ataacaaaat gcagtaaaat gagaaatatg tgataaaaat   6720
taataaaacg tggcgggtgg ctaattgagt ttcaaattgc tagactctgc gtttttcttg   6780
aaaattttca gaatttccag tccatgctca gccatcattt cgggactcga cattccggtg   6840
tcgtagagag attttagaag aaatctggaa aaatttaata ggattaagcc gtatgtgtcg   6900
atttacgcaa gtcgtgtact cctcgagaag aagaagaaca cagttttcgg ctaaaattct   6960
tgatttggaa ctgtttgagc taattttttc tgtattcgag tttagagcac cgttttgtag   7020
ttacagtagt tttcgtgacg ggacccaaat tggtttagca cccgtcgagc tgtattcaaa   7080
attcctgctg aaaatagaaa aaggattttt taatcatgtt ttctatactt tttttgtttt   7140
ttgaagtttt ttacagcaaa agaattggcg aagatggttc aaaatagatc aaaatatacc   7200
caaaagttgt gaatttttaa aaataaaatg caaacttctc ttcgaggagt acacttttta   7260
tgttgggaat tttcctcacg tcagaacatt tttcttatca ccaggtgtgc attggatatt   7320
cttatcagcc aatactaatt tatcatgaac actttgagat ggctgagcga cggttggacg   7380
gagacagaat gtcgttcgga aatttatcat tggacggtag aactctaatg cactgaaaaa   7440
attattattt tcatttcatt attttcaatt ttccagccgt actctgcata aatccatttt   7500
ctcagattgg cggcgttcac cgctgatacg aaataatctc ttttactctt ccagatttgt   7560
ttacgccgag ccaatggata ctcttcatct attccaagtt ccaagtcgag ttgatcccaa   7620
gcacggcgag acaaattcga attccgatga caaatcaggc gttgatccca taggactaaa   7680
aagggaaatt tttggaaaaa cttcttgatt tcctgactta ctaggccttt tccgaactgc   7740
atatataata tcgtacactt tttcaggctc cgcgtaatcg atttttgtag attggcggac   7800
ccgattgtac ttaaaatact tgtctgagcg tgtttgcaca gtcaaatcac tgaaaaaagg   7860
ataaaaaaga aatctgataa taaatgtttt aattcatact ttccatcatt cttgagcata   7920
tcggctgtaa ttgaaggaat gtacatcgaa ttgttggatg ctcgataata aactgtttcg   7980
ggaataattc cggcatcagt tttcgctttt aattcttcgt aatttgtctg aaatctttga   8040
atagaattga aacgaatatt ataaaaagct gtaccggaat attgcgacaa gatcttctag   8100
ttggtccaag acgaagtttc ttcgattcgc tggcgctctg aaaaaatgtt tgatttgtca   8160
```

-continued

```
tcattttttc tagttttcag tgaaactttt gtcatcattt attagttttt tcttgtgcct   8220
gattgaattg attgaaacta catataaata atcactattt taattttatt gcccactcgc   8280
gctctttttg gttttttttct aataaaattg tctttcttct ctgcgcactc cactattgac   8340
caaatcagtg tttctttcta tttgtcattg ccccgacact gcgaagaacg ttcgcgattg   8400
ttctttgtct tttttacctc tcttaattcc tccgttgtaa ttgatttcaa gtcgtcatcg   8460
agttgttgaa aatcggcaaa cacttttcgc ttcactattc ggccgcttcg agatttttca   8520
acttctgaaa aattgagaga ttcatataga ccatttttca acatttacct gtcatttttt   8580
attccagcgt gcgaatccgt ttggaaaatt gagcggaatt tttaatttcc aaaaaaactt   8640
ctaaatttca aattttaaac tcttcgcgcg ctgaaaaagg ggcggagttt tcaattcgca   8700
aaatgggcgc gagctatttg caacttgggc gcacaattta gtccttgatg tttgtttatt   8760
ttttgctgat caaatgtcta aaaacttctg tgaacccttc tgaatgctcc gatttcgctg   8820
cattttgagc acttcgaggt attaaattgt tactttttgg tttaaaaaaa gtttttgtag   8880
tctttgtgga gtcaaatttc cataaaacct ctcgaatttc ggaagaaggg cggtcacatg   8940
tttgtagtcg cgctttgcta tctttgtaat ttgtcatcgt ttttgcgtca gtcgattttg   9000
agtatttcat tcgaaaaata aactttaaag tccacttcgc gactgaaaag aaataaagct   9060
ttgatttttc tgcgaatttt caatcgcgcc tctctttcga tgttcttaca agttctgtta   9120
ttttccaact tttaattatt aaaattcgag ttccaggtcg atcatgtctg gcgtcaagga   9180
gttcgactat ttggtgattg gtggaggatc tggaggtatc gcttctgctc ggcgtgctcg   9240
tgaattcgga gtttccgtcg ggctcatcga atctggacgt ctcggaggaa cttgcgtcaa   9300
tgttggatgt gttccgaaga aagttatgta caattgctct ctccacgccg aattcatccg   9360
ggaccacgct gattacggat ttgatgtgac gcttaacaag tttgattgga agtgagtaat   9420
ttttaattag tttaatcaaa taattcttaa ttgttttgtt ttttagagtg atcaaaaaat   9480
cgcgagatga gtacatcaaa cgactcaatg gtctttatga gagtggactg aaaggatcct   9540
cagtcgaata tattcgagga cgtgcaactt ttgcagaaga cggaactgtt gaggtcaacg   9600
gagcgaagta tcgtggaaag aacacgctca tcgctgttgg aggaaagcca accattccaa   9660
acatcaaagg agccgaacac ggtattgatt ccgacggatt cttcgatctc gaagatctgc   9720
caagccggac cgttgtcgtt ggagctggtt atattgccgt agagattgct ggagttctcg   9780
caaatcttgg ttcagacacg catcttctta ttcgttacga taaggtacca tgaggaacat   9840
ggaaactttt caagtttaac taaataattt tcaggttctc cgcacatttg acaaaatgct   9900
cagcgatgaa cttactgctg atatggacga ggaaacgaat ccacttcact tgcacaaaaa   9960
tactcaagtc acagaagtaa tcaaaggaga tgatggtctt ttgacaatca agacaacgac  10020
tggagtcatc gaaaaggttc agactttgat ttgggccatc ggaagagatc cactgacaaa  10080
agagcttaat ctggaacgtg ttggagtgaa aaccgacaaa tctgggcata ttattgtcga  10140
tgagtaccag aacacatctg ctccaggaat tttgtctgtt ggagatgata ctggaaagtt  10200
ccttctcaca ccagtcgcaa ttgctgccgg acgtcgactc tctcatcgtc tgttcaatgg  10260
tgaaactgat aataagttga cttatgagaa cattgccaca gtggttttca gtcatccact  10320
tattggaacc gtcggactca cggaaggtat aatatcttta aaatttaatt ctttgtgtca  10380
aatttaatcc ccaaaatttc agctgaggcc gttgaaaagt acggaaaaga cgaagttacc  10440
ctctacaaat ctcgcttcaa tccaatgttg ttcgcagtca ccaagcacaa ggagaaggcc  10500
```

-continued

```
gcgatgaagc ttgtttgtgt cggaaaagac gagaaagtcg tcggagtcca tgttttcgga  10560
gttggatccg atgagatgct ccaaggattc gctgttgctg tcacaatggg cgccacgaag  10620
aaacaattcg atcagactgt cgcgattcac ccaacttctg ccgaagagct cgttactatg  10680
cgaggaggtg tgaagccgga ataatttttt atttatttat tacattttta aatttggatc  10740
aatttctttt gactttcttg tagataaaac attgcaaaat ttaaaatgca tggcaaaaaa  10800
attatttaca ggttatgcaa aaaaatctaa ttatggtgag tgctacatat taacccgatg  10860
ggtagatttt ggtaggaaag gattttcaga attaaaactg caattgagac tattcgagaa  10920
gctcatattc gtcatcggcg gccacttctg attttttagg ttctcgtcgc ctccgtcgga  10980
tggttttctg caaaatttgg agttttttgg aaattattaa aaagaagaaa aaactacttt  11040
cggagcatcc aaatcgaatt cctcatcact ggattccgat ccattgattg ctgagaattg  11100
aagacctcgt tcgaattcga attcttcttc tgaaatttat taactaaaat aatttaaaga  11160
gtctctgaaa ataacctgga atcggcgaag aagacaattc cgattgaata tcttcattat  11220
catcatcatc cacatgattc tcatcgagat cggtttcatc gttcacttct ggaagaaatc  11280
cttcgagttc cacatcgctt tcttctgaaa aatcgatatt taaagtaaaa aattgcttaa  11340
caaagtgaaa acgcgctcca atgccaactt tatatagtcc accctattct cgtgggtctc  11400
gcctggaatt tctagctttt tgtcgttttt taaaacattt ttcggtagtt ttaatcattt  11460
ctatgtcaaa attggttaat taaaaatttt ttagattcat ttttacatgg aaatcagaaa  11520
aatagaggaa aagtgtaaaa agcaattttt accattttaa aaaattttgt ctactccttc  11580
gtttctcgta aaaaagtttt tttttccgaa ttaattaact cgttttcaat aatttttaga  11640
ttaattcaaa caggaaaaat agggttgaaa aaaaaatttt tgtctaaaaa gccctttttta  11700
tttttatttt aatgtaaaaa atgatcaaaa aatcgctttt ccgtagtgta aatttccgtt  11760
tttttccaga cgagacccaa ataaaagggg cagatcgatg ggagtttgca ttggagcgcg  11820
tttcataaga cgcaccacaa aatggatttt tctcgggaat atgatcgata actgtctcac  11880
agactgggcc aattacgtgg attaatgcac ttgtctcgat gattttatat cgactatgga  11940
gataatttac aatgggctga aaaattgaat ttttaaaata aaattaaaaa aaattacctc  12000
caggagcaag tggtacacaa aaatcgagac ctgcttcccc acctcaacca tcagacaaca  12060
aattggccag agaatcgagt ctcgcacgga aattgcaatt cgatgaaggg tgtcgcggag  12120
ccagcaacgg agtttttcaa attggcacaa taggaatctg gaattttttt gtttttttctc  12180
aattacttta aaagtataga ataatgaacc tagaactctc aaactaaccc cttaaccgga  12240
acccaaatat gcttataagc caatgctcca agtgatttca actgcttaac actgaatttc  12300
cagagtggtg ggaaccagtg agcacagaaa atatagacaa acacgaaaca aagttgatcg  12360
aaaaggtagc ggaggggaac accgatctga aaaatcttgt gctaatctgt ataattctat  12420
tgtagtaatg ggggaacaca ggccaaacaa tactcaaatt ggcccccaaa agaacggaat  12480
ttattagcct ttttcaaaat tttgtcgagt ttttttgctt attattctcg tttatctgac  12540
gatttttcgt tgatttaagt acattttgag ctgattattc aaagaatcaa ataaaattag  12600
ggtttgaggc cattataaac atagaaaaga aggcaataga aaattttcta acaatttgag  12660
gaaattatga acaaaaaaaa taggaacaat gaaaaattat gacggcattg aatgagcaaa  12720
aaagaagcag ggaaaatttc ataatagaac tgataaaaaa cgaaattaaa atgcttacat  12780
tcaatttcag ccactctttc aacgtcggcc accattctgc acaaaaccaa tatctgagga  12840
attgacgaat tctctgagca actcgttttg ttcgttctac gatcgccacg tggatccagt  12900
```

-continued

```
ttttgatacc attgacgagt tcacgacatg attcacggaa attgaagata aaatgcttta  12960
cgtaggcgat tagagctgta aaaagagagg gggttttcga ttttttaaag aaaatatttc  13020
aaattttttg aaaaattttt tttcaataaa ttatgttttt ttttcctgaa aattaatagc  13080
tttacgggaa tttttcacaa aaaatttgaa acatttttgc ttcgaattga ttttttctgg  13140
aaaactggca ataaatagat tcgattttcg atttttcgga aaacttttaa tttttaaaaa  13200
tgttcataaa taaataattt taaaaatccc aaaaaaatat agtgtttcgg aattttaaat  13260
taaaaaattg gaaaatctaa aagttaccgt atttttttga tttttcggga agagaaaatt  13320
ccaatttcca ttaatattgt caattttttt cataaaaaaa tattcttaag tttctcatat  13380
ttccggaatt ggtttttgaa aacaaaaaat ttaatgtttt tatttggaaa attttttttat  13440
ttttttttatt ttcaattttt caaataatgt acttattgcc aattttaaaa tttatttcaa  13500
tgaaattttc atttttcttt agataacaaa catttacaaa atttcgtaca aaaatcatag  13560
ttttttccat tttccgattt tctccgaaaa ttcaatattt ttgtgaaaaa tatttttaaa  13620
aacttacgtg gaacccatcg gaagagcaca atatatttag tatactcata tacagtaaca  13680
actggagtaa taataagata ttgaatccaa cttccaaacc aggaaactgt ccgccgcgtt  13740
gctgacgcta ttttcgagtt gacttcgttg tgctcccaca ctggatttac aaggagacac  13800
gctactgaaa atggaaaatt ttttttttgtt ttttttaatc taagagactt agtattgcgc  13860
gacatatctc gtaacgaaat ctacagtaag tgactttaag tgactactgt agcgcctgtg  13920
tcgatttacg atttacgggc tcgagtttcg aaatgaattg gaatcttttg aaaatcgaca  13980
caagcactac agtagtaatt caaagagtta ctgtagtttt cgctacgaga tattttgcgc  14040
gtcaaatatg ttgcacaata cgcattctca aaatttcatg tttttataat acttacaagt  14100
tgcataagca gcgtaacaag ccaaccgaac ttgctcagca cgtaataaat gaatgctgta  14160
gactgatcca ccgactgaca gcgtctataa ataaacatta atttttagtc ttttataatc  14220
ggattaaaaa atggatttac tctgaatata gattgaaatg gccacattaa aagatgtgtg  14280
atgattgaac gatcatttga agaggaaagt agaatatccc aggcaaaaac tccggcggat  14340
gcagttgcta gaagagcttc ttggatacga ggatcacagt agatcacacc gatcctgaaa  14400
gaaagaggat tttttaaaa tgaaattggt tgaattttag gatttttaag tgcaaaattt  14460
tggttttttt ttcagtttgt tgtggttttt tcagtgaaaa tatagatttt ttgcttagtt  14520
atcgcagaaa tgatgatttt tctttgaaaa tttggtgttt ttttattcat tgcaaaaatt  14580
ggtttttttt tttcattttt ttaaaatttt ctatgaaatt tttttaaaat tatttattgc  14640
agaaatttga tgttttccgc cagattttcg cagagttcca tattttttga ttaattaaca  14700
aattcacgtg tgtattaccc aaacgcaaaa gtttacggta aaaaacggtc tcggcacgac  14760
aaatttttgt taaatgcgaa gagttgtgcg cctttaaaga gtactgtagt ttccaaagaa  14820
aatttcatcc atttttcata gttttttgaa cgatttctta aaaacttgtg tttttatagt  14880
tttatttaag ttgtaaaaaa acaatttttc tttttttttt aattgaaaaa ccataaaaat  14940
cgatgaaaat ttctcagaat tgtttaaaaa aagttttttt tcaactacag tatttttttaa  15000
aggcgcgcac ctttttgaat ttaacaaaaa tttgtcgtgt cgagaccggt tgccgtatat  15060
attgatttcc tgacaaaaat cacatgaaat ttctacggtg agcatggaaa aaaaaccatt  15120
tcaccacaaa aaatatagaa aagttgaaat tgactacagt aactttaaag gtacacacac  15180
taaaaccaac ttttgctgcg agacccaatc tcttaccaaa aagccgaatt aacagccatc  15240
```

-continued

```
aaatataatc cagtaagcgg attcctccat tcgatagttt ctcgatagac ttgatgaagt  15300
ctccggccac tttctcgtat ccgttccatc attttggagt ttaaattaaa attttaaaat  15360
ttcaacgaaa aaccaaaaaa agaaatcgat aactctcttc acatctgtta ttattttctt  15420
ttttgtcaac ctaaaaacag aacagttgtt tctttttttc tttgaaactc ataagagata  15480
gaatgggagc gatgagaaaa cgcttcggga attattgaat tattgcgaaa tcggcatttt  15540
tttacaaatt tttttatgag atctggaatc tggaaaaaaa gagaaaaaag atgttaaata  15600
gaatctcgga tcaaaacata aaaaaataaa ataaataatt tattcccatc tgcttcgttt  15660
tgaggaagag ctgctgctcg aagagccacc agaagctgaa gaagcctgtt gctgtgcaat  15720
ctttgcattc aattcatcca ctttcttttt ccattctggt cttggatctg atgctacttg  15780
ctgtggaaga tttgaagatt catttgtagg tcgttgaaat gttgtttgga atgatttctg  15840
aaatgcactt ttgagcattt gggctctatt ggctccggaa gctgggccac tgcttgaaga  15900
ggaggaggaa gaggatgacg tggcaaagct gaaaattcga tttttatgtt aaatgtggtg  15960
gggtggatga aattattttt ttaaatactg tcatttatta gaaatttttt ttgttgaatt  16020
ttttggaaat tgttgaatta tttttttaat tcctattcta tttaaaactc aatttcccac  16080
atttttaaac atgctccgta taaaaaactt gataatttct ctgaaaaatt tcctaaaaat  16140
caataattta aactttgtcg cgtaaaactt ctgaaaattt gattgactat gtttgaaatc  16200
aattatcaaa caaaaaaatt taagagaacc aaattttata gccgaaaacc cccaaaaatg  16260
tcgaaattag gccatttttt gcgggaattc aaagataaat cagcccgttt ttgtgggaaa  16320
attgaaaaaa aatcgtaaaa aatttagaat ttagattaac acttatattt ggctatttcg  16380
gtctattttc aattttttga agtgcaaata actctttttg aattaaaaaa tgattttctt  16440
tctttttcga aatatagttc aaaatttttg ccactttttt cttttttttta gtaaaaaatt  16500
tatttttttt cttcagcacc aacggtgtcg gtttttcgaa ttttgaaaac cgataatttt  16560
cgttttattt ctaatttccg atatttagta aaattttccg atttttaaaa aaaatcttaa  16620
cattttgatc tcttttctcc taaattttta tgtgtttttt tcttatcaat ataaaataaa  16680
attagatgaa aatttttaaa aatattttat ggttaattct ctgaattttt ttattttaat  16740
ttttcggaac atcaaatact caaaaattgt tagtttttcg atttcccttc aaaaaaatgg  16800
aaaaacgaca catttcttta attttcaaaa tataattttt cgattttccg gaaaatccgt  16860
aaactacaat ttttacattt tccttgtctc ggtagctatt ttttttatta aaaaattaat  16920
taaaaattta tacctttgtg catttctgat cattccatca actgtctgat tccctccacc  16980
tctacaactt ttttgctctt ttaatggatc aaattgtgct ccagtggcac ctcctccaac  17040
ttgtctaact tttggtgtat atccaagacc cattcttcca cgtgtctgtg ttccagtact  17100
tggtcctcca ttcccagctc tttgtcctct aaaccatgaa ctcttcattg caagatccat  17160
taaaggtttt ggtacttctt gtgatacact ttccagattt ttgaccaaat gtccgaccat  17220
ttcaatgtct ttttcagtaa caagagtgta tgctgttcct ttgtgaccag ctcttccagt  17280
tcttccaatt cgatgaacat gagtatcgat gtcacgagcc atatcgaaat tgattacggt  17340
tcgaatttca gaaatatcca gtccgcgtgc tgaaaattta attttttgat cggaaaatta  17400
gggaaaattg attaaaaacc ttagatttta gatttttaga actttaaaaa ttttttttacg  17460
gtttccaaaa ttttcaaaaa cttgaaaatc gccaattttt aaatgttttt attggagaaa  17520
atatttgttt tttttttcct atttttttcc gaaaaaatat attcaatttt ttaaaaaaaa  17580
tttcaataaa tcgagcaatt tttctcgact tttcgatgta aaaaaaaacg aaactttaaa  17640
```

-continued

```
agatttttag gaaatttttc aaaaagtcaa aatattttta tttttgttcc cgaatttcgt  17700
ttttttttc aatcagattt tttggttaaa aatctatatt tttttctttt tttccgaaaa  17760
aaaattaatt tttttggaga aatctcaata aatcgagcaa tttttctcga catttcaatg  17820
taaaaaaaaa acgaaaattt tagatttttt cataaatttg ctaaaatttt gaaaaaagtc  17880
aaaatatttc aatttttgtt gtcttaattt ttattaaaat ttaattgtgt taaaaaatcc  17940
cgaatttcat tttttttgta ttttttttctg attttcctgt taaaaatcta tactttcttt  18000
cgttccaaaa ataatttcaa ttaaaaaatt gggcgattct ttttcaattt tttcaattaa  18060
aaaaaattct caatatccgg ttcttttttg atttttgtta acatttttta ttttagacaa  18120
ccgaaaatag gatttttgat tttacaaaaa aataaattaa ttcacttttt acagaaatat  18180
actttttcgt tatttttttt cacatttttt aaattaaaat attatatttt taagattttt  18240
ggaattttcg aacttcaaaa aaaaattccc agtaaaacta ttacctgcca catcagttgc  18300
cacgagaatt tgcgattttt tccggaattt caataaattt tcatttctct ctgcttgtag  18360
catatctcca tgtagaagga caatgtcgaa atctttcatt ttcaactttt tcgcgacgtc  18420
ttccgaatcc aattttttcg tgacaaaaat tagcactttt ccgactgaaa aatggtttaa  18480
attatggaaa atttgataat aataaaaatc ttacgagaag caaattccac taaatttcga  18540
ataagccaat gcaatttaac atcttgattt tgcattacaa aaactttttg ttcaatatca  18600
gcattcgctt ctccaacttc tccttgtaca attcgtacgg gatctacgag agcatctcgg  18660
gcgagtcgtt ccactttttg tttaaaagtc gcactgaaca ttaagcattg acgatccggg  18720
cggacgtgat cggatattga ttttacttga gcctctggaa taatggaaat tcgatttttt  18780
ttttcaaatt ttcatctttt tttttttgat aattgtatat ttaattgctg tgaatttagt  18840
aaccaaggaa ttccaaaaaa ttccaaaaaa aaaaacaagc tttgtggttt ttttttcaaa  18900
gaaaaatttg gctttaacgg tttttaaggt ttttttttcaa aaattattca tttgaatttg  18960
ctacgtgtta agatgaaaaa tgttacggca acgaatccat aatcgagcca tttttctggt  19020
ttaaaaactc tcacaaaact caatgttttt ggttcgaaat ttttcgtcgc ggtcatgttt  19080
cgatttacga ggctcgtggt gggcaaacga ctttttccgg caaatcggca aattgccgga  19140
attgaatttt ccggcacttt gacgggattg aaaatttccg gcaaatcgac aattttccga  19200
aaatgaaaat ttccagcaaa tcggcaaact gccggaatcg aaaatttccg gcaaatcggc  19260
aaattgccgg aattgaaaat ttatggcaaa tcggcaaatt gccggaattg aagtttcggg  19320
aaaatcggta attttgttga aatggaaaaa ttccggcaaa tcggcaagtt gccggaattg  19380
aaaatttccg gcaaaccgac aaattgccgg aatttaaaag ttccggcaaa tcggaagatt  19440
gccggaattt gaaatttccg gcaaattacc ggaattaaaa tttcgggaaa gtcggcaatt  19500
ttgccgaaaa ggaaaatttc cggcaaatcg gcaattttaa atttgtcggt ttccactggc  19560
tcgtgtactc ctcgaggagg aaattcaatt cgggaaaata cacgagctgc gtaaatcgac  19620
atacggccat ttctataagt ttttttcaaa aaaatatacc aaatcccata tcaaacatgc  19680
gatcagcttc atcaaaaact aaaaaagttg tccgcaggaa attggtggct cccatcttca  19740
ctaaatcgat gattcgaccc tggaaaagcc ttttgaaatt taaaaataaa tatttttctc  19800
aactaaccgg tgtacaaaca accatttcag ctccttcatt ctgtaattca tttgattgtt  19860
cccatttact acctccacca tatgcacaaa ttggattaat attgtaaact ttgcagaatt  19920
ttttggcctc ttggaatacc tggaaaattt attttttata tttcaagttt tttggttgaa  19980
```

-continued

```
tttccaaaaa cctgaattgc caattctctc gtcggaacca caataactgc aaccgggcct  20040
tctccagcct tcaaatcggg ttgatccata atatgaacga ttgcaggcca caaataggcc  20100
gcagtctttc ctgatccggt tttggcaatt cctagaacat ctcttccaga taatgcagag  20160
gggatcgcct gaaaatgtta atttttttgt cgataaatta cagatcgtcg atttgccgga  20220
aattttgatt ttcggaaaat tgtcggtttg ccggaaattt tcaattccgg caaggaaaca  20280
ttcataggat gcgtacaatt ttgccgatta aaattgaatt attccgtgac aatgtgcaaa  20340
cccacagttt gccgaaaatc gaaatttccg gcaaatcggc aaaaaaatct gaaaaatcaa  20400
tattcaccat ggcctgaatc ggagtcggct gctcatattc actcttccga attgcttcca  20460
ttaacagctt atcaaatgaa aaatgagcaa acgagcaaac tggacgtggc ggcttgaggc  20520
ctccaactcg aagattcatt gtattttgaa ggcgaattac atccatatag tgtaagcgtc  20580
tgaaaatttc ttgattgata atagaaattt tgctccaaaa ctacggtaac cggtctcgaa  20640
acgacttgtt aaatgcaaaa aagtgtgtgc gcctttaaag aatactgtaa tttcaaactt  20700
ctattgctgt ggaatttttt taatcgattt ttcatagttt atgaaaaatc gataaaaaat  20760
tccacagtaa ttaacgtcta cagtactcta taaaagcgca cgaacttttt ttgtaatcag  20820
caaaaatgtc gcgtcgagac ccaatttttt tcagaaaatg cacagaattg gcttatttca  20880
acatgataat cgaacttttt cgatttaaaa ttgatataaa aatgtagaaa gcgaggtttt  20940
ctatctgaaa ataatattta tttttgttga caaacttgaa aattaccgtt cgctgaaatt  21000
tttttaacgg caccatttga ggtatttttc aagattttca tcaaaaataa atgttatttt  21060
cagatagaaa accttgtttc ctacattttt atatcagttt tagttcgaaa aagttcgatt  21120
attctgttga aataagccaa ttttgtgaat ttgccgcgaa aaaaaatgtc ttatcctgaa  21180
cccacttaat atcctcatgc tcctcataaa agtttttatt aaacttttga tattgaatct  21240
gtgaatgatc gatatctggc aatggatcga taaccttttt ccatgaccaa ataatatttc  21300
catcttcatc atattccaat tgctcatcat catttcgtg tttctctttg tactcttcca  21360
tgaatctgga aaacttttat attgtttaat atttgatttt aaattcatga attaattcaa  21420
aatttcctgt acaaacttga atagagattc ctgcatatcc tcctcatcaa tatctgctct  21480
tccaagccct tttttactcg gatcctccgt atcttttccc tctttccgat ctttctcttt  21540
ttgctccgaa actttttat cactggaagc ctgcttttcg attccggcca taaatgcgtc  21600
gagctcatct tcttcatcat cgtcatcggc ggcaagtttt gaggaggaag aagcgggctt  21660
ttcatcatct gagccgcctt ctaaatatct aaatttgaaa ttattaattt tctttttttt  21720
tttttgaaaa aaaaacctac tcatcatcat aaatccgttt ccttcttgat tgtttctcag  21780
acgtcgagcc ataagccata agatttgcgt actaaattaa taataatcca gtgaaaagtt  21840
gaaaattttt aatttttca tgaaaactaa aaacctcttg ttccttcttc atttcttgct  21900
cttttcgatt tgacaagaga atattccgat ttggtggtgg aacaggcgca tttccgactg  21960
ttaaagctgc aggaggaggt acattattca tacttttacc atctgagaac aataaaattc  22020
atttaatacg tgaaaatatc gatttaccac tcaaactgga ggttcccgaa ctctttgcgc  22080
ttacaaatcg attttgatat cctcctgaat attttccacg ccacattttt gcctgaaaac  22140
ataataaatt ttgtttattt tggaggaaaa tgatgtttaa acatgtttaa aaagtcgttt  22200
aatcgcagtc acagggagaa tgtgggcgtg gccttcgctt gcaacacgcc gcgcgcattt  22260
cgcaacgctg ccgcacgtag tttatgtatt gctgaattgt tgaagtacgt aactacagta  22320
agaaaatcat tttttccaca ttgaaatatt tcaaaaaaaa aagagagaaa atattatatt  22380
```

-continued

```
ttgaaattat aagaaatgtg ggtagaaaac acaaaaacta tgaccttaag gtcgcacgag  22440
aaaattatta aaaataatta caacggaaaa actacgagaa aattaccctt tcaccatgaa  22500
aaaaaaacaa tttttatttt ctcccgcgac tttaagttca caaaagtttt aaaatattag  22560
cgtggcacac taatccatta gttaaactct aagctcttgc tatataaggg gcagaaatac  22620
ggttttcaaa tcagtacgaa gttttggaaa cttctaatct tctggcagtg gcagtgggga  22680
gcagttggcc cgtggatggc ctgtgggtgg cctgtggatg tcctgtggat gtcctgtgga  22740
tggtcagtgc atggtcggtg gtgggatgtt gccgaacaac cagcggcatc aatggtcgtg  22800
tcggaagccg aggcctcgga cgaaaaacac gtggatccgg atggaatgga caggatcggg  22860
tggtagcagc ggacagtgac caatattgaa acgtaagttc gaatgctact tttcagacat  22920
ttctgaaata actttaacaa gaacgaagac gtacgctaac tatatgttaa ctcgtctttt  22980
tgttttgaaa tttgaagtaa ttttgaatac aacagtggca aaagttaact gagtgagcaa  23040
ttattctttg ttttttgaaa ttaaaaagtg tgcataacag ttcctaaaca attcgaattt  23100
cagcgtggca cactgagaat gtgaggagtc atggagcacg ttgatgaggg tggagctgga  23160
acgatcggtt ggacactgga gtaagctgat aggctttaaa aggtaatttt tagaaatgaa  23220
acaattttga aaatagtaac tgcgagaaaa aaccatttca cgcagaattt aattatttaa  23280
aacacacatt agttcctaaa caataccagt tttcagagtg gcacaataaa cggatgggcg  23340
gtcaggcatg tcgtcgagca agcagcgaag cgataccact ttggactggg aaccgaggag  23400
catgtggatg aggctggaat ggccgggtag ctgcagagga cagtggtcaa gaatagaatg  23460
tgagtttatc agttattttt cagaaaaatg tttaataaga atgaagacga gagctatact  23520
tagctattgg ttaatttgtc gttttgtttt gaaatttgga gagcattttg aatacaacaa  23580
tgacaaaagt taattgagtt agcaattcgt ctttatgttt agaaattgaa aaagtttaaa  23640
taaaaaactg cgcgagaaag tgtacataat agttccaaaa caattagaat ttcaggatga  23700
cacaataaac tgatggatac tggatgagta gagggacctc gagaaacgta gcgactgaaa  23760
gatggggcgg gggcagtgga gaacgtggat caggatagat tggagcgatc gggacggtgt  23820
gcaaatggca atggagtcag tcaaggatgg actttagtcc aacaaaggta acgagggttt  23880
gaaatgattt tgaaaaaaaa gtaaaataaa atttttgatg aaaattaaag acactaataa  23940
aatattattt tttattcgtc ttttccaaat cagtgtgtcc atttttaaag tgtctactgg  24000
aagcttcatt ttttgaattc cataaattaa aatttcattt ccaaatcagt gtgtccactt  24060
ttaaagtgtc cactggaagc ttcatttttt gaactccaga aatttaagtt tcatttccaa  24120
atcagtgtcc cgtggtggaa aaattttttt ttcctttttt ttgggatgaa aaaattcgca  24180
aaaaaaattt ttcatcccag aaaaaaaagg gggaaaaaag gttcagaaaa aacaaacaaa  24240
catttttgtc gctggatgga ctttagtcca acaaaggtaa cgagggtttg aaatgatttt  24300
gaaaaaaaag taaaataaaa tttttgatga aaattaaaga cactaataaa aatattattt  24360
ttattcgtct tttaatttta caaaattttc aataaaaatt taagacacta ataaaaatat  24420
tatttttatt cgtcttataa ttttagaaaa ttttcaataa aaatttaaga cactaataaa  24480
atattatttt tattcgtctt ttaattttag aaaattttca ataaaaatta aagacactaa  24540
taaaaatatg atttttattc gtcttataat tttagaaaat tttcaataaa aatttaagac  24600
actaataaaa tattattttt attcgtcttt taattttaga aaattttcaa taaaaattaa  24660
agacactaat aaaaatatga tttttattcg tcttttaatt ttagaaaatt ttcaataaaa  24720
```

-continued

```
attaaagaca ctaataaaat atgattttta tatatctttc tttctttctt taattcattt  24780
gtcttttttt tcaattttga aatagttatt taatttggtc aattttgttt cttaaataat  24840
cttgataata aaacatcgat taaaaatatg attttatgtt tcaaaaaatg aattcaaatt  24900
gaagaattga gtgtggagaa gggggcaaaa ttgtaatgta caccgttgga gagaagagaa  24960
gccggctata tcacggacta tatcggctgg aagtagggga aaaggagatt actgtatttc  25020
ccctaataga catgcacctt taaagtgcac ttctattaga taaaagctcg atttttatga  25080
aaaattataa aaaatttcga aaaaaggggt ggttgaaaag gggcaatgac cagaatcgag  25140
atgagaactg attttgattt ttttttgtta aatttttggt attgaaaaca aacgggtgcg  25200
gggcggttag ggtaacagaa gatcacagaa tttggcagaa agaagacgca aaaagtagac  25260
aaagctagtg gagccgatcg gaaaattgac aagaaaacga tggaatgaag gaataaaaga  25320
aacacttgtc gtcggctgat atcccgtttg agaagagaga gagagaggaa gagagaggat  25380
ttcagaaaga aaggaaaaat tgggatgttt tctggaagtt tggtcttaaa gtagtttaac  25440
ttttaaagac aaaattccca gaaaaggcca gagaaagaaa aagaaagagg tagagaggca  25500
aaaaaaatca tcgaaaatca tcaataaaat aattgaatgt agatccgaag actatgagag  25560
cacacatcga cagcaacccg cggattttcg tttcgtcagt gtttctggaa aaaaattaat  25620
ttactttgaa attttcgcaa aaactcgaag tgtagctgga ctatttacta tgtatttact  25680
atggtggaaa aaaataggtg gccgagtttt cttttttttta cggccacgat ctttctcacg  25740
ggcggctatt ttttattaga acttttcatt tacaatttga gtcatattta tcgatcaggg  25800
aacatgcaaa aataatttaa aatttagaat ttggaatttt tttagtcaaa aaagtgtgtg  25860
tcttctgaga ttcttctgag cttcttcaag cttctgatat tttttttttc aaaaaatatt  25920
acaaagttat acttgttagg gtttaaggta tttaaagcaa ataatcaata aattttgaaa  25980
ctacagtact cttcaaaggc gcacaccgtt tgtttttatt gaacatttgt cgcgtgccga  26040
ggcctctgga ataaaaatca caaaatttcg caccgatgta atatattaat tttatgattt  26100
gttaaaattg aaattttaga actttcgcat ttgaaaaacc ttttatgtga tttttaacta  26160
ttttaaattt aaaaaaatca gctcatgcga acgcgcttca gtaattagaa ataatcattt  26220
ttctgtcggt attttttaac tcaaattttt acaaaaaatg ttttacactc tccctaaatt  26280
tcaactttct agattctcaa gaaatctgcc aaaaagcatc acaagtactg agttcccatg  26340
ggaactgttg aattgtactc taaatatgtg tttttcccga gaatatggtg tattctttct  26400
tgtttttata agccccgagc actctaaaca tgtaaaaaat tccccgggga atcccatagg  26460
ctctggttac tccatctgtc agactaaact gtgttcacat taaattaggt caatttcctc  26520
tcaaaacacc tgcacaatcg aatcaaaact gaccacttga attaggttcc ggcaaatttt  26580
ccctagtaac caaatgcatg acggttgttt tgccgggcat tagctggagc gcgtgaagag  26640
ttacggaacc atgtagaaat cgaccgtgat agattaattt gagcatttga gcactttgta  26700
ctttatcttc ataccattct gaaaaataga attattcatt tgtgatagaa tttttttaaa  26760
aaattctgat cggccccgtc caaatcttgg cttcttttgt ttctatcgga tatttgtact  26820
gagaaataat ttgaaacaga aaccgagaac cagatggcaa ttttaaaaac ttaaaattca  26880
gagtcccgcc acgaaaacac cccgaaacac ctcagtttct gaaaacagga attaattttt  26940
cttcaaactg aaattcaaaa atttcgctaa tttcaaattc aaaaccagct aaaaattaat  27000
tttaaaaact gacaatatct acagattttc gagtaaacaa tcttttaggg tcccgccacg  27060
aaaacacctg aaggttctaa atatgttatt gtagactgaa aagcacatat ttcaggtggg  27120
```

-continued

```
aaattattaa agttcatcaa atttaagtac attttctgcc gaaaaaactg aaaaacttga  27180
aaaataaaat tttctgagaa gaaagttctt tcagagaata aagttagatt caaaaatttt  27240
atgaaaattt tttccaaatt ccattttgaa taaattgtac aatccctttg ggaaagtagg  27300
cgtaggcctc ctactgccta taattttaat gtttccctta ttcatttttt tttcaaattt  27360
ccataaaccg aagttgcaac tgctacaaca tgtctcgttt cgcacatatt tgcagacaca  27420
tacacctgac ctcctaagat cagtggaatt gtggtgttcc cccacaacct tctcaagacc  27480
cctctataag cctgtagcaa acaatagtct atgtttctcg gacatcgtct ttgtgtactg  27540
gcgacaggaa taatgagccc gtgtgtgcgc gcgcgagcgt cgaacatttc ggattaacac  27600
acactcactc acaaaagttt caaagttact taccatcagg ccattgatcg aataccattt  27660
gtgtaacgtc gtgagctgat gtgagtgggt ggaattcgaa ttcatgagtt tttccgctga  27720
caaggatgag acgaagtacc acctaaaagt tggatgtgtt atagataggt ttaggcttag  27780
gttcaggctt tggcttaggc ttattcttaa gcttagggtt aggcttaggc ttaaaaacgg  27840
gaaccgttca gatttatagg ccatgtgaaa aaatgtttaa actaatattt tttcaaatta  27900
actcttaaaa attcaaattt taattttccg ggtaaatttc cttttttatt agtggccgaa  27960
gctgcagttt tctaggcggc cgccaatttt tttaggccat gtagaacacc actagttata  28020
attgttttga aacgcggcca ccgaaatttc taaaatttct aggccatgta ttacgtcaaa  28080
ttttctctag atttttttca aacaaaaaaa actcactcgt tctgcttgag aatcaatcga  28140
ctgttttgca ctcatatccg ggtgcttttc tgattaagaa aaaattcttc tcctgatata  28200
tataatttgt ttcaacgact tcagagtaat tcacgtcgtt tccccacaca cacacggtgt  28260
caccctgaaa aataacaaaa ctatgagcaa atcgatgaga gaaacaggac gtgcgaggac  28320
ggaatgaggg agagaaaagg gactaattat attcatagat gacttggaat ggaattgaaa  28380
caaagtacag agtattctta ttaactggaa agttagatga taaaaaagag aaaacgacgc  28440
aaaaaataac gagggctctt ctgaatgcaa aaatgtaaat gaggttgaga atactgatga  28500
gagagtgatt cttgtccaag ttttgtacgt ggccgagaaa agaagaaaat ctcggccacg  28560
cagataaatg gggtttacag ataaattagt tgaagcttca aaggtgaaag ttttaaggaa  28620
gatagaaaaa atctaagtgg cctagaaaac tctttcacgg ccatcaactt caaatatgtc  28680
tccagccact ccggcagttt ttttttaata tgccgccatt tttatggacc tctatgaaaa  28740
aaaaaatcaa tttctcaaat tttaaaaatc taaaagctgt tggaaaaaaa tgaaaagaaa  28800
aaagaaaatg aaaccaaatg ttagttagtt gagaaacttg aaaaaagaaa cgagaataag  28860
agactgagta aatattgcta agcgacagat ttcgaacaga tgaaatgaga aagggggtct  28920
agtggggtag aagcatagag tatgagagtg aaggagagtg agagagcacg cagagaaaaa  28980
gagattagtt ctacttttca gacgtgcgta cgttcttagt catgcagaat tctgagaata  29040
ttcaaaaata aggaaatgag taataagaca ttagattaag taatagtaga gttcagaaaa  29100
ttgagataaa gctgaaattt taaaaagggt ttaaggccac ctttaaggta aatttccgtt  29160
gtgaagtttt ctaggccacc aacataacca acggctcaaa atgtttcaga acagctcttg  29220
tttttctaga cttttagact tctctttttt aaattgcaca aaaaattggt cttttcgtga  29280
tcatcgagac cacttgaaag tacattgaaa agaacaacgt tgcggcgtca ctgagttatt  29340
tttgaagttt tgttgggcaa cgaggacggg ggaagagaag aaaacataaa atcctaaccc  29400
taacccgacc ccaagcctaa gcccaagtct aagcttaagc ctagcccaaa cctaagccta  29460
```

-continued

```
aacctaacat ttaattaatt ttcaataatg acagctcaaa aaaaagagca aaaaacgggc  29520
ggacctaact tgttcgacta aagggcacgc caagctcaaa gagcattaaa tgcacgttca  29580
gactacttgg acactcaggt caggttacgc gtggaaatac tagaagctct ttttgatgac  29640
gtggcatttt ttttgtctga aaatggagag ggagtggcgg acgagggaga aaaactttgt  29700
atgcataaga aaaactgctg ctgctacttc agcttctagc aaactctaga ataacatgtt  29760
gacgatatat atttttcccc gttttctgaa ttatttgaag aggcaaaaat attataatat  29820
tgaatgaaaa actaggaaat tttagaattt gagttagttg caattgcgct ttaattatat  29880
ttcaagcctt tctgaagcct gtggaagagt gctggggcat aattttcatg gcctaacttt  29940
cctgaagcct cggtcgtcaa aatatcgaaa aaaaaagtta tgggttttta aaacgaaaaa  30000
tattcaaatt ttttcagttt aagaaaatcg aaaacaacaa aaatgtttct aaaaaattct  30060
aaaaatttta ttcttattta ttgattcaaa aattgaaaat tttggatttt tttttctggc  30120
tcactatcag atttcttgat tttccttttt ttttctagaa aatttctatt tttttaaata  30180
aaaaaatgtg gaaatgttat ttcttttgat acataatata catggtacga tacattttaa  30240
atattccaaa tcggccaaat atcatgataa aacactagaa aattttaaag gtttttttggc  30300
aaatttctaa agcctacaac tcctagaata tttaacaaaa aatattttaa acgcaattaa  30360
aatataaaaa tcgtagagaa attttttgtt ggtcgagttc caaaaaataa aaaaaattgg  30420
aaatttggaa gaaaaaaaca ttttttttaat ggttctttaa tcaattaaac tttaattatt  30480
ggtatttaaa tattttgagg aggtggacat gcaaatccta aacaaaagca aaatgcgttg  30540
tcaatttaaa ttttagtttt ttttaaatat gaaaaaaaca caaaaatttc agatctaaaa  30600
tagaagttgt caaaaaattc tcaaaaaaag tgctgaaagt gatggctgac ctcgaaaagg  30660
gaaatgttat gggtataaga gagagagaga gagagtggcc gcaggaaaaa aaacgggttg  30720
gcgccccccg gagaagacga gatgcgggac gaataatttg gttttgacaa cgacggaaaa  30780
tacgaagaag acgaagaaga agacgacgat gtgtatgttc ttcttttgtc gaaatccggc  30840
ccttttggtg gtgtctgcgt ctctctttct ctctatagaa atacactcca agcacacttg  30900
aggtaaataa aattgagaag tggttgtggt ggtggcacat aggtgtttgt atgatgagat  30960
tgagagagag agagtggatt aatataattg attgattgaa aatgtgatcg agagggaaat  31020
tcgatcgaga gggatcgaga gggattgata tggcgaccct agtgatgaat aaggttcagg  31080
aaaactagca taacttttta aaaatgtcat ctaacaattt ttttaatatt tttttctgta  31140
agaaaaacat tgaaaaatac atagttttgg tcacttttca gttgtattgg ctaagaatca  31200
agtaagatat ttcaatttaa attcgaaaat tgcagtaggt caactctccc cgaccagaaa  31260
tggttaggtt tgtggaaagt gacataactt tgtagatgcg tcatctaaaa aattttttaa  31320
tgtattttat aaaagaaaaa catttaacga tattgttggt aagttttcaa ataaattggt  31380
taaaaattga gtgagacatt ctagtttaaa ttcgagtaat atccgctttc cactgcaaaa  31440
gattaactaa ttgaattttc caatattttc taagattatg aaataatttg taaaatatct  31500
taataaccac attttgtaaa tatgaaataa aaaagtttca acaaaaaaat cgataaaaac  31560
ttttttttc gaatttttcg aaaatttaaa ctctaacaat aaactcgggt attttttagc  31620
tttaaaaatt atttttgga atcaaatcta cgaaattatt caaattagcg taaaaattct  31680
gctcaccaat cagcggcgtt gcccacgccc ctgggcaacg ctttaactct ttttactcat  31740
tttggcactt ttttgagaca ttttttgaag attggcttta cgtaaagtaa tttcacatca  31800
acattttttg tattgcctac tgccaaatat tgtaggcacg taggcaggca cacatgccgg  31860
```

-continued

```
caaataggca tgctccaatt aaagatcact cctctccaaa tattatgggt attggtgtct  31920
agagagcaac aacaaaaaat gggaagcata aagcaattca aagattcctc cttttttttct  31980
tttctcgcac gcgatagatg tttggcaaaa gaaatgacgc gtggctttcg atatctgaaa  32040
aaataatatt caaaaaaaaa aaatattttt gttgaaaagc tgatgagaaa aagaagaaaa  32100
ggaaataaaa ggtgataata ggaaaaagag gaacaaatga atgatgtgaa gaccggagaa  32160
ggaggcgggt tatcaggtta ttatcacata caaataagcc atattatcag tcaggaggag  32220
cggtatatgg gaacattgct atttgggaaa aagataatag ggcaattatt caaattatga  32280
ataggggaac aaaaggtttg aaccgaccat tgagatgggg ttggagaaca ttttttcaat  32340
tttagcggaa aattcaaatt ttaattacaa aaacacatac ctacttagag ggaaattcaa  32400
ctttttttaat tttttgaaaa ttaatgacaa aattgcatgg gtttttgttt ttcaaaatat  32460
agtattacgg aactatgaga tcatgagaat acctactctt tgccacatgg cctctcgctg  32520
ccgcggcctg ccaatatttt cgcgccagtg aataggcatt ctcatgatct catggtcccg  32580
taatatgtta ttctgttttt aatatttcaa aaaattttca caggaatttt tttattcaaa  32640
ttttaatttt tttttaattt acaattaggt agaaaactta aattttaaga tcaaagtttt  32700
ggcgggtaac ttgaattttt aaaaaatatt ttgcagaaaa cacaaattaa agcttattaa  32760
tttaaaggga aattcaattt ttaattttca aaaacattcg aaattagttc aattttcaat  32820
ttattttcga attttttaaa aactatcttt ggcgggaagt tcaaatttca attataaaat  32880
tttgccagaa atttttctca ttttttgttt ttaaaaaaat tggcgttaaa aacaagatga  32940
gttaaattca atttttgatt aaaaataatt ttggtgacag gaaatgaaaa tttaatttgt  33000
attattatgg caggaaatta aaattttaaa ttaaagaaat attctgaatt aaattcaatt  33060
ttttaagatt tgttttgaat agctttttgc caaaaaaaat gcaggaaaaa atgcaggaaa  33120
ctcaaactga aagtttttttc aagtaaaatt ttaaaaaatc aaaattttgg aaggagctat  33180
tattttttat tttgacggaa aaatcaaatg tttatatttc aaaaaaaattt ggtgtgaaat  33240
tcaaacttgt tttaaaaaat tccaaaataa tatttttagc agtaaaaatt ttaaagatgg  33300
ataaaagtcg tatgatcata aagtttccta ttataacttt ataaaaaattc tcttccgacg  33360
gaaaatagaa tattcgtaat tctaaagtct atttggatat agtgaatggc tgaattcggg  33420
tggcttcatt gacggtgcac tgaagcgaga aacgacttga tttggttggc attcaacctt  33480
ttcttttctc tttctaatgc aggtcaatca gtgaagacag agagagatag gcgtatagga  33540
aagaagaaag aagaaggagg aaaagggaat tggcaaagaa aaggcataac aataacaaca  33600
gaaagattca acgtcgtcac aaattgaatt gggaacgaac aacaccaaga aacaatcccg  33660
tacacttttt ccagaaatgg aactttttac agaaacattg aaaaaaaaac cacatgattt  33720
caagaaaaac cgcaagtaat ttaaaaagga accaaatttt ttcagctgct caaaaaatca  33780
gctggaaata atcaaaaatt cactttctgg ttcctttttc gcctcccctt tccttctcaa  33840
atgaatcata ttgcaaagta aaagtgagac agaaacattg aattatttat gaaaaaattt  33900
ggtgggtttc atgtgacttt tagattttaa agtaattaaa aattaacatt ttcgtttttta  33960
caattccttg atttagttgg ttttggttta cattaaaaat tgttaactaa taaattacag  34020
attatgtttt ttgctacact ttcgtagttg gacaaagtta aaagggatat attagtattg  34080
caccccgggg gcctcaactt tggaaactta tatctcagtt gttttcaatt atattaaaac  34140
catgttaact acgtgttaat atgtattcta tcgttttcta tatttttgta tttagttgga  34200
```

-continued

```
catttttga tatcgactag aacaatttag ttaaacactg tcgtcaaagt tgatcctaac  34260
ttcaactttt tggaaaaaaa gtctaactgt attttttaaa caatttttc tttccttaca  34320
aaaaagtaat aaaatgaaat tttcagaaaa atatttgaaa ttctcgaaag cagactaaat  34380
tttgcagaac tttacaacaa atttcgcgga aaaaacccag agacctagca ctttctaaca  34440
gtgaaaaaat caattcaaga aaataaaatg cttcttttca aaaagtacac aaaactgtac  34500
gacaccaaat gaggcaagaa tgaaagcatt gctgtccgcc tgcgacaaaa aagtttcaac  34560
gttcttttct gtcttggtca gggaacgggc ttacatcggt tgacaatgcg attgttccga  34620
caaaagagaa aaagaagaag aaaaaacatt gaaatggagg ataagttttg gggtttttgt  34680
tgggaggaat caatttgctt cgaaatctca aagtttcggg aaatttctaa tattttttaa  34740
tgcaaaattt tggctgaaat tcgggggttt gagggttttt tttaatgaaa aaaatagcat  34800
ttgaaaaact gaagttcatg agcttccgga tgacgttaaa a                     34841
```

<210> SEQ ID NO 22
<211> LENGTH: 1748
<212> TYPE: DNA
<213> ORGANISM: Dictyostelium discoideum

<400> SEQUENCE: 22

```
gaattccgga ttttcgatca gaattgggtg tgaaaatcac tggtaaagat tgtccaaaac    60
caattcaatc atgggcacaa gctgggttaa ctgaaaaggt tcatttacta ttaaagaaat   120
ttcaatatga aaaaccaaca tcaattcaag cacaaactat acctgcaatt atgaatggtc   180
gtgatttaat tggtattgcc agaactggtt ccggtaaaac attggcattc cttttaccaa   240
tgtttcgtca tatactggca caaccaaaat ctgcacctgg tgaaggtatg attgcattga   300
ttatgtcacc aactagagaa ttggcacttc aaattcatgt tgaatgtaaa aagttttcaa   360
aagtacttgg attacgtacc gcttgtgttt atggtggtgc aagtataagt gaacaaatag   420
ccgaattgaa aagaggtgcc gatattgtcg tttgcacacc aggtcgtatg atcgatattt   480
tatgtgcaaa taatcgacgt atcaccaacc taagacgtgt aacattcttg gtgttggatg   540
aagccgatcg tatgtttgat atgggttttg gtccacaaat taattgtatc gtcgatagta   600
ttagacccga tcgtcaaacc attatgttct ctgcaacttt tcctccaaaa gttgagaatg   660
tcgcaaagaa gatcctaaac aaaccattgg aaatcattgc tggtggtaga agtatagttt   720
catcagatat tgaacaattt gtagaggtac gtccaactga aactagattt agacgtttaa   780
tagaattgct atcgatttgg tatcataaag gtcagatttt aatctttacc aatcgtcaag   840
agaccaccga caatctatat cgtcaacttt caaactctca atatcaatgt ctatcattac   900
atggtagtaa agatcaaacc gatcgtgatg aaaccattag tgactttaaa aataaggtta   960
aaaccatttt aatcgctaca ccattggcat cacgtggttt ggatatcaaa gatttaaatc  1020
ttgtggttaa tttcgattgc cctgatcatt tggaagatta tgttcatagg gtaggtagaa  1080
ctggtagagc aggaaatcgt ggtactgctt atacatttat cacacccgac gaagagagat  1140
tctcttcgtc aatcattaaa gctttggaac aatctggttc aaaagtaccc gatgaactta  1200
gaaaattgaa tgatacctac gagaaaaaga gaaaagaagg taaggatgta ctattggcac  1260
caaccggttt cactggtaga ggtcataaat ttgatgctgc cgaagaggat aaaaagaata  1320
ttgaaagaaa acaacaaaga aaagcatatg gtatcgaaga ggaagaagaa gaagaggatg  1380
aagataaaga aaaagctgaa aaggagaaat tggccgctgc ttccgctgaa aaagaaaaac  1440
aattattatc tgaaaaagaa aaattggatc ctgctaccac taatactatc gtcatacctg  1500
```

```
gtgtagatgg tacaatcatt acaccttctt cattacttca aaccgatcct tcagttcctg   1560

tgggtcaaca ggctatcaat caaatatttg gtatttcaca agttacctcc tccgaagaag   1620

caattaaaaa acttcaattg gccgctcaat taggtatgaa aggtaatatt caaaaattaa   1680

ataatcaaat aactccatta aatcaaactc atttcattga agaattagaa attaatgatt   1740

cggaattc                                                            1748


<210> SEQ ID NO 23
<211> LENGTH: 661
<212> TYPE: PRT
<213> ORGANISM: Drosophila melanogaster

<400> SEQUENCE: 23

Met Ser Asp Asp Trp Asp Asp Glu Pro Ile Val Asp Thr Arg Gly Ala
1               5                   10                  15

Arg Gly Gly Asp Trp Ser Asp Asp Glu Asp Thr Ala Lys Ser Phe Ser
            20                  25                  30

Gly Glu Ala Glu Gly Asp Gly Val Gly Gly Ser Gly Gly Glu Gly Gly
        35                  40                  45

Gly Tyr Gln Gly Gly Asn Arg Asp Val Phe Gly Arg Ile Gly Gly Gly
    50                  55                  60

Arg Gly Gly Gly Ala Gly Gly Tyr Arg Gly Gly Asn Arg Asp Gly Gly
65                  70                  75                  80

Gly Phe His Gly Gly Arg Arg Glu Gly Glu Arg Asp Phe Arg Gly Gly
                85                  90                  95

Glu Gly Gly Phe Arg Gly Gly Gln Gly Gly Ser Arg Gly Gly Gln Gly
            100                 105                 110

Gly Ser Arg Gly Gly Gln Gly Gly Phe Arg Gly Gly Glu Gly Gly Phe
        115                 120                 125

Arg Gly Arg Leu Tyr Glu Asn Glu Asp Gly Asp Glu Arg Arg Gly Arg
    130                 135                 140

Leu Asp Arg Glu Glu Arg Gly Gly Glu Arg Arg Gly Arg Leu Asp Arg
145                 150                 155                 160

Glu Glu Arg Gly Gly Glu Arg Gly Glu Arg Gly Asp Gly Gly Phe Ala
                165                 170                 175

Arg Arg Arg Arg Asn Glu Asp Asp Ile Asn Asn Asn Asn Asn Ile Ala
            180                 185                 190

Glu Asp Val Glu Arg Lys Arg Glu Phe Tyr Ile Pro Pro Glu Pro Ser
        195                 200                 205

Asn Asp Ala Ile Glu Ile Phe Ser Ser Gly Ile Ala Ser Gly Ile His
    210                 215                 220

Phe Ser Lys Tyr Asn Asn Ile Pro Val Lys Val Thr Gly Ser Asp Val
225                 230                 235                 240

Pro Gln Pro Ile Gln His Phe Thr Ser Ala Asp Leu Arg Asp Ile Ile
                245                 250                 255

Ile Asp Asn Val Asn Lys Ser Gly Phe Lys Ile Pro Thr Pro Ile Gln
            260                 265                 270

Lys Cys Ser Ile Pro Val Ile Ser Ser Gly Arg Asp Leu Met Ala Cys
        275                 280                 285

Ala Gln Thr Gly Ser Gly Lys Thr Ala Ala Phe Leu Leu Pro Ile Leu
    290                 295                 300

Ser Lys Leu Leu Glu Asp Pro His Glu Leu Glu Leu Gly Arg Pro Gln
305                 310                 315                 320
```

```
Val Val Ile Val Ser Pro Thr Arg Glu Leu Ala Ile Gln Ile Phe Asn
                325                 330                 335

Glu Ala Arg Lys Phe Ala Phe Glu Ser Tyr Leu Lys Ile Gly Ile Val
            340                 345                 350

Tyr Gly Gly Thr Ser Phe Arg His Gln Asn Glu Cys Ile Thr Arg Gly
        355                 360                 365

Cys His Val Val Ile Ala Thr Pro Gly Arg Leu Leu Asp Phe Val Asp
    370                 375                 380

Arg Thr Phe Ile Thr Phe Glu Asp Thr Arg Phe Val Val Leu Asp Glu
385                 390                 395                 400

Ala Asp Arg Met Leu Asp Met Gly Phe Ser Glu Asp Met Arg Arg Ile
                405                 410                 415

Met Thr His Val Thr Met Arg Pro Glu His Gln Thr Leu Met Phe Ser
            420                 425                 430

Ala Thr Phe Pro Glu Glu Ile Gln Arg Met Ala Gly Glu Phe Leu Lys
        435                 440                 445

Asn Tyr Val Ser Val Ala Ile Gly Ile Val Gly Gly Ala Cys Ser Asp
    450                 455                 460

Val Lys Gln Thr Ile Tyr Glu Val Asn Lys Tyr Ala Lys Arg Ser Lys
465                 470                 475                 480

Leu Ile Glu Ile Leu Ser Glu Gln Ala Asp Gly Thr Ile Val Phe Val
                485                 490                 495

Glu Thr Lys Arg Gly Ala Asp Phe Leu Ala Ser Phe Leu Ser Glu Lys
            500                 505                 510

Glu Phe Pro Thr Thr Ser Ile His Gly Asp Arg Leu Gln Ser Gln Arg
        515                 520                 525

Glu Gln Ala Leu Arg Asp Phe Lys Asn Gly Ser Met Lys Val Leu Ile
    530                 535                 540

Ala Thr Ser Val Ala Ser Arg Gly Leu Asp Ile Lys Asn Ile Lys His
545                 550                 555                 560

Val Ile Asn Tyr Asp Met Pro Ser Lys Ile Asp Asp Tyr Val His Arg
                565                 570                 575

Ile Gly Arg Thr Gly Cys Val Gly Asn Asn Gly Arg Ala Thr Ser Phe
            580                 585                 590

Phe Asp Pro Glu Lys Asp Arg Ala Ile Ala Ala Asp Leu Val Lys Ile
        595                 600                 605

Leu Glu Gly Ser Gly Gln Thr Val Pro Asp Phe Leu Arg Thr Cys Gly
    610                 615                 620

Ala Gly Gly Asp Gly Gly Tyr Ser Asn Gln Asn Phe Gly Gly Val Asp
625                 630                 635                 640

Val Arg Gly Arg Gly Asn Tyr Val Gly Asp Ala Thr Asn Val Glu Glu
                645                 650                 655

Glu Glu Gln Trp Asp
            660


<210> SEQ ID NO 24
<211> LENGTH: 713
<212> TYPE: PRT
<213> ORGANISM: Rattus norvegicus

<400> SEQUENCE: 24

Met Gly Asp Glu Asp Trp Glu Ala Glu Ile Leu Lys Pro His Val Ser
1               5                   10                  15

Ser Tyr Val Pro Val Phe Glu Lys Asp Lys Tyr Ser Ser Gly Ala Asn
            20                  25                  30
```

-continued

```
Gly Asp Thr Phe Asn Arg Thr Ser Ala Ser Ser Ser Glu Met Glu Asp
        35                  40                  45

Gly Pro Ser Gly Arg Asp His Phe Met Arg Ser Gly Phe Ser Ser Gly
    50                  55                  60

Arg Asn Leu Gly Asn Arg Asp Ile Gly Glu Ser Ser Lys Arg Glu Thr
65                  70                  75                  80

Thr Ser Thr Thr Gly Gly Phe Gly Arg Gly Lys Gly Phe Gly Asn Arg
                85                  90                  95

Gly Phe Leu Asn Asn Lys Phe Glu Glu Gly Asp Ser Ser Gly Phe Trp
            100                 105                 110

Lys Glu Ser Thr Asn Asp Cys Glu Asp Thr Gln Thr Arg Ser Arg Gly
        115                 120                 125

Phe Ser Lys Arg Gly Gly Tyr Pro Asp Gly Asn Asp Ser Glu Ala Ser
    130                 135                 140

Gly Pro Phe Arg Arg Gly Gly Arg Asp Ser Glu Tyr Asp Gln Asp Gln
145                 150                 155                 160

Gly Ser Gln Arg Gly Gly Gly Leu Phe Gly Ser Arg Lys Pro Ala Ala
                165                 170                 175

Ser Asp Ser Gly Ser Gly Asp Thr Phe Gln Ser Arg Ser Gly Asn Ala
            180                 185                 190

Arg Gly Ala Tyr Lys Gly Leu Asn Glu Glu Val Val Thr Gly Ser Gly
        195                 200                 205

Lys Asn Ser Trp Lys Ser Glu Ala Glu Gly Gly Glu Ser Ser Asp Ile
    210                 215                 220

Gln Gly Pro Lys Val Thr Tyr Ile Pro Pro Pro Pro Pro Glu Asp Glu
225                 230                 235                 240

Asp Ser Ile Phe Ala His Tyr Gln Thr Gly Ile Asn Phe Asp Lys Tyr
                245                 250                 255

Asp Thr Ile Leu Val Glu Val Ser Gly His Asp Ala Pro Pro Ala Ile
            260                 265                 270

Leu Thr Phe Glu Glu Ala Asn Leu Cys Gln Thr Leu Asn Asn Asn Ile
        275                 280                 285

Ala Lys Ala Gly Tyr Thr Lys Leu Thr Pro Val Gln Lys Tyr Ser Ile
    290                 295                 300

Pro Ile Val Leu Ala Gly Arg Asp Leu Met Ala Cys Ala Gln Thr Gly
305                 310                 315                 320

Ser Gly Lys Thr Ala Ala Phe Leu Leu Pro Ile Leu Ala His Met Met
                325                 330                 335

Arg Asp Gly Ile Thr Ala Ser Arg Phe Lys Glu Leu Gln Glu Pro Glu
            340                 345                 350

Cys Ile Ile Val Ala Pro Thr Arg Glu Leu Ile Asn Gln Ile Tyr Leu
        355                 360                 365

Glu Ala Arg Lys Phe Ser Phe Gly Thr Cys Val Arg Ala Val Val Ile
    370                 375                 380

Tyr Gly Gly Thr Gln Phe Gly His Ser Ile Arg Gln Ile Val Gln Gly
385                 390                 395                 400

Cys Asn Ile Leu Cys Ala Thr Pro Gly Arg Leu Met Asp Ile Ile Gly
                405                 410                 415

Lys Glu Lys Ile Gly Leu Lys Gln Val Lys Tyr Leu Val Leu Asp Glu
            420                 425                 430

Ala Asp Arg Met Leu Asp Met Gly Phe Gly Pro Glu Met Lys Lys Leu
        435                 440                 445
```

-continued

```
Ile Ser Cys Pro Gly Met Pro Ser Lys Glu Gln Arg Gln Thr Leu Leu
    450                 455                 460

Phe Ser Ala Thr Phe Pro Glu Glu Ile Gln Arg Leu Ala Gly Glu Phe
465                 470                 475                 480

Leu Lys Ser Asn Tyr Leu Phe Val Ala Val Gly Gln Val Gly Gly Ala
                485                 490                 495

Cys Arg Asp Val Gln Gln Ser Ile Leu Gln Val Gly Pro Val Phe Lys
            500                 505                 510

Lys Arg Lys Leu Val Glu Ile Leu Arg Asn Ile Gly Asp Glu Arg Pro
        515                 520                 525

Met Val Phe Val Glu Thr Lys Lys Lys Ala Asp Phe Ile Ala Thr Phe
    530                 535                 540

Leu Cys Gln Glu Lys Ile Ser Thr Thr Ser Ile His Gly Asp Arg Glu
545                 550                 555                 560

Gln Arg Glu Arg Glu Gln Ala Leu Gly Asp Phe Arg Cys Gly Lys Cys
                565                 570                 575

Pro Val Leu Val Ala Thr Ser Val Ala Ala Arg Gly Leu Asp Ile Glu
            580                 585                 590

Asn Val Gln His Val Ile Asn Phe Asn Leu Pro Ser Thr Ile Asp Glu
        595                 600                 605

Tyr Val His Arg Ile Gly Arg Thr Gly Arg Cys Gly Asn Thr Gly Arg
    610                 615                 620

Ala Ile Ser Phe Phe Asp Thr Glu Ser Asp Asn His Leu Ala Gln Pro
625                 630                 635                 640

Leu Val Lys Val Leu Ser Asp Ala Gln Gln Asp Val Pro Ala Trp Leu
                645                 650                 655

Glu Glu Ile Ala Phe Ser Ser Tyr Ala Pro Pro Ser Phe Ser Asn Ser
            660                 665                 670

Thr Arg Gly Ala Val Phe Ala Ser Phe Asp Thr Arg Lys Asn Phe Gln
        675                 680                 685

Gly Lys Asn Thr Leu Asn Thr Ala Gly Ile Ser Ser Ala Gln Ala Pro
    690                 695                 700

Asn Pro Val Asp Asp Glu Ser Trp Asp
705                 710


<210> SEQ ID NO 25
<211> LENGTH: 637
<212> TYPE: PRT
<213> ORGANISM: Mus musculus

<400> SEQUENCE: 25

Phe Gly Arg Gly Lys Gly Phe Gly Asn Arg Gly Phe Leu Asn Asn Lys
1               5                   10                  15

Phe Glu Glu Gly Asp Ser Ser Gly Phe Trp Lys Glu Ser Asn Asn Asp
            20                  25                  30

Cys Glu Asp Asn Gln Thr Arg Ser Arg Gly Phe Ser Lys Arg Gly Gly
        35                  40                  45

Cys Gln Asp Gly Asn Asp Ser Glu Ala Ser Gly Pro Phe Arg Arg Gly
    50                  55                  60

Gly Arg Gly Ser Phe Arg Gly Cys Arg Gly Gly Phe Gly Leu Gly Arg
65                  70                  75                  80

Pro Asn Ser Glu Ser Asp Gln Asp Gln Gly Thr Gln Cys Gly Gly Gly
                85                  90                  95

Phe Leu Val Leu Gly Lys Pro Ala Ala Ser Asp Ser Gly Asn Gly Asp
            100                 105                 110
```

```
Thr Tyr Gln Ser Arg Ser Gly Ser Gly Arg Gly Gly Tyr Lys Gly Leu
        115                 120                 125

Asn Glu Glu Val Val Thr Gly Ser Gly Lys Asn Ser Trp Lys Ser Glu
    130                 135                 140

Thr Glu Gly Gly Glu Ser Ser Asp Ser Gln Gly Pro Lys Val Thr Tyr
145                 150                 155                 160

Ile Pro Pro Pro Pro Pro Glu Asp Glu Asp Ser Ile Phe Ala His Tyr
                165                 170                 175

Gln Thr Gly Ile Asn Phe Asp Lys Tyr Asp Thr Ile Leu Val Glu Val
            180                 185                 190

Ser Gly His Asp Ala Pro Pro Ala Ile Leu Thr Phe Glu Glu Ala Asn
        195                 200                 205

Leu Cys Gln Thr Leu Asn Asn Asn Ile Arg Lys Ala Gly Tyr Thr Lys
    210                 215                 220

Leu Thr Pro Val Gln Lys Tyr Thr Ile Pro Ile Val Leu Ala Gly Arg
225                 230                 235                 240

Asp Leu Met Ala Cys Ala Gln Thr Gly Ser Gly Lys Thr Ala Ala Phe
                245                 250                 255

Leu Leu Pro Ile Leu Ala His Met Met Arg Asp Gly Ile Thr Ala Ser
            260                 265                 270

Arg Phe Lys Glu Leu Gln Glu Pro Glu Cys Ile Ile Val Ala Pro Thr
        275                 280                 285

Arg Glu Leu Ile Asn Gln Ile Tyr Leu Glu Ala Arg Lys Phe Ser Phe
    290                 295                 300

Gly Thr Cys Val Ile Ser Val Val Ile Tyr Gly Gly Thr Gln Phe Gly
305                 310                 315                 320

His Ser Val Arg Gln Ile Val Gln Gly Cys Asn Ile Leu Cys Ala Thr
                325                 330                 335

Pro Gly Arg Leu Met Asp Ile Ile Gly Lys Glu Lys Ile Gly Leu Lys
            340                 345                 350

Gln Val Lys Tyr Leu Val Leu Asp Glu Ala Asp Ser Met Leu Asp Met
        355                 360                 365

Gly Phe Ala Pro Glu Ile Lys Lys Leu Ile Ser Cys Pro Gly Met Pro
    370                 375                 380

Ser Lys Glu Gln His Gln Thr Leu Leu Phe Ser Ala Thr Phe Pro Glu
385                 390                 395                 400

Glu Ile Gln Arg Leu Ala Gly Asp Phe Leu Lys Ser Asn Tyr Leu Phe
                405                 410                 415

Val Ala Val Gly Gln Val Gly Gly Ala Cys Arg Asp Val Gln Gln Thr
            420                 425                 430

Ile Leu Gln Val Gly Gln Tyr Gln Lys Glu Lys Ser Leu Leu Arg Phe
        435                 440                 445

Tyr Glu Asn Ile Gly Asp Glu Arg Thr Met Val Phe Val Glu Thr Lys
    450                 455                 460

Lys Lys Ala Asp Phe Ile Ala Thr Phe Leu Cys Gln Glu Lys Ile Ser
465                 470                 475                 480

Ser Thr Ser Ile His Gly Asp Arg Glu Gln Arg Glu Arg Glu Gln Ala
                485                 490                 495

Leu Gly Asp Phe Arg Cys Gly Lys Cys Pro Val Leu Val Ala Thr Ser
            500                 505                 510

Val Ala Ala Arg Gly Leu Asp Ile Glu Asn Val Gln His Val Ile Asn
        515                 520                 525
```

-continued

```
Phe Asp Leu Pro Ser Thr Ile Asp Glu Tyr Val His Arg Ile Gly Arg
    530                 535                 540

Thr Gly Arg Cys Gly Asn Thr Gly Arg Ala Ile Ser Phe Phe Asp Thr
545                 550                 555                 560

Asp Ser Asp Asn His Leu Ala Gln Pro Leu Val Lys Val Leu Ser Asp
                565                 570                 575

Ala Gln Gln Asp Val Pro Ala Trp Leu Glu Glu Ile Ala Phe Ser Thr
            580                 585                 590

Tyr Val Pro Pro Ser Phe Ser Ser Ser Thr Arg Gly Gly Ala Val Phe
        595                 600                 605

Ala Ser Val Asp Thr Arg Lys Asn Tyr Gln Gly Lys Ala His Val Glu
    610                 615                 620

Tyr Ser Gly Asp Phe Phe Phe Thr Ser Ser Gln Ser Ser
625                 630                 635


<210> SEQ ID NO 26
<211> LENGTH: 662
<212> TYPE: PRT
<213> ORGANISM: Mus musculus

<400> SEQUENCE: 26

Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
    50                  55                  60

Asp Lys Asp Ala Tyr Ser Ser Phe Gly Ser Arg Gly Asp Ser Arg Gly
65                  70                  75                  80

Lys Ser Ser Phe Phe Gly Asp Arg Gly Ser Gly Ser Arg Gly Arg Phe
                85                  90                  95

Asp Asp Arg Gly Arg Gly Asp Tyr Asp Gly Ile Gly Gly Arg Gly Asp
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
    130                 135                 140

Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
        195                 200                 205

His Ala Ile Pro Ile Ile Lys Glu Lys Arg Asp Leu Met Ala Cys Ala
    210                 215                 220

Gln Thr Gly Ser Gly Lys Thr Ala Ala Phe Leu Leu Pro Ile Leu Ser
225                 230                 235                 240

Gln Ile Tyr Ala Asp Gly Pro Gly Glu Ala Leu Arg Ala Met Lys Glu
                245                 250                 255

Asn Gly Arg Tyr Gly Arg Arg Lys Gln Tyr Pro Ile Ser Leu Val Leu
            260                 265                 270
```

-continued

```
Ala Pro Thr Arg Glu Leu Ala Val Gln Ile Tyr Glu Glu Ala Arg Lys
        275                 280                 285

Phe Ser Tyr Arg Ser Arg Val Arg Pro Cys Val Val Tyr Gly Gly Ala
    290                 295                 300

Glu Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
            340                 345                 350

Leu Asp Met Gly Phe Glu Pro Gln Ile Arg Arg Ile Val Glu Gln Asp
        355                 360                 365

Thr Met Pro Pro Lys Gly Val Arg His Thr Met Met Phe Ser Ala Thr
    370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

Gln Lys Val Val Trp Val Glu Glu Ile Asp Lys Arg Ser Phe Leu Leu
            420                 425                 430

Asp Leu Leu Asn Ala Thr Gly Lys Asp Ser Leu Thr Leu Val Phe Val
        435                 440                 445

Glu Thr Lys Lys Gly Ala Asp Ser Leu Glu Asp Phe Leu Tyr His Glu
    450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
        515                 520                 525

Ile Gly Arg Thr Gly Arg Val Gly Asn Leu Gly Leu Ala Thr Ser Phe
    530                 535                 540

Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Phe
                565                 570                 575

Glu His His Tyr Lys Gly Ser Ser Arg Gly Arg Ser Lys Ser Ser Arg
            580                 585                 590

Phe Ser Gly Gly Phe Gly Ala Arg Asp Tyr Arg Gln Ser Ser Gly Ala
        595                 600                 605

Ser Ser Ser Ser Phe Ser Ser Ser Arg Ala Ser Ser Ser Arg Ser Gly
    610                 615                 620

Gly Gly Gly His Gly Gly Ser Arg Gly Phe Gly Gly Gly Gly Tyr Gly
625                 630                 635                 640

Gly Phe Tyr Asn Ser Asp Gly Tyr Gly Gly Asn Tyr Asn Ser Gln Gly
                645                 650                 655

Val Asp Trp Trp Gly Asn
            660
```

<210> SEQ ID NO 27
<211> LENGTH: 662

<212> TYPE: PRT
<213> ORGANISM: Homo sapiens

<400> SEQUENCE: 27

```
Met Ser His Val Ala Val Glu Asn Ala Leu Gly Leu Asp Gln Gln Phe
1               5                   10                  15

Ala Gly Leu Asp Leu Asn Ser Ser Asp Asn Gln Ser Gly Gly Ser Thr
            20                  25                  30

Ala Ser Lys Gly Arg Tyr Ile Pro Pro His Leu Arg Asn Arg Glu Ala
        35                  40                  45

Thr Lys Gly Phe Tyr Asp Lys Asp Ser Ser Gly Trp Ser Ser Ser Lys
    50                  55                  60

Asp Lys Asp Ala Tyr Ser Ser Phe Gly Ser Arg Ser Asp Ser Arg Gly
65                  70                  75                  80

Lys Ser Ser Phe Phe Ser Asp Arg Gly Ser Gly Ser Arg Gly Arg Phe
                85                  90                  95

Asp Asp Arg Gly Arg Ser Asp Tyr Asp Gly Ile Gly Ser Arg Gly Asp
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
    130                 135                 140

Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
        195                 200                 205

His Ala Ile Pro Ile Ile Lys Glu Lys Arg Asp Leu Met Ala Cys Ala
    210                 215                 220

Gln Thr Gly Ser Gly Lys Thr Ala Ala Phe Leu Leu Pro Ile Leu Ser
225                 230                 235                 240

Gln Ile Tyr Ser Asp Gly Pro Gly Glu Ala Leu Arg Ala Met Lys Glu
                245                 250                 255

Asn Gly Arg Tyr Gly Arg Arg Lys Gln Tyr Pro Ile Ser Leu Val Leu
            260                 265                 270

Ala Pro Thr Arg Glu Leu Ala Val Gln Ile Tyr Glu Glu Ala Arg Lys
        275                 280                 285

Phe Ser Tyr Arg Ser Arg Val Arg Pro Cys Val Val Tyr Gly Gly Ala
    290                 295                 300

Asp Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
                325                 330                 335

Gly Leu Asp Phe Cys Lys Tyr Leu Val Leu Asp Glu Ala Asp Arg Met
            340                 345                 350

Leu Asp Met Gly Phe Glu Pro Gln Ile Arg Arg Ile Val Glu Gln Asp
        355                 360                 365

Thr Met Pro Pro Lys Gly Val Arg His Thr Met Met Phe Ser Ala Thr
    370                 375                 380

Phe Pro Lys Glu Ile Gln Met Leu Ala Arg Asp Phe Leu Asp Glu Tyr
385                 390                 395                 400
```

```
Ile Phe Leu Ala Val Gly Arg Val Gly Ser Thr Ser Glu Asn Ile Thr
                405                 410                 415

Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
        435                 440                 445

Glu Thr Lys Lys Gly Ala Asp Ser Leu Glu Asp Phe Leu Tyr His Glu
    450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
        515                 520                 525

Ile Gly Arg Thr Gly Arg Val Gly Asn Leu Gly Leu Ala Thr Ser Phe
    530                 535                 540

Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Tyr
                565                 570                 575

Glu His His Tyr Lys Gly Ser Ser Arg Gly Arg Ser Lys Ser Ser Arg
            580                 585                 590

Phe Ser Gly Gly Phe Gly Ala Arg Asp Tyr Arg Gln Ser Ser Gly Ala
        595                 600                 605

Ser Ser Ser Ser Phe Ser Ser Ser Arg Ala Ser Ser Ser Arg Ser Gly
    610                 615                 620

Gly Gly Gly His Gly Ser Ser Arg Gly Phe Gly Gly Gly Gly Tyr Gly
625                 630                 635                 640

Gly Phe Tyr Asn Ser Asp Gly Tyr Gly Gly Asn Tyr Asn Ser Gln Gly
                645                 650                 655

Val Asp Trp Trp Gly Asn
            660


<210> SEQ ID NO 28
<211> LENGTH: 697
<212> TYPE: PRT
<213> ORGANISM: Xenopus laevis

<400> SEQUENCE: 28

Met Ser His Val Ala Val Glu Asn Val Leu Asn Leu Asp Gln Gln Phe
1               5                   10                  15

Ala Gly Leu Asp Leu Asn Ser Ala Asp Ala Glu Ser Gly Val Ala Gly
            20                  25                  30

Thr Lys Gly Arg Tyr Ile Pro Pro His Leu Arg Asn Lys Glu Ala Ser
        35                  40                  45

Arg Asn Asp Ser Asn Trp Asp Ser Gly Arg Gly Gly Asn Gly Tyr Ile
    50                  55                  60

Asn Gly Met Gln Asp Asp Arg Asp Gly Arg Met Asn Gly Tyr Asp Arg
65                  70                  75                  80

Gly Gly Tyr Gly Ser Arg Gly Thr Gly Arg Ser Asp Arg Gly Phe Tyr
                85                  90                  95

Asp Arg Glu Asn Ser Gly Trp Asn Ser Gly Arg Asp Lys Asp Ala Tyr
```

-continued

```
            100                 105                 110

Ser Ser Phe Gly Ser Arg Gly Asp Arg Gly Lys Gly Ser Leu Phe Asn
        115                 120                 125

Glu Arg Gly Ser Gly Ser Arg Arg Thr Asp Asp Arg Arg Gln Asp Gly
    130                 135                 140

Phe Asp Gly Met Gly Asn Arg Ser Asp Lys Ser Gly Phe Gly Arg Phe
145                 150                 155                 160

Asp Arg Gly Asn Ser Arg Trp Ser Asp Asp Arg Asn Asp Glu Asp Asp
                165                 170                 175

Trp Ser Lys Pro Leu Ala Pro Asn Asp Arg Val Glu Gln Glu Leu Phe
            180                 185                 190

Ser Gly Ser Asn Thr Gly Ile Asn Phe Glu Lys Tyr Asp Asp Ile Pro
        195                 200                 205

Val Glu Ala Thr Gly Ser Asn Cys Pro Pro His Ile Glu Ser Phe His
    210                 215                 220

Asp Val Thr Met Gly Glu Ile Ile Met Gly Asn Ile Gln Leu Thr Arg
225                 230                 235                 240

Tyr Thr Arg Pro Thr Pro Val Gln Lys His Ala Ile Pro Ile Ile Ile
                245                 250                 255

Glu Lys Arg Asp Leu Met Ala Cys Ala Gln Thr Gly Ser Gly Lys Thr
            260                 265                 270

Ala Ala Phe Leu Leu Pro Ile Leu Ser Gln Ile Tyr Ala Asp Gly Pro
        275                 280                 285

Gly Asp Ala Met Lys His Leu Gln Glu Asn Gly Arg Tyr Gly Arg Arg
    290                 295                 300

Lys Gln Phe Pro Leu Ser Leu Val Leu Ala Pro Thr Arg Glu Leu Ala
305                 310                 315                 320

Val Gln Ile Tyr Glu Glu Ala Arg Lys Phe Ala Tyr Arg Ser Arg Val
                325                 330                 335

Arg Pro Cys Val Val Tyr Gly Gly Ala Asp Ile Gly Gln Gln Ile Arg
            340                 345                 350

Asp Leu Glu Arg Gly Cys His Leu Leu Val Ala Thr Pro Gly Arg Leu
        355                 360                 365

Val Asp Met Met Glu Arg Gly Lys Ile Gly Leu Asp Phe Cys Lys Tyr
    370                 375                 380

Leu Val Leu Asp Glu Ala Asp Arg Met Leu Asp Met Gly Phe Glu Pro
385                 390                 395                 400

Gln Ile Arg Arg Ile Val Glu Gln Asp Thr Met Pro Pro Lys Gly Val
                405                 410                 415

Arg Gln Thr Met Met Phe Ser Ala Thr Phe Pro Lys Glu Ile Gln Ile
            420                 425                 430

Leu Ala Arg Asp Phe Leu Asp Glu Tyr Ile Phe Leu Ala Val Gly Arg
        435                 440                 445

Val Gly Ser Thr Ser Glu Asn Ile Thr Gln Lys Val Val Trp Val Glu
    450                 455                 460

Glu Met Asp Lys Arg Ser Phe Leu Leu Asp Leu Leu Asn Ala Thr Gly
465                 470                 475                 480

Lys Asp Ser Leu Thr Leu Val Phe Val Glu Thr Lys Lys Gly Ala Asp
                485                 490                 495

Ala Leu Glu Asp Phe Leu Tyr His Glu Gly Tyr Ala Cys Thr Ser Ile
            500                 505                 510

His Gly Asp Arg Ser Gln Arg Asp Arg Glu Glu Ala Leu His Gln Phe
        515                 520                 525
```

```
Arg Ser Gly Lys Ser Pro Ile Leu Val Ala Thr Ala Val Ala Ala Arg
    530                 535                 540

Gly Leu Asp Ile Ser Asn Val Lys His Val Ile Asn Phe Asp Leu Pro
545                 550                 555                 560

Ser Asp Ile Glu Glu Tyr Val His Arg Ile Gly Arg Thr Gly Arg Val
                565                 570                 575

Gly Asn Leu Gly Leu Ala Thr Ser Phe Phe Asn Glu Lys Asn Ile Asn
            580                 585                 590

Ile Thr Lys Asp Leu Leu Asp Leu Leu Val Glu Ala Lys Gln Glu Val
        595                 600                 605

Pro Ser Trp Leu Glu Asn Met Ala Tyr Glu Gln His His Lys Ser Ser
    610                 615                 620

Ser Arg Gly Arg Ser Lys Ser Arg Phe Ser Gly Gly Phe Gly Ala Lys
625                 630                 635                 640

Asp Tyr Arg Gln Ser Ser Gly Ala Gly Ser Ser Phe Gly Ser Ser Arg
                645                 650                 655

Gly Gly Arg Ser Ser Gly His Gly Gly Ser Arg Gly Phe Gly Gly Gly
            660                 665                 670

Tyr Gly Gly Phe Tyr Asn Ser Asp Gly Tyr Gly Gly Asn Tyr Gly Gly
        675                 680                 685

Ser Ser Gln Val Asp Trp Trp Gly Asn
    690                 695


<210> SEQ ID NO 29
<211> LENGTH: 660
<212> TYPE: PRT
<213> ORGANISM: Mus musculus

<400> SEQUENCE: 29

Met Ser His Val Ala Glu Glu Asp Glu Leu Gly Leu Asp Gln Gln Leu
1               5                   10                  15

Ala Gly Leu Asp Leu Thr Ser Arg Asp Ser Gln Ser Gly Gly Ser Thr
            20                  25                  30

Ala Ser Lys Gly Arg Tyr Ile Pro Pro His Leu Arg Asn Arg Glu Ala
        35                  40                  45

Ala Lys Ala Phe Tyr Asp Lys Asp Gly Ser Arg Trp Ser Lys Asp Lys
    50                  55                  60

Asp Ala Tyr Ser Ser Phe Gly Ser Arg Ser Asp Thr Arg Ala Lys Ser
65                  70                  75                  80

Ser Phe Phe Ser Asp Arg Gly Gly Ser Gly Ser Arg Gly Arg Phe Asp
                85                  90                  95

Glu Arg Gly Arg Ser Asp Tyr Glu Ser Val Gly Ser Arg Gly Gly Arg
            100                 105                 110

Ser Gly Phe Gly Lys Phe Glu Arg Gly Gly Asn Ser Arg Trp Cys Asp
        115                 120                 125

Lys Ala Asp Glu Asp Asp Trp Ser Lys Pro Leu Pro Pro Ser Glu Arg
    130                 135                 140

Leu Glu Gln Glu Leu Phe Ser Gly Gly Asn Thr Gly Ile Asn Phe Glu
145                 150                 155                 160

Lys Tyr Asp Asp Ile Pro Val Glu Ala Thr Gly Asn Asn Cys Pro Pro
                165                 170                 175

His Ile Glu Ser Phe Ser Asp Val Glu Met Gly Glu Ile Ile Met Gly
            180                 185                 190

Asn Ile Glu Leu Thr Arg Tyr Thr Arg Pro Thr Pro Val Gln Lys His
```

-continued

```
        195                 200                 205

Ala Ile Pro Ile Ile Lys Glu Lys Arg Asp Leu Met Ala Cys Ala Gln
    210                 215                 220

Thr Gly Ser Gly Lys Thr Ala Ala Phe Leu Leu Pro Ile Leu Ser Gln
225                 230                 235                 240

Ile Tyr Thr Asp Gly Pro Gly Glu Ala Leu Arg Ala Met Lys Glu Asn
                245                 250                 255

Gly Lys Tyr Gly Arg Arg Lys Gln Tyr Pro Ile Ser Leu Val Leu Ala
            260                 265                 270

Pro Thr Arg Glu Leu Ala Val Gln Ile Tyr Glu Glu Ala Arg Lys Phe
        275                 280                 285

Ser Tyr Arg Ser Arg Val Arg Pro Cys Val Val Tyr Gly Gly Ala Asp
    290                 295                 300

Ile Gly Gln Gln Ile Arg Asp Leu Glu Arg Gly Cys His Leu Leu Val
305                 310                 315                 320

Ala Thr Pro Gly Arg Leu Val Asp Met Met Glu Arg Gly Lys Ile Gly
                325                 330                 335

Leu Asp Phe Cys Lys Tyr Leu Val Leu Asp Glu Ala Asp Arg Met Leu
            340                 345                 350

Asp Met Gly Phe Glu Pro Gln Ile Arg Arg Ile Val Glu Gln Asp Thr
        355                 360                 365

Met Pro Pro Lys Gly Val Arg His Thr Met Met Phe Ser Ala Thr Phe
    370                 375                 380

Pro Lys Glu Ile Gln Met Leu Ala Arg Asp Phe Leu Asp Glu Tyr Ile
385                 390                 395                 400

Phe Leu Ala Val Gly Arg Val Gly Ser Thr Ser Glu Asn Ile Thr Gln
                405                 410                 415

Lys Val Val Trp Val Glu Glu Ala Asp Lys Arg Ser Phe Leu Leu Asp
            420                 425                 430

Leu Leu Asn Ala Thr Gly Lys Asp Ser Leu Ile Leu Val Phe Val Glu
        435                 440                 445

Thr Lys Lys Gly Ala Asp Ser Leu Glu Asp Phe Leu Tyr His Glu Gly
    450                 455                 460

Tyr Ala Cys Thr Ser Ile His Gly Asp Arg Ser Gln Arg Asp Arg Glu
465                 470                 475                 480

Glu Ala Leu His Gln Phe Arg Ser Gly Lys Ser Pro Ile Leu Val Ala
                485                 490                 495

Thr Ala Val Ala Ala Arg Gly Leu Asp Ile Ser Asn Val Lys His Val
            500                 505                 510

Ile Asn Phe Asp Leu Pro Ser Asp Ile Glu Glu Tyr Val His Arg Ile
        515                 520                 525

Gly Arg Thr Gly Arg Val Gly Asn Leu Gly Leu Ala Thr Ser Phe Phe
    530                 535                 540

Asn Glu Arg Asn Ile Asn Ile Thr Lys Asp Leu Leu Asp Leu Leu Val
545                 550                 555                 560

Glu Ala Lys Gln Glu Val Pro Ser Trp Leu Glu Asn Met Ala Phe Glu
                565                 570                 575

His His Tyr Lys Gly Gly Ser Arg Gly Arg Ser Lys Ser Arg Phe Ser
            580                 585                 590

Gly Gly Phe Gly Ala Arg Asp Tyr Arg Gln Ser Ser Gly Ala Ser Ser
        595                 600                 605

Ser Ser Phe Ser Ser Gly Arg Ala Ser Asn Ser Arg Ser Gly Gly Gly
    610                 615                 620
```

```
Ser His Gly Ser Ser Arg Gly Phe Gly Gly Gly Ser Tyr Gly Gly Phe
625                 630                 635                 640

Tyr Asn Ser Asp Gly Tyr Gly Gly Asn Tyr Ser Ser Gln Gly Val Asp
                645                 650                 655

Trp Trp Gly Asn
            660


<210> SEQ ID NO 30
<211> LENGTH: 660
<212> TYPE: PRT
<213> ORGANISM: Homo sapiens

<400> SEQUENCE: 30

Met Ser His Val Val Val Lys Asn Asp Pro Glu Leu Asp Gln Gln Leu
1               5                   10                  15

Ala Asn Leu Asp Leu Asn Ser Glu Lys Gln Ser Gly Gly Ala Ser Thr
            20                  25                  30

Ala Ser Lys Gly Arg Tyr Ile Pro Pro His Leu Arg Asn Lys Glu Ala
        35                  40                  45

Ser Lys Gly Phe His Asp Lys Asp Ser Ser Gly Trp Ser Cys Ser Lys
    50                  55                  60

Asp Lys Asp Ala Tyr Ser Ser Phe Gly Ser Arg Asp Ser Arg Gly Lys
65                  70                  75                  80

Pro Gly Tyr Phe Ser Glu Arg Gly Ser Gly Ser Arg Gly Arg Phe Asp
                85                  90                  95

Asp Arg Gly Arg Ser Asp Tyr Asp Gly Ile Gly Asn Arg Glu Arg Pro
            100                 105                 110

Gly Phe Gly Arg Phe Glu Arg Ser Gly His Ser Arg Trp Cys Asp Lys
        115                 120                 125

Ser Val Glu Asp Asp Trp Ser Lys Pro Leu Pro Pro Ser Glu Arg Leu
    130                 135                 140

Glu Gln Glu Leu Phe Ser Gly Gly Asn Thr Gly Ile Asn Phe Glu Lys
145                 150                 155                 160

Tyr Asp Asp Ile Pro Val Glu Ala Thr Gly Ser Asn Cys Pro Pro His
                165                 170                 175

Ile Glu Asn Phe Ser Asp Ile Asp Met Gly Glu Ile Ile Met Gly Asn
            180                 185                 190

Ile Glu Leu Thr Arg Tyr Thr Arg Pro Thr Pro Val Gln Lys His Ala
        195                 200                 205

Ile Pro Ile Ile Lys Gly Lys Arg Asp Leu Val Ala Cys Ala Gln Thr
    210                 215                 220

Gly Ser Gly Lys Thr Ala Ala Phe Leu Leu Pro Ile Leu Ser Gln Ile
225                 230                 235                 240

Tyr Thr Asp Gly Pro Gly Glu Ala Leu Lys Ala Val Lys Glu Asn Gly
                245                 250                 255

Arg Tyr Gly Arg Arg Lys Gln Tyr Pro Ile Ser Leu Val Leu Ala Pro
            260                 265                 270

Thr Arg Glu Leu Ala Val Gln Ile Tyr Glu Glu Ala Arg Lys Phe Ser
        275                 280                 285

Tyr Arg Ser Arg Val Arg Pro Cys Val Val Tyr Gly Gly Ala Asp Ile
    290                 295                 300

Gly Gln Gln Ile Arg Asp Leu Glu Arg Gly Cys His Leu Leu Val Ala
305                 310                 315                 320

Thr Pro Gly Arg Leu Val Asp Met Met Glu Arg Gly Lys Ile Gly Leu
```

```
                325                 330                 335

Asp Phe Cys Lys Tyr Leu Val Leu Asp Glu Ala Asp Arg Met Leu Asp
            340                 345                 350

Met Gly Phe Glu Pro Gln Ile Arg Arg Ile Val Glu Gln Asp Thr Met
        355                 360                 365

Pro Pro Lys Gly Val Arg His Thr Met Met Phe Ser Ala Thr Phe Pro
    370                 375                 380

Lys Glu Ile Gln Met Leu Ala Arg Asp Phe Leu Asp Glu Tyr Ile Phe
385                 390                 395                 400

Leu Ala Val Gly Arg Val Gly Ser Thr Ser Glu Asn Ile Thr Gln Lys
                405                 410                 415

Val Val Trp Val Glu Asp Leu Asp Lys Arg Ser Phe Leu Leu Asp Ile
            420                 425                 430

Leu Gly Ala Thr Gly Ser Asp Ser Leu Thr Leu Val Phe Val Glu Thr
        435                 440                 445

Lys Lys Gly Ala Asp Ser Leu Glu Asp Phe Leu Tyr His Glu Gly Tyr
    450                 455                 460

Ala Cys Thr Ser Ile His Gly Asp Arg Ser Gln Arg Asp Arg Glu Glu
465                 470                 475                 480

Ala Leu His Gln Phe Arg Ser Gly Lys Ser Pro Ile Leu Val Ala Thr
                485                 490                 495

Ala Val Ala Ala Arg Gly Leu Asp Ile Ser Asn Val Arg His Val Ile
            500                 505                 510

Asn Phe Asp Leu Pro Ser Asp Ile Glu Glu Tyr Val His Arg Ile Gly
        515                 520                 525

Arg Thr Gly Arg Val Gly Asn Leu Gly Leu Ala Thr Ser Phe Phe Asn
    530                 535                 540

Glu Lys Asn Met Asn Ile Thr Lys Asp Leu Leu Asp Leu Leu Val Glu
545                 550                 555                 560

Ala Lys Gln Glu Val Pro Ser Trp Leu Glu Asn Met Ala Tyr Glu His
                565                 570                 575

His Tyr Lys Gly Gly Ser Arg Gly Arg Ser Lys Ser Asn Arg Phe Ser
            580                 585                 590

Gly Gly Phe Gly Ala Arg Asp Tyr Arg Gln Ser Ser Gly Ser Ser Ser
        595                 600                 605

Ser Gly Phe Gly Ala Ser Arg Gly Ser Ser Ser Arg Ser Gly Gly Gly
    610                 615                 620

Gly Tyr Gly Asp Ser Arg Gly Phe Gly Gly Gly Gly Tyr Gly Gly Phe
625                 630                 635                 640

Tyr Asn Ser Asp Gly Tyr Gly Gly Asn Tyr Asn Ser Gln Gly Val Asp
                645                 650                 655

Trp Trp Gly Asn
            660


<210> SEQ ID NO 31
<211> LENGTH: 482
<212> TYPE: DNA
<213> ORGANISM: Homo sapiens

<400> SEQUENCE: 31

gagaacttga agccaccatg ggagatgaag attgggaagc agaaatcaac cctcatatgt      60

cttcctatgt tcccatattt gagaaggata ggtattctgg agaaaatgga gacaatttta     120

acaggactcc agcttcatca tcagaaatgg atgatggacc ttctcgaaga gatcatttca     180
```

-continued

```
tgaaaagtgg atttgcctct gggcggaatt ttggaaacag agatgctggt gagtgtaata    240

agcgagataa tacatccaca atgggtggtt ttggagttgg aaagagtttt ggaaacagag    300

gtttttcaaa cagcaggttt gaagatggtg atagctcttg tttctggaga gagtctagta    360

atgactgcga agataatcca acacggaaca gaggggtttt caagaaaggc ggctatcgag    420

atggaaataa ttcagaagct tcagggccat acagagaggt ggagaggtag ttttccgagg    480

tg                                                                   482
```

<210> SEQ ID NO 32
<211> LENGTH: 555
<212> TYPE: DNA
<213> ORGANISM: Homo sapiens

<400> SEQUENCE: 32

```
tttgacattt agaatgcttt aatattccca gttaacacca tttgtatcag taactgcaat     60

gttgtaagtt ttagcatctc acataactag tcagtaagga tttttttttt aagtgtagga    120

gtgagaatac aaggacagga gctatgagaa tgttaagttt tatacttctg ttaaaaactc    180

aaaaatcaaa actattttct tctctgcatc aaaaccacag acttgaagga tgttttggct    240

ttaatcccat gactcatcat ctactggatt gggagcttgt gaagaagaaa acccagctgt    300

gttcaaagtg ctcttgccct ttctggtatc aactgatgca aacacgtttc ctcttgtact    360

accactgaag ccaggaatgt atgtactaaa ggcaatttct tccaaccatg caggaacatc    420

ctgttgagca tctgtcaata cttttactag aggctgtgct aaatggttat ccgattcaag    480

atcaaaaaag gaaattgctc tgccagtatt cccacaacga ccagtacgcc caattcgatg    540

aacatattca tcaat                                                     555
```

<210> SEQ ID NO 33
<211> LENGTH: 491
<212> TYPE: DNA
<213> ORGANISM: Homo sapiens

<400> SEQUENCE: 33

```
attgatgaat atgttcatcg aattgggcgt actggtcgtt gtgggaatac tggcagacaa     60

tttccttttt tgatcttgaa tcggataacc atttagcaca gcctctagta aaagtattga    120

cagatgctca acaggatgtt cctgcatggt tggaagaaat tgcctttagt acatacattc    180

ctggcttcag tggtagtaca agaggaaacg tgtttgcatc agttgatacc agaaagggca    240

agagcacttt gaacacagct gggttttctt cttcacaagc tcccaatcca gtagatgatg    300

agtcatggga ttaaagccaa aacatccttc aagtctgtgg ttttgatgca gagaagaaaa    360

tagttttgat tttgagtttt ttaacagaag tataaaactt aacattctca tagctcctgt    420

ccttgtattc tcactcctac acttaaaaaa aaaatcctta ctgactagtt atgtgagatg    480

ctaaaactta c                                                         491
```

<210> SEQ ID NO 34
<211> LENGTH: 335
<212> TYPE: DNA
<213> ORGANISM: Homo sapiens
<220> FEATURE:
<221> NAME/KEY: misc_feature
<222> LOCATION: (201)..(202)
<223> OTHER INFORMATION: n is a, c, g, or t

<400> SEQUENCE: 34

```
ttatatatgg gggaacccag ctgggacatt caattcgaca aatagtacaa ggctgtaata     60
```

```
tattatgtgc tactcctgga agactgatgg atatcatagg caaagaaaag attggtctca    120

aacagatcaa atacttagtt ttggatgaag ctgatcgcat gttggatatg ggttttggtc    180

cagaaatgaa gaagttaatt nnttgcccag gaatgccatc aaaggaacag cgccaaaccc    240

ttatgttcag tgcaactttt ccagaggaaa ttcaaaggtt ggctgcagag tttttaaagt    300

caaattatct gtttgttgct gttggacaag tgggt                               335


<210> SEQ ID NO 35
<211> LENGTH: 555
<212> TYPE: DNA
<213> ORGANISM: Homo sapiens
<220> FEATURE:
<221> NAME/KEY: misc_feature
<222> LOCATION: (546)..(546)
<223> OTHER INFORMATION: n is a, c, g, or t

<400> SEQUENCE: 35

tttttttttt tttttttttt ttttgacatt taaaatgctt taatattccc agttaacacc     60

atttgtatca gtaactgcaa tgttgtaagt tttagcatct cacataacta gtcagtaagg    120

attttttttt taagtgtagg agtgagaata caaggacagg agctatgaga atgttaagtt    180

ttatacttct gttaaaaact caaaaatcaa aactattttc ttctctgcat caaaaccaca    240

gacttgaagg atgttttggc tttaatccca tgactcatca tctactggat tgggagcttg    300

tgaagaagaa aacccagctg tgttcaaagt gctcttgccc tttctggtat caactgatgc    360

aaacacgttt cctcttgtac taccactgaa gccaggaatg tatgtactaa aggcaatttc    420

ttccaaccat gcaggaacat cctgttgagc atctgtcaat acttttacta gaggctgtgc    480

taaatggtta tccgattcaa gatcaaaaaa ggaaattgct ctgccagtat tcccacaacg    540

accagnacgc ccaat                                                     555


<210> SEQ ID NO 36
<211> LENGTH: 347
<212> TYPE: DNA
<213> ORGANISM: Homo sapiens

<400> SEQUENCE: 36

tttttttttt atgagaatgt taagttttat acttctgtta aaaactcaaa aatcaaaact     60

attttcttct ctgcatcaaa accacagact tgaaggatgt tttggcttta atcccatgac    120

tcatcatcta ctggattggg agcttgtgaa gaagaaaacc cagctgtgtt caaagtgctc    180

ttgccctttc tggtatcaac tgatgcaaac acgtttcctc ttgtactacc actgaagcca    240

ggaatgtatg tactaaaggc aatttcttcc aaccatgcag gaacatcctg ttgagcatct    300

gtcaatactt ttactagagg ctgtgctaaa tggttatccg attcaag                  347


<210> SEQ ID NO 37
<211> LENGTH: 469
<212> TYPE: DNA
<213> ORGANISM: Homo sapiens
<220> FEATURE:
<221> NAME/KEY: misc_feature
<222> LOCATION: (341)..(341)
<223> OTHER INFORMATION: n is a, c, g, or t

<400> SEQUENCE: 37

ttttgacatt tagaatgctt taatattccc agttaacacc atttgtatca gtaactgcaa     60

tgttgtaagt tttagcatct cacataacta gtcagtaagg attttttttt taagtgtagg    120
```

```
agtgagaata caaggacagg agctatgaga atgttaagtt ttatacttct gttaaaaact    180

caaaaatcaa aactattttc ttctctgcat caaaaccaca gacttgaagg atgttttggc    240

tttaatccca tgactcatca tctactggat tgggagcttg tgaagaagaa aacccagctg    300

tgttcaaagt gctcttgccc tttctggatc aactgatgca naaccgtttc ctcttgtact    360

accactgaag ccaggaatgt tgtactaaag gcaatttctt ccaaccatgc aggaacatcc    420

tgttgagcat ctgtcaatac tttactagaa gctgtgctaa atggttatc                469
```

```
<210> SEQ ID NO 38
<211> LENGTH: 300
<212> TYPE: DNA
<213> ORGANISM: Homo sapiens

<400> SEQUENCE: 38

aagtgtaggt ttgagaatac aaggacagga gctatgagaa tgttaagttt tatacttctg     60

ttaaaaactc aaaaatcaaa actattttct tctctgcatc aaaaccacag acttgaagga    120

tgttttggct ttaatcccat gactcatcat ctactggatt gggagcttgt gaagaagaaa    180

acccagctgt gttcaaagtg ctcttgccct ttctggtatc aactgatgca aacacgtttc    240

ctcttgtact accactgaag ccaggaatgt atgtactaaa ggcaatttct tccaaccatg    300
```

```
<210> SEQ ID NO 39
<211> LENGTH: 300
<212> TYPE: DNA
<213> ORGANISM: Homo sapiens

<400> SEQUENCE: 39

aagtgtagga gtgagaatac aaggacagga gctatgagaa tgttaagttt tatacttctg     60

ttaaaaactc aaaaatcaaa actattttct tctctgcatc aaaaccacag acttgaagga    120

tgttttggct ttaatcccat gactcatcat ctactggatt gggagcttgt gaagaagaaa    180

acccagctgt gttcaaagtg ctcttgccct ttctggtatc aactgatgca aacacgtttc    240

ctcttgtact accactgaag ccaggaatgt atgtactaaa ggcaatttct tccaaccatg    300
```

```
<210> SEQ ID NO 40
<211> LENGTH: 371
<212> TYPE: DNA
<213> ORGANISM: Homo sapiens

<400> SEQUENCE: 40

tttttttttt tttttttttt tttttttttt ttgacattta gaatgcttta atattcccag     60

ttaacaccat ttgtatcagt aactgcaatg ttgtaagttt tagcatctca cataactagt    120

cagtaaggat ttttttttta agtgtaggag tgagaataca aggacaggag ctatgagaat    180

gttaagtttt atacttctgt taaaaactca aaaatcaaaa ctattttctt ctctgcatca    240

aaaccacaga cttgaaggat gttttggctt taatcccatg actcatcatc tactggattg    300

ggagcttgtg aagaagaaaa cccagctgtg ttcaaagtgc tcttgccctt tctggtatca    360

actgatgcaa a                                                         371
```

```
<210> SEQ ID NO 41
<211> LENGTH: 108
<212> TYPE: DNA
<213> ORGANISM: Homo sapiens

<400> SEQUENCE: 41

gaatgtatgt actaaaggca atttcttcca accatgcagg aacatcctgt tgagcatctg     60
```

tcaatacttt tactagaggc tgtgctaaat ggttatccga ttcaagat 108

<210> SEQ ID NO 42
<211> LENGTH: 103
<212> TYPE: DNA
<213> ORGANISM: Homo sapiens

<400> SEQUENCE: 42
gaatgtatgt actataggca atttcttcca tccatgtcgg aacatcctgt tgagcatctg 60
tcaatacttt tactagaggc tgtgctacat ggctaaccga atc 103

<210> SEQ ID NO 43
<211> LENGTH: 100
<212> TYPE: DNA
<213> ORGANISM: Homo sapiens

<400> SEQUENCE: 43
gaatgtatgt actaaaggca atttcttcca accatgcagt gacatcatgt tgagcatctg 60
tcaatacttt tactagatgc tgtctataat aggtatcgga 100

<210> SEQ ID NO 44
<211> LENGTH: 79
<212> TYPE: DNA
<213> ORGANISM: Homo sapiens

<400> SEQUENCE: 44
ttctaccatt gatgaatatg ttcatcgact tgggcgtact ggtcgttgtg ggaatactgg 60
cagagcaagt ttcctttt 79

<210> SEQ ID NO 45
<211> LENGTH: 471
<212> TYPE: DNA
<213> ORGANISM: Homo sapiens

<400> SEQUENCE: 45
gaaagattgg attagacttt tgcaaatact tggtgttaga tgaagctgat cggatgttgg 60
atatggggtt tgagcctcag attcgtagaa tagtcgaaca agatactatg cctccaaagg 120
gtgtccgcca cactatgatg tttagtgcta cttttcctaa ggaaatacag atgctggctc 180
gtgatttctt agatgaatat atcttcttgg ctgtaggaag agttggctct acctctgaaa 240
acatcacaca gaaagtagtt tgggtggaag aatcagacaa acggtcattt ctgcttgacc 300
tcctaaatgc aacaggcaag gattcactga ccttagtgtt tgtggagacc aaaaagggtg 360
cagattctct ggaggatttc ttataccatg aaggatacgc atgtaccagc atccatggag 420
accgttctca gagggataga gaagaggccc ttcaacagtt ccgctcaggg a 471

<210> SEQ ID NO 46
<211> LENGTH: 381
<212> TYPE: DNA
<213> ORGANISM: Homo sapiens
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (378)..(378)

-continued

```
<223> OTHER INFORMATION: n is a, c, g, or t

<400> SEQUENCE: 46

ttttgcaaat acttggtgtt agatgaagct gatcggatgt tggatatggg gtttgagcct      60

cagattcgta gaatagtcga acaagatact atgcctccaa agggtgtccg ccacactatg     120

atgtttagtg ctacttttcc taaggaaata cagatgctgg ctcgtgattt cttaggatga     180

atatatcttc ttgggctgta gggaaggagt tgggctctac ctctggaaaa catcacacag     240

gaaagtagtt ggggtgggaa ggantcagga caaacgggtc atttctggct tgaccctccc     300

taaatggcaa caggggcaag ggatttcact tgaccnttag gtgttttgtg ggggagaccc     360

caaaaggggg tgccaggntt c                                               381


<210> SEQ ID NO 47
<211> LENGTH: 361
<212> TYPE: DNA
<213> ORGANISM: Homo sapiens

<400> SEQUENCE: 47

ttttgcaaat acttggtgtt agatgaagct gatcggatgt tggatatggg gtttgagcct      60

cagattcgta gaatagtcga acaagatact atgcctccaa agggtgtccg ccacactatg     120

atgtttagtg ctacttttcc taaggaaata cagatgctgg ctcgtgattt cttagatgaa     180

tatatcttct tgggctgtag ggaagagttg gctctacctc tgaaaacatc acacagaaag     240

tagttggggt gggaaggaat cagacaaacg gtcatttctg gcttggacct cctaaatggc     300

aacagggcaa gggttcactt gaccttagtg ttttgttggg agacccaaaa aggggtgcca     360

g                                                                     361
```